United States Patent
Swaller

(10) Patent No.: US 8,298,794 B2
(45) Date of Patent: Oct. 30, 2012

(54) CINNAMYL-ALCOHOL DEHYDROGENASES

(75) Inventor: Timothy Swaller, Newbury Park, CA (US)

(73) Assignee: Ceres, Inc., Thousand Oaks, CA (US)

(*) Notice: Subject to any disclaimer, the term of this patent is extended or adjusted under 35 U.S.C. 154(b) by 121 days.

(21) Appl. No.: 12/575,991

(22) Filed: Oct. 8, 2009

(65) Prior Publication Data
US 2010/0175144 A1 Jul. 8, 2010

Related U.S. Application Data

(60) Provisional application No. 61/104,067, filed on Oct. 9, 2008.

(51) Int. Cl.
*C12P 19/34* (2006.01)
*C12Q 1/68* (2006.01)
(52) U.S. Cl. ...................... 435/91.2; 435/6.12
(58) Field of Classification Search ................. None
See application file for complete search history.

(56) References Cited

U.S. PATENT DOCUMENTS

| | | |
|---|---|---|
| 4,987,071 A | 1/1991 | Cech et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,254,678 A | 10/1993 | Haseloff et al. |
| 5,538,880 A | 7/1996 | Lundquist et al. |
| 5,959,185 A | 9/1999 | Streit et al. |
| 5,973,234 A | 10/1999 | Mueller et al. |
| 5,977,445 A | 11/1999 | Soper et al. |
| 6,013,863 A | 1/2000 | Lundquist et al. |
| 6,326,527 B1 | 12/2001 | Kirihara et al. |
| 6,329,571 B1 | 12/2001 | Hiei |
| 6,423,885 B1 | 7/2002 | Waterhouse et al. |
| 6,452,067 B1 | 9/2002 | Bedbrook et al. |
| 6,573,099 B2 | 6/2003 | Graham |
| 6,753,139 B1 | 6/2004 | Baulcombe et al. |
| 6,777,588 B2 | 8/2004 | Waterhouse et al. |
| 7,135,615 B2 | 11/2006 | Kato |
| 7,173,121 B2 | 2/2007 | Fang |
| 7,214,789 B2 | 5/2007 | Pennell |
| 7,312,376 B2 | 12/2007 | Apuya et al. |
| 7,378,571 B2 | 5/2008 | Apuya |
| 7,402,667 B2 | 7/2008 | Cook et al. |
| 7,429,692 B2 | 9/2008 | Dang |
| 7,598,367 B2 | 10/2009 | Cook et al. |
| 2003/0175783 A1 | 9/2003 | Waterhouse et al. |
| 2003/0175965 A1 | 9/2003 | Lowe et al. |
| 2003/0180945 A1 | 9/2003 | Wang et al. |
| 2004/0214330 A1 | 10/2004 | Waterhouse et al. |
| 2006/0015970 A1 | 1/2006 | Pennell et al. |
| 2006/0021083 A1 | 1/2006 | Cook |
| 2006/0041952 A1 | 2/2006 | Cook |
| 2006/0260004 A1 | 11/2006 | Fang et al. |
| 2006/0265788 A1 | 11/2006 | Rommens |
| 2007/0006335 A1 | 1/2007 | Cook et al. |

FOREIGN PATENT DOCUMENTS

| | | |
|---|---|---|
| WO | 97/01952 | 1/1997 |
| WO | 98/36083 | 8/1998 |
| WO | 98/53083 | 11/1998 |
| WO | 99/32619 | 7/1999 |
| WO | 02/46449 | 6/2002 |
| WO | 2005/098007 | 10/2005 |
| WO | 2006/005023 | 1/2006 |
| WO | 2006/034479 | 3/2006 |
| WO | 2006/036864 | 4/2006 |
| WO | 2007/044988 | 4/2007 |
| WO | 2007/055826 | 5/2007 |
| WO | 2007/120989 | 10/2007 |

OTHER PUBLICATIONS

GRIN database accession No. PI:535790 submitted Sep. 15, 1989 accessed on Jun. 7, 2012.*
GRIN database accession No. PI:602730 accessed on Jun. 7, 2012.*
USDA plant inventory 1998.*
Sorghum newsletter 2003.*
U.S. Appl. No. 60/505,689, filed Sep. 23, 2003, Cook.
U.S. Appl. No. 60/518,075, filed Nov. 6, 2003, Pennell.
U.S. Appl. No. 60/544,771, filed Feb. 13, 2004, Cook.
U.S. Appl. No. 60/558,869, filed Apr. 1, 2004, Cook.
U.S. Appl. No. 60/583,609, filed Jun. 30, 2004, Alexandrov.
U.S. Appl. No. 60/583,691, filed Jun. 30, 2004, Alexandrov.
U.S. Appl. No. 60/612,891, filed Sep. 23, 2004, Kwok.
U.S. Appl. No. 60/637,140, filed Dec. 16, 2004, Fledman.
U.S. Appl. No. 60/757,544, filed Jan. 9, 2006, Dang.
U.S. Appl. No. 60/776,307, filed Feb. 24, 2006, Kwok.
Baerson et al., "Developmental regulation of an acyl carrier protein gene promoter in vegetative and reproductive tissues" *Plant Mol. Biol.*, 22(2):255-267 (1993).
Bateman et al., "Pfam 3.1: 1313 multiple alignments and profile HMMs match the majority of proteins" *Nucl. Acids Res.*, 27(1):260-262 (1999).
Bechtold et al., "In planta *Agrobacterium* mediated gene transfer by infiltration of adult *Arabidopsis thaliana* plants" *C.R. Acad. Sci. Paris*, 316:1194-1199 (1993).
Bout and Vermerris, "A candidate-gene approach to clone the sorghum Brown midrib gene encoding COMT," *Mol. Gen. Genomics*, 2003, 269: 205-214.
Casler et al., "Forage yield and economic losses associated with brown-midrib trait in sudangrass," *Crop Sci.*, 2003, 43: 782-789.
Cerdan et al., "A 146 bp fragment of the tobacco *Lhcb1*2* promoter confers very-low-fluence, low-fluence and high-irradiance responses of phytochrom to a minimal CaMV 35S promoter" *Plant Mol. Biol.*, 33:245-255 (1997).
Chen et al., "Functional analysis of regulatory elements in a plant embryo-specific gene" *Proc. Natl. Acad. Sci. USA*, 83:8560-8564 (1986).

(Continued)

*Primary Examiner* — Gary Benzion
*Assistant Examiner* — Suchira Pande
(74) *Attorney, Agent, or Firm* — Fish & Richardson P.C.

(57) ABSTRACT

The invention relates to nucleic acid and amino acid sequences for *sorghum* CAD alleles and truncated CAD polypeptides. *Sorghum* plants having such truncations or combinations thereof, methods of genotyping *sorghum* plants for CAD truncations, and methods for breeding *sorghum* plants having truncated CAD sequences or combinations thereof are described.

14 Claims, 21 Drawing Sheets

OTHER PUBLICATIONS

Chen et al., "A microsphere-based assay for multiplexed single nucleotide polymorphism analysis using single base chain extension," *Genome Res.*, 2000, 10: 549-557.

Chenna et al., "Multiple sequence alignment with the Clustal series of programs" *Nucleic Acids Res.*, 31(13):3497-3500 (2003).

Ching et al., "SNP frequency, haplotype structure and linkage disequilibrium in elite maize inbred lines," *BMC Genetics*, 2002, 3:19.

Conkling et al. "Isolation of transcriptionally regulated root-specific genes from tobacco" *Plant Physiol.*, 93:1203-1211, (1990).

Dai et al., "RF2b, a rice bZIP transcription activator, interacts with RF2a and is involved in symptom development of rice tungro disease" *Proc. Natl. Acad. Sci. USA*, 101(2):687-692 (2004).

de Feyter and Gaudron, Methods in Molecular Biology, vol. 74, Chapter 43, "Expressing Ribozymes in Plants", Edited by Turner, P.C., *Humana Press Inc.*, Totowa, NJ, 1997, pp. 403-415.

Fejes et al., "A 268 bp upstream sequence mediates the circadian clock-regulated transcription of the wheat Cab-1 gene in transgenic plants," *Plant Mol. Biol.*, 15:921-932 (1990).

Fromm et al., "An octopine synthase enhancer element directs tissue-specific expression and binds ASF-1, a factor from tobacco nuclear extracts" *The Plant Cell*, 1:977-984 (1989).

Gut, "Automation in genotyping single nucleotide polymorphisms," *Hum. Mutat.*, 2001, 17: 475-492.

Green et al., "Binding site requirements for pea nuclear protein factor GT-1 correlate with sequences required for light-dependent transcriptional activation of the *rbcS-3A* gene" *EMBO J.*, 7:4035-4044 (1988).

Hong et al., "Promoter sequences from two different *Brassica napus* tapetal oleosin-like genes direct tapetal expression of β-glucuronidase in transgenic *Brassica* plants" *Plant Mol Biol.*, 1997 34(3):549-555.

Jordano et al., "A sunflower helianthinin gene upstream sequence ensemble contains an enhancer and sites of nuclear protein interaction," *Plant Cell*, 1:855-866 (1989).

Keller and Baumgartner, "Vascular-specific expression of the bean GRP 1.8 gene is negatively regulated," *Plant Cell*, 3(10):1051-1061 (1991).

Lam et al., "Site-specific mutations in alter in vitro factor binding and change promoter expression pattern in transgenic plants" *Proc. Natl. Acad. Sci. USA*, 86:7890-7894 (1989).

Luan et al., "A rice *cab* gene promoter contains separate *cis*-acting elements that regulate expression in dicot and monocot plants," *The Plant Cell*, 4:971-981 (1992).

Lubberstedt et al., "Promoters from genes for plastid proteins possess regions with different sensitivities toward red and blue light," *Plant Physiol.*, 104:997-1006 (1994).

Matsuoka et al., "Tissue-specific light-regulated expression directed by the promoter of a C4 gene, maize pyruvate, orthophosphate dikinase, in a C3 plant, rice" *Proc. Natl. Acad. Sci. USA*, 90:9586-9590 (1993).

Medberry et al., "The Commelina yellow mottle virus promoter is a strong promoter in vascular and reproductive tissues" *Plant Cell*, 4(2):185-192 (1992).

Meier et al., "Elicitor-inducible and constitutive in vivo DNA footprints indicate novel *cis*-acting elements in the promoter of a parsley gene encoding pathogenesis-related protein 1" *Plant Cell*, 3:309-316 (1991).

Meuwissen et al., "Prediction of total genetic value using genome-wide dense marker maps," *Genetics*, 2001, 157: 1819-1829.

Nickerson et al., "PolyPhred: automating the detection and genotyping of single nucleotide substitutions using florescence-based resequencing," *Nucleic Acids Res.*, 1997, 25: 2745-2751.

Perriman et al., "Effective ribozyme delivery in plant cells" Proc. Natl. Acad. Sci. USA, 92(13):6175-6179 (1995).

Pfam web cite (describing concensus sequences for a variety of protein motifs and domains at sanger.ac.uk/Pham and genome.wustl. edu.Pfan, 2006.

Porter et al., "Phenotype, fiber composition, and in vitro dry matter disappearance of chemically induced brown midrib (bmr) mutants of sorghum," *Crop Science*, 1978, 18:205-208.

Rafalski et al., "The genetic diversity of components of rye hybrids," *Cell Mol. Biol. Lett.*, 2002, 7:471-475.

Riggs et al., "Cotyledon nuclear proteins bind to DNA fragments harboring regulatory elements of phytohemagglutinin genes" *Plant Cell*, 1(6):609-621 (1989).

Rivera et al, "Genomic evidence for two functionally distinct gene classes," *Proc. Natl. Acad. Sci. USA*, 95:6239-6244 (1998).

Slocombe et al., "Temporal and tissue-specific regulation of a *Brassica napus* stearoyl-acyl carrier protein desaturase gene" *Plant Physiol.*, 104(4):1167-1176 (1994).

Sonnhammer et al., "Pfam: A comprehensive database of protein domain families based on seed alignments," *Proteins*, 28:405-420 (1997).

Sonnhammer et al., "Pfam: multiple sequence alignments and HMM-profiles of protein domains," *Nucl. Acids Res.*, 26:320-322 (1998).

Suzuki et al., "5-hydroxyguaiacyl nuclei as aromatic constituents of native lignin," *Phytochemistry*, 1997, 46(4): 695-700.

Truernit et al., "The promoter of the *Arabidopsis thaliana* SUC2 sucrose-$H^+$ symporter gene directs expression of β-glucuronidase to the phloem: Evidence for phloem loading and unloading by SUC2" *Planta*. 196:564-570 (1995).

Underhill et al., "Detection of numerous Y chromosome biallelic polymorphisms by denaturing high-performance liquid chromatography," *Genome Res.*, 1997, 7: 996-1005.

Yamamoto et al., "The promoter of a pine photosynthetic gene allows expression of a β-glucuronidase reporter gene in transgenic rice plants in a light-independent but tissue-specific manner" *Plant Cell Physiol.*, 1994, 35:773-778.

Yan et al., "New construct approaches for efficient gene silencing in plants," *Plant Physiology*, 2006, 141: 1508-1518.

Zhang et al., "DNA sequences that activate isocitrate lyase gene expression during late embryogenesis and during postgerminative growth," *Plant Physiology*, 110:1069-1079 (1996).

Zheng et al., "*SPK1* Is an Essential S-Phase-Specific Gene of *Saccharomyces cerevisiae* that encodes a nuclear serine/threonine/tyrosine kinase" *Mol. Cell Biol.*, 1993, 13:5829-5842.

\* cited by examiner

| | | | | | | |
|---|---|---|---|---|---|---|
| SEQ_ID_NO_2 | GTTGATTATT | CCGATCAGGC | TGGAGGAAAT | TGAACAGCAC | TACATAAACC | 1544 |
| SEQ_ID_NO_13 | GTTGATTATT | CCGATCAGGC | TGGAGGAAAT | TGAACAGCAC | TACATAAACC | 1549 |
| SEQ_ID_NO_7 | GTTGATTATT | CCGATCAGGC | TGGAGGAAAT | TGAACAGCAC | TACATAAACC | 1549 |
| SEQ_ID_NO_4 | GTTGATTATT | CCGATCAGGC | TGGAGGAAAT | TGAACAGCAC | TACATAAACC | 1549 |
| SEQ_ID_NO_10 | GTTGATTATT | CCGATCAGGC | TGGAGGAAAT | TGAACAGCAC | TACATAAACC | 1549 |
| SEQ_ID_NO_2 | CTTGGCTTTC | GGTTCATTAA | GTAGTAGTAG | TCTTAATAGT | AGTAGTGGTC | 1594 |
| SEQ_ID_NO_13 | CTTGGCTTTC | GGTTCATTAA | GTAGTAGTAG | TCTTAATAGT | AGTAGTGGTC | 1599 |
| SEQ_ID_NO_7 | CTTGGCTTTC | GGTTCATTAA | GTAGTAGTAG | TCTTAATAGT | AGTAGTGGTC | 1599 |
| SEQ_ID_NO_4 | CTTGGCTTTC | GGTTCATTAA | GTAGTAGTAG | TCTTAATAGT | AGTAGTGGTC | 1599 |
| SEQ_ID_NO_10 | CTTGGCTTTC | GGTTCATTAA | GTAGTAGTAG | TCTTAATAGT | AGTAGTGGTC | 1599 |
| SEQ_ID_NO_2 | ACTAGGTTAT | GTGGTGCAGT | AATTTGAAAG | CATCCATCCA | TCGCCTGCAT | 1644 |
| SEQ_ID_NO_13 | ACTAGGTTAT | GTGGTGCAGT | AATTTGAAAG | CATCCATCCA | TCGCCTGCAT | 1649 |
| SEQ_ID_NO_7 | ACTAGGTTAT | GTGGTGCAGT | AATTTGAAAG | CATCCATCCA | TCGCCTGCAT | 1649 |
| SEQ_ID_NO_4 | ACTAGGTTAT | GTGGTGCAGT | AATTTGAAAG | CATCCATCCA | TCGCCTGCAT | 1649 |
| SEQ_ID_NO_10 | ACTAGGTTAT | GTGGTGCAGT | AATTTGAAAG | CATCCATCCA | TCGCCTGCAT | 1649 |
| SEQ_ID_NO_2 | ATACTTTTAT | TATTGCTTCG | AGAGAAGACT | CTTGCACTGC | TTTCTCATGT | 1694 |
| SEQ_ID_NO_13 | ATACTTTTAT | TATTGCTTCG | AGAGAAGACT | CTTGCACTGC | TTTCTCATGT | 1699 |
| SEQ_ID_NO_7 | ATACTTTTAT | TATTGCTTCG | AGAGAAGACT | CTTGCACTGC | TTTCTCATGT | 1699 |
| SEQ_ID_NO_4 | ATACTTTTAT | TATTGCTTCG | AGAGAAGACT | CTTGCACTGC | TTTCTCATGT | 1699 |
| SEQ_ID_NO_10 | ATACTTTTAT | TATTGCTTCG | AGAGAAGACT | CTTGCACTGC | TTTCTCATGT | 1699 |
| SEQ_ID_NO_2 | CATCAACTAC | TAGTGTACGA | TGATACTATC | TAGCTAACTG | TGGCGGTTCT | 1744 |
| SEQ_ID_NO_13 | CATCAACTAC | TAGTGTACGA | TGATACTATC | TAGCTAACTG | TGGCGGTTCT | 1749 |
| SEQ_ID_NO_7 | CATCAACTAC | TAGTGTACGA | TGATACTATC | TAGCTAACTG | TGGCGGTTCT | 1749 |
| SEQ_ID_NO_4 | CATCAACTAC | TAGTGTACGA | TGATACTATC | TAGCTAACTG | TGGCGGTTCT | 1749 |
| SEQ_ID_NO_10 | CATCAACTAC | TAGTGTACGA | TGATACTATC | TAGCTAACTG | TGGCGGTTCT | 1749 |
| SEQ_ID_NO_2 | TGCATATTTC | TATATGCTGC | TGGTCCTTCT | GCAAGAATAA | ACTAATTAAC | 1794 |
| SEQ_ID_NO_13 | TGCATATTTC | TATATGCTGC | TGGTCCTTCT | GCAAGAATAA | ACTAATTAAC | 1799 |
| SEQ_ID_NO_7 | TGCATATTTC | TATATGCTGC | TGGTCCTTCT | GCAAGAATAA | ACTAATTAAC | 1799 |
| SEQ_ID_NO_4 | TGCATATTTC | TATATGCTGC | TGGTCCTTCT | GCAAGAATAA | ACTAATTAAC | 1799 |
| SEQ_ID_NO_10 | TGCATATTTC | TATATGCTGC | TGGTCCTTCT | GCAAGAATAA | ACTAATTAAC | 1799 |

| | | | | | | | |
|---|---|---|---|---|---|---|---|
| SEQ_ID_NO_2 | AGCTAAAGAG | CTGCAGAAAT | GAGTAGTAAA | GCAAACCCCA | CCGGCCGGCC | 2444 |
| SEQ_ID_NO_13 | AGCTAAAGAG | CTGCAGAAAT | GAGTAGTAAA | GCAAACCCCA | CCGGCCGGCC | 2449 |
| SEQ_ID_NO_7 | AGCTAAAGAG | CTGCAGAAAT | GAGTAGTAAA | GCAAACCCCA | CCGGCCGGCC | 2449 |
| SEQ_ID_NO_4 | AGCTAAAGAG | CTGCAGAAAT | GAGTAGTAAA | GCAAACCCCA | CCGGCCGGCC | 2449 |
| SEQ_ID_NO_10 | AGCTAAAGAG | CTGCAGAAAT | GAGTAGTAAA | GCAAACCCCA | CCGGCCGGCC | 2449 |
| | | | | | | |
| SEQ_ID_NO_2 | TATATACCTT | TTTTCTGACA | TGTTTGCGAG | GGGGA_AAAA | ATTAAATAAA | 2493 |
| SEQ_ID_NO_13 | TATATACCTT | TTTTCTGACA | TGTTTGCGAG | GGGGAAAAAA | ATTAAATAAA | 2499 |
| SEQ_ID_NO_7 | TATATACCTT | TTTTCTGACA | TGTTTGCGAG | GGGGAAAAAA | ATTAAATAAA | 2499 |
| SEQ_ID_NO_4 | TATATACCTT | TTTTCTGACA | TGTTTGCGAG | GGGGAAAAAA | ATTAAATAAA | 2499 |
| SEQ_ID_NO_10 | TATATACCTT | TTTTCTGACA | TGTTTGCGAG | GGGGAAAAAA | ATTAAATAAA | 2499 |
| | | | | | | |
| SEQ_ID_NO_2 | CATAAACTTT | TCCTGACAGC | ACAACCACTC | CACTACTGCG | AACTGATAAT | 2543 |
| SEQ_ID_NO_13 | CATAAACTTT | TCCTGACAGC | ACAACCACTC | CACTACTGCG | AACTGATAAT | 2549 |
| SEQ_ID_NO_7 | CATAAACTTT | TCCTGACAGC | ACAACCACTC | CACTACTGCG | AACTGATAAT | 2549 |
| SEQ_ID_NO_4 | CATAAACTTT | TCCTGACAGC | ACAACCACTC | CACTACTGCG | AACTGATAAT | 2549 |
| SEQ_ID_NO_10 | CATAAACTTT | TCCTGACAGC | ACAACCACTC | CACTACTGCG | AACTGATAAT | 2549 |
| | | | | | | |
| SEQ_ID_NO_2 | GTGCACACTA | GCTATCATGG | GTTGGTTTTT | GCTAATGTCG | TGTGTCTGAA | 2593 |
| SEQ_ID_NO_13 | GTGCACACTA | GCTATCATGG | GTTGGTTTTT | GCTAATGTCG | TGTGTCTGAA | 2599 |
| SEQ_ID_NO_7 | GTGCACACTA | GCTATCATGG | GTTGGTTTTT | GCTAATGTCG | TGTGTCTGAA | 2599 |
| SEQ_ID_NO_4 | GTGCACACTA | GCTATCATGG | GTTGGTTTTT | GCTAATGTCG | TGTGTCTGAA | 2599 |
| SEQ_ID_NO_10 | GTGCACACTA | GCTATCATGG | GTTGGTTTTT | GCTAATGTCG | TGTGTCTGAA | 2599 |
| | | | | | | |
| SEQ_ID_NO_2 | ACTTTTGCAG | GCACGAGGTG | GTCGGTGAGG | TGGTGGAGGT | CGGGCCCGAG | 2643 |
| SEQ_ID_NO_13 | ACTTTTGCAG | GCACGAGGTG | GTCGGTGAGG | TGGTGGAGGT | CGGGCCCGAG | 2649 |
| SEQ_ID_NO_7 | ACTTTTGCAG | GCACGAGGTG | GTCGGTGAGG | TGGTGGAGGT | CGGGCCCGAG | 2649 |
| SEQ_ID_NO_4 | ACTTTTGCAG | GCACGAGGTG | GTCGGTGAGG | TGGTGGAGGT | CGGGCCCGAG | 2649 |
| SEQ_ID_NO_10 | ACTTTTGCAG | GCACGAGGTG | GTCGGTGAGG | TGGTGGAGGT | CGGGCCCGAG | 2649 |
| | | | | | | |
| SEQ_ID_NO_2 | GTGAGCAAGT | ACGGCGTCGG | CGACGTGGTA | GGCGTCGGGG | TGATCGTCGG | 2693 |
| SEQ_ID_NO_13 | GTGAGCAAGT | ACGGCGTCGG | CGACGTGGTA | GGCGTCGGGG | TGATCGTCGG | 2699 |
| SEQ_ID_NO_7 | GTGAGCAAGT | ACGGCGTCGG | CGACGTGGTA | GGCGTCGGGG | TGATCGTCGG | 2699 |
| SEQ_ID_NO_4 | GTGAGCAAGT | ACGGCGTCGG | CGACGTGGTA | GGCGTCGGGG | TGATCGTCGG | 2699 |
| SEQ_ID_NO_10 | GTGAGCAAGT | ACGGCGTCGG | CGACGTGGTA | GGCGTCGGGG | TGATCGTCGG | 2699 |

Figure 1I

| | | | | | | | |
|---|---|---|---|---|---|---|---|
| SEQ_ID_NO_2 | GTGCTGCCGC | GAGTGCAGCC | CGTGCAAGGC | CAACGTTGAG | CAGTACTGCA | | 2743 |
| SEQ_ID_NO_13 | GTGCTGCCGC | GAGTGCAGCC | CCTGCAAGGC | CAACGTTGAG | CAGTACTGCA | | 2749 |
| SEQ_ID_NO_7 | GTGCTGCCGC | GAGTGCAGCC | CCTGCAAGGC | CAACGTTGAG | CAGTACTGCA | | 2749 |
| SEQ_ID_NO_4 | GTGCTGCCGC | GAGTGCAGCC | CCTGCAAGGC | CAACGTTGAG | CAGTACTGCA | | 2749 |
| SEQ_ID_NO_10 | GTGCTGCCGC | GAGTGCAGCC | CCTGCAAGGC | CAACGTTGAG | CAGTACTGCA | | 2749 |
| | | | | | | | |
| SEQ_ID_NO_2 | ACAAGAAGAT | CTGGTCCTAC | AACGATGTCT | ACACTGACGG | CCGGCCCACG | | 2793 |
| SEQ_ID_NO_13 | ACAAGAAGAT | CTGGTCCTAC | AACGATGTCT | ACACTGACGG | CCGGCCCACG | | 2799 |
| SEQ_ID_NO_7 | ACAAGAAGAT | CTGGTCCTAC | AACGATGTCT | ACACTGACGG | CCGGCCCACG | | 2799 |
| SEQ_ID_NO_4 | ACAAGAAGAT | CTGGTCCTAC | AACGATGTCT | ACACTGACGG | CCGGCCCACG | | 2799 |
| SEQ_ID_NO_10 | ACAAGAAGAT | CTGGTCCTAC | AACGATGTCT | ACACTGACGG | CCGGCCCACG | | 2799 |
| | | | | | | | |
| SEQ_ID_NO_2 | CAGGGCGGCT | TCGCCTCCAC | AACGATGTCT | GACCAGAAGT | GAGTTTCTTG | | 2843 |
| SEQ_ID_NO_13 | TAGGGCGGCT | TCGCCTCCAC | CATGGTCGTC | GACCAGAAGT | GAGTTTCTTG | | 2849 |
| SEQ_ID_NO_7 | CAGGGCGGCT | TCGCCTCCAC | CATGGTCGTC | GACCAGAAGT | GAGTTTCTTG | | 2849 |
| SEQ_ID_NO_4 | CAGGGCGGCT | TCGCCTCCAC | CATGGTCGTC | GACCAGAAGT | GAGTTTCTTG | | 2849 |
| SEQ_ID_NO_10 | CAGGGCGGCT | TCGCCTCCAC | CATGGTCGTC | GACCAGAAGT | GAGTTTCTTG | | 2849 |
| | | | | | | | |
| SEQ_ID_NO_2 | AAACTGAAAA | CTAATCATCA | GGTTCATTCA | GCGTTATCTT | GCCTGCAGTG | | 2893 |
| SEQ_ID_NO_13 | AAACTGAAAA | CTAATCATCA | GGTTCATTCA | GCGTTATCTT | GCCTGCAGTG | | 2899 |
| SEQ_ID_NO_7 | AAACTGAAAA | CTAATCATCA | GGTTCATTCA | GCGTTATCTT | GCCTGCAGTG | | 2899 |
| SEQ_ID_NO_4 | AAACTGAAAA | CTAATCATCA | GGTTCATTCA | GCGTTATCTT | GCCTGCAGTG | | 2899 |
| SEQ_ID_NO_10 | AAACTGAAAA | CTAATCATCA | GGTTCATTCA | GCGTTATCTT | GCCTGCAGTG | | 2899 |
| | | | | | | | |
| SEQ_ID_NO_2 | TTCTAGCTAG | AGATAATTTC | TTGTTTTTTT | TTAAAAAAA | AAGTTGGTCT | | 2943 |
| SEQ_ID_NO_13 | TTCTAGCTAG | AGATAATTTC | TTGTTTTTTT | TTTTTAAAAA | AAGTTGGTCT | | 2949 |
| SEQ_ID_NO_7 | TTCTAGCTAG | AGATAATTTC | TTGTTTTTTT | TTTTTAAAAA | AAGTTGGTCT | | 2949 |
| SEQ_ID_NO_4 | TTCTAGCTAG | AGATAATTTC | TTGTTTTTTT | TTTTTAAAAA | AAGTTGGTCT | | 2949 |
| SEQ_ID_NO_10 | TTCTAGCTAG | AGATAATTTC | TTGTTTTTTT | TTTTTAAAAA | AAGTTGGTCT | | 2949 |
| | | | | | | | |
| SEQ_ID_NO_2 | GAAGTCTGAA | CTAAGCAAGA | AATAGTTGAG | CTTCAGTTTG | AACTTTTGTG | | 2993 |
| SEQ_ID_NO_13 | GAAGTCTGAA | CTAAGCAAGA | AATAGTTGAG | CTTCAGTTTG | AACTTTTGTG | | 2999 |
| SEQ_ID_NO_7 | GAAGTCTGAA | CTAAGCAAGA | AATAGTTGAG | CTTCAGTTTG | AACTTTTGTG | | 2999 |
| SEQ_ID_NO_4 | GAAGTCTGAA | CTAAGCAAGA | AATAGTTGAG | CTTCAGTTTG | AACTTTTGTG | | 2999 |
| SEQ_ID_NO_10 | GAAGTCTGAA | CTAAGCAAGA | AATAGTTGAG | CTTCAGTTTG | AACTTTTGTG | | 2999 |

Figure 1J

| | | | | | | |
|---|---|---|---|---|---|---|
| SEQ_ID_NO_2 | GAAGTGGATG | GTGATGTCCA | ATCCTTCTAG | AAAAGGTGGA | GGGGAGAGTA | 3043 |
| SEQ_ID_NO_13 | GAAGTGGATG | GTGATGTCCA | ATCCTTCTAG | AAAAGGTGGA | GGGGAGAGTA | 3049 |
| SEQ_ID_NO_7 | GAAGTGGATG | GTGATGTCCA | ATCCTTCTAG | AAAAGGTGGA | GGGGAGAGTA | 3049 |
| SEQ_ID_NO_4 | GAAGTGGATG | GTGATGTCCA | ATCCTTCTAG | AAAAGGTGGA | GGGGAGAGTA | 3049 |
| SEQ_ID_NO_10 | GAAGTGGATG | GTGATGTCCA | ATCCTTCTAG | AAAAGGTGGA | GGGGAGAGTA | 3049 |
| | | | | | | |
| SEQ_ID_NO_2 | TATGGGTATG | GGAAAAAATT | TATCATTGAG | AGAGTCCATC | ATCGTCCAGC | 3093 |
| SEQ_ID_NO_13 | TATGGGTATG | GGAAAAAATT | TATCATTGAG | AGAGTCCATC | ATCGTCCAGC | 3099 |
| SEQ_ID_NO_7 | TATGGGTATG | GGAAAAAATT | TATCATTGAG | AGAGTCCATC | ATCGTCCAGC | 3099 |
| SEQ_ID_NO_4 | TATGGGTATG | GGAAAAAATT | TATCATTGAG | AGAGTCCATC | ATCGTCCAGC | 3099 |
| SEQ_ID_NO_10 | TATGGGTATG | GGAAAAAATT | TATCATTGAG | AGAGTCCATC | ATCGTCCAGC | 3099 |
| | | | | | | |
| SEQ_ID_NO_2 | TGCAAGTCAG | CGTATGGATG | CCTTGTGGTG | ACCAGGCAAG | AGTGTGATGT | 3143 |
| SEQ_ID_NO_13 | TGCAAGTCAG | CGTATGGATG | CCTTGTGGTG | ACCAGGCAAG | AGTGTGATGT | 3149 |
| SEQ_ID_NO_7 | TGCAAGTCAG | CGTATGGATG | CCTTGTGGTG | ACCAGGCAAG | AGTGTGATGT | 3149 |
| SEQ_ID_NO_4 | TGCAAGTCAG | CGTATGGATG | CCTTGTGGTG | ACCAGGCAAG | AGTGTGATGT | 3149 |
| SEQ_ID_NO_10 | TGCAAGTCAG | CGTATGGATG | CCTTGTGGTG | ACCAGGCAAG | AGTGTGATGT | 3149 |
| | | | | | | |
| SEQ_ID_NO_2 | GAAAAGTACG | ACGTGGTGTG | CTTTACTGGC | TCATCTTTGT | CAAGTTGAAC | 3193 |
| SEQ_ID_NO_13 | GAAAAGTACG | ACGTGGTGTG | CTTTACTGGC | TCATCTTTGT | CAAGTTGAAC | 3199 |
| SEQ_ID_NO_7 | GAAAAGTACG | ACGTGGTGTG | CTTTACTGGC | TCATCTTTGT | CAAGTTGAAC | 3199 |
| SEQ_ID_NO_4 | GAAAAGTACG | ACGTGGTGTG | CTTTACTGGC | TCATCTTTGT | CAAGTTGAAC | 3199 |
| SEQ_ID_NO_10 | GAAAAGTACG | ACGTGGTGTG | CTTTACTGGC | TCATCTTTGT | CAAGTTGAAC | 3199 |
| | | | | | | |
| SEQ_ID_NO_2 | CATAACCACA | GAAGCCGAAT | CCTCACCTAC | TACTCACTAC | TCATGTCTGA | 3243 |
| SEQ_ID_NO_13 | CATAACCACA | GAAGCCGAAT | CCTCACCTAC | TACTCACTAC | TCATGTCTGA | 3249 |
| SEQ_ID_NO_7 | CATAACCACA | GAAGCCGAAT | CCTCACCTAC | TACTCACTAC | TCATGTCTGA | 3249 |
| SEQ_ID_NO_4 | CATAACCACA | GAAGCCGAAT | CCTCACCTAC | TACTCACTAC | TCATGTCTGA | 3249 |
| SEQ_ID_NO_10 | CATAACCACA | GAAGCCGAAT | CCTCACCTAC | TACTCACTAC | TCATGTCTGA | 3249 |
| | | | | | | |
| SEQ_ID_NO_2 | AGATTGGTCA | TCCAAACCAT | CACTGGTTGT | TGGGAGAAAT | GGGGATAACT | 3293 |
| SEQ_ID_NO_13 | AGATTGGTCA | TCCAAACCAT | CACTGGTTGT | TGGGAGAAAT | GGGGATAACT | 3299 |
| SEQ_ID_NO_7 | AGATTGGTCA | TCCAAACCAT | CACTGGTTGT | TGGGAGAAAT | GGGGATAACT | 3299 |
| SEQ_ID_NO_4 | AGATTGGTCA | TCCAAACCAT | CACTGGTTGT | TGGGAGAAAT | GGGGATAACT | 3299 |
| SEQ_ID_NO_10 | AGATTGGTCA | TCCAAACCAT | CACTGGTTGT | TGGGAGAAAT | GGGGATAACT | 3299 |

| | | | | | | |
|---|---|---|---|---|---|---|
| SEQ_ID_NO_2 | CTGGAGCCCT | ACCTGTCGCT | GCTGAGGCTG | GACGGCAAGC | ACGTGCTGCT | 3943 |
| SEQ_ID_NO_13 | CTGGAGCCCT | ACCTGTCGCT | GCTGAGGCTG | GACGGCAAGC | ACGTGCTGCT | 3949 |
| SEQ_ID_NO_7 | CTGGAGCCCT | ACCTGTCGCT | GCTGAGGCTG | GACGGCAAGC | ACGTGCTGCT | 3949 |
| SEQ_ID_NO_4 | CTGGAGCCCT | ACCTGTCGCT | GCTGAGGCTG | GACGGCAAGC | ACGTGCTGCT | 3949 |
| SEQ_ID_NO_10 | CTGGAGCCCT | ACCTGTCGCT | GCTGAGGCTG | GACGGCAAGC | ACGTGCTGCT | 3949 |

| | | | | | | |
|---|---|---|---|---|---|---|
| SEQ_ID_NO_2 | GGGCGTCATC | GGCGAGCCCC | TCAGCTTCGT | GTCCCGATG | GTGATGCTGG | 3993 |
| SEQ_ID_NO_13 | GGGCGTCATC | GGCGAGCCCC | TCAGCTTCGT | GTCCCGATG | GTGATGCTGG | 3999 |
| SEQ_ID_NO_7 | GGGCGTCATC | GGCGAGCCCC | TCAGCTTCGT | GTCCCGATG | GTGATGCTGG | 3999 |
| SEQ_ID_NO_4 | GGGCGTCATC | GGCGAGCCCC | TCAGCTTCGT | GTCCCGATG | GTGATGCTGG | 3999 |
| SEQ_ID_NO_10 | GGGCGTCATC | GGCGAGCCCC | TCAGCTTCGT | GTCCCGATG | GTGATGCTGG | 3999 |

| | | | | | | |
|---|---|---|---|---|---|---|
| SEQ_ID_NO_2 | GGCGGAAGGC | CATCAC GGG | GAGCTTCATC | GGCAGCATCG | ACGAGACCGC | 4042 |
| SEQ_ID_NO_13 | GGCGGAAGGC | CATCAC GGG | GAGCTTCATC | GGCAGCATCG | ACGAGACCGC | 4048 |
| SEQ_ID_NO_7 | GGCGGAAGGC | CATCAC GGG | GAGCTTCATC | GGCAGCATCG | ACGAGACCGC | 4048 |
| SEQ_ID_NO_4 | GGCGGAAGGC | CATCAC GGG | GAGCTTCATC | GGCAGCATCG | ACGAGACCGC | 4048 |
| SEQ_ID_NO_10 | GGCGGAAGGC | CATCACGGGG | GAGCTTCATC | GGCAGCATCG | ACGAGACCGC | 4049 |

| | | | | | | |
|---|---|---|---|---|---|---|
| SEQ_ID_NO_2 | CGAGGTGCTC | CAGTTCTGCG | TCGACAAGGG | GCTCACCTCC | CAGATCGAGG | 4092 |
| SEQ_ID_NO_13 | CGAGGTGCTC | CAGTTCTGCG | TCGACAAGGG | GCTCACCTCC | CAGATCGAGG | 4098 |
| SEQ_ID_NO_7 | CGAGGTGCTC | CAGTTCTGCG | TCGACAAGGG | GCTCACCTCC | TAGATCGAGG | 4098 |
| SEQ_ID_NO_4 | CGAGGTGCTC | CAGTTCTGCG | TCGACAAGGG | GCTCACCTCC | CAGATCGAGG | 4098 |
| SEQ_ID_NO_10 | CGAGGTGCTC | CAGTTCTGCG | TCGACAAGGG | GCTCACCTCC | CAGATCGAGG | 4099 |

| | | | | | | |
|---|---|---|---|---|---|---|
| SEQ_ID_NO_2 | TGGTCAAGAT | GGGGTACGTG | AACGAGGCGC | TGGAGCGGCT | CGAGCGCAAC | 4142 |
| SEQ_ID_NO_13 | TGGTCAAGAT | GGGGTACGTG | AACGAGGCGC | TGGAGCGGCT | CGAGCGCAAC | 4148 |
| SEQ_ID_NO_7 | TGGTCAAGAT | GGGGTACGTG | AACGAGGCGC | TGGAGCGGCT | CGAGCGCAAC | 4148 |
| SEQ_ID_NO_4 | TGGTCAAGAT | GGGGTACGTG | AACGAGGCGC | TGGAGCGGCT | CGAGCGCAAC | 4148 |
| SEQ_ID_NO_10 | TGGTCAAGAT | GGGGTACGTG | AACGAGGCGC | TGGAGCGGCT | CGAGCGCAAC | 4149 |

| | | | | | | |
|---|---|---|---|---|---|---|
| SEQ_ID_NO_2 | GACGTCCGCT | ACCGCTTCGT | CGTCGACGTC | GCGGCAGCA | ACGTCGAGGA | 4192 |
| SEQ_ID_NO_13 | GACGTCCGCT | ACCGCTTCGT | CGTCGACGTC | GCGGCAGCA | ACGTCGAGGA | 4198 |
| SEQ_ID_NO_7 | GACGTCCGCT | ACCGCTTCGT | CGTCGACGTC | GCGGCAGCA | ACGTCGAGGA | 4198 |
| SEQ_ID_NO_4 | GACGTCCGCT | ACCGCTTCGT | CGTCGACGTC | GCGGCAGCA | ACGTCGAGGA | 4198 |
| SEQ_ID_NO_10 | GACGTCCGCT | ACCGCTTCGT | CGTCGACGTC | GCGGCAGCA | ACGTCGAGGA | 4199 |

Figure 1N

| | | | | | | |
|---|---|---|---|---|---|---|
| SEQ_ID_NO_2 | GGATGCCGCT | GATGCGCCGA | GCAACTGACG | GCGTGCAACG | TTCGTTCGGG | 4242 |
| SEQ_ID_NO_13 | GGATGCCGCT | GATGCGCCGA | GCAACTGACG | GCGTGCAACG | TTCGTTCGGG | 4248 |
| SEQ_ID_NO_7 | GGATGCCGCT | GATGCGCCGA | GCAACTGA | | | 4226 |
| SEQ_ID_NO_4 | GGATGCCGCT | GATGCGCCGA | GCAACTGACG | GCGTGCAACG | TTCGTTCGGG | 4248 |
| SEQ_ID_NO_10 | GGATGCCGCT | GATGCGCCGA | GCAACTGA | | | 4227 |

| | | | | | | |
|---|---|---|---|---|---|---|
| SEQ_ID_NO_2 | GCTCGAGGCT | GCCTGCGCTT | CTGCTTCCTT | TAGTAATGGT | GGGCTTAAAA | 4292 |
| SEQ_ID_NO_13 | GCTCGAGGCT | GCCTGCGCTT | CTGCTTCCTT | TAGTAATTGT | GGGCTTAAAA | 4298 |
| SEQ_ID_NO_7 | | | | | | 4226 |
| SEQ_ID_NO_4 | GCTCGAGGCT | GCCTGCGCTT | CTGCTTCCTT | TAAAATGGGg | GGGCCTAAAg | 4298 |
| SEQ_ID_NO_10 | | | | | | 4227 |

Figure 10

| | | | | | | |
|---|---|---|---|---|---|---|
| SEQ_ID_NO_1 | GATCGCCCAC | CCTCTCGGCC | TCTCCAGGCC | GCCGCCGGCT | CCGTCGTCGT | 50 |
| SEQ_ID_NO_14 | ---------- | ---------- | ---------- | ---------- | ---------- | 0 |
| SEQ_ID_NO_11 | ---------- | ---------- | ---------- | ---------- | ---------- | 0 |
| SEQ_ID_NO_8 | ---------- | ---------- | ---------- | ---------- | ---------- | 0 |
| SEQ_ID_NO_5 | ---------- | ---------- | ---------- | ---------- | ---------- | 0 |
| SEQ_ID_NO_3 | ---------- | ---------- | ---------- | ---------- | ---------- | 0 |
| SEQ_ID_NO_1 | GTTCCCCGAC | GCCCGTAGCG | TTCGACCGCG | GCCAGTCCCA | GTCCAAGAGG | 100 |
| SEQ_ID_NO_14 | ---------- | ---------- | ---------- | ---------- | ---------- | 0 |
| SEQ_ID_NO_11 | ---------- | ---------- | ---------- | ---------- | ---------- | 0 |
| SEQ_ID_NO_8 | ---------- | ---------- | ---------- | ---------- | ---------- | 0 |
| SEQ_ID_NO_5 | ---------- | ---------- | ---------- | ---------- | ---------- | 0 |
| SEQ_ID_NO_3 | ---------- | ---------- | ---------- | ---------- | ---------- | 0 |
| SEQ_ID_NO_1 | AGAATGGGGA | GCCTGGCGTC | CGAGAGGAAG | GTGGTCGGCT | GGGCCGCCAG | 150 |
| SEQ_ID_NO_14 | ---ATGGGGA | GCCTGGCGTC | CGAGAGGAAG | GTGGTCGGCT | GGGCCGCCAG | 47 |
| SEQ_ID_NO_11 | ---ATGGGGA | GCCTGGCGTC | CGAGAGGAAG | GTGGTCGGCT | GGGCCGCCAG | 47 |
| SEQ_ID_NO_8 | ---ATGGGGA | GCCTGGCGTC | CGAGAGGAAG | GTGGTCGGCT | GGGCCGCCAG | 47 |
| SEQ_ID_NO_5 | ---ATGGGGA | GCCTGGCGTC | CGAGAGGAAG | GTGGTCGGCT | GGGCCGCCAG | 47 |
| SEQ_ID_NO_3 | ---ATGGGGA | GCCTGGCGTC | CGAGAGGAAG | GTGGTCGGCT | GGGCCGCCAG | 47 |
| SEQ_ID_NO_1 | GGACGCCACC | GGACACCTCT | CCCCCTACAC | CTACACCCTC | AGGAACACAG | 200 |
| SEQ_ID_NO_14 | GGACGCCACC | GGACACCTCT | CCCCCTACAC | CTACACCCTC | AGGAACACAG | 97 |
| SEQ_ID_NO_11 | GGACGCCACC | GGACACCTCT | CCCCCTACAC | CTACACCCTC | AGGAACACAG | 97 |
| SEQ_ID_NO_8 | GGACGCCACC | GGACACCTCT | CCCCCTACAC | CTACACCCTC | AGGAACACAG | 97 |
| SEQ_ID_NO_5 | GGACGCCACC | GGACACCTCT | CCCCCTACAC | CTACACCCTC | AGGAACACAG | 97 |
| SEQ_ID_NO_3 | GGACGCCACC | GGACACCTCT | CCCCCTACAC | CTACACCCTC | AGGAACACAG | 97 |
| SEQ_ID_NO_1 | GCCCTGAAGA | TGTGGTGGTG | AAGGTGCTCT | ACTGTGGAAT | CTGCCACACG | 250 |
| SEQ_ID_NO_14 | GCCCTGAAGA | TGTGGTGGTG | AAGGTGCTCT | ACTGTGGAAT | CTGCCACACG | 147 |
| SEQ_ID_NO_11 | GCCCTGAAGA | TGTGGTGGTG | AAGGTGCTCT | ACTGTGGAAT | CTGCCACACG | 147 |
| SEQ_ID_NO_8 | GCCCTGAAGA | TGTGGTGGTG | AAGGTGCTCT | ACTGTGGAAT | CTGCCACACG | 147 |
| SEQ_ID_NO_5 | GCCCTGAAGA | TGTGGTGGTG | AAGGTGCTCT | ACTGTGGAAT | CTGCCACACG | 147 |
| SEQ_ID_NO_3 | GCCCTGAAGA | TGTGGTGGTG | AAGGTGCTCT | ACTGTGGAAT | CTGCCACACG | 147 |

| | | | | | | |
|---|---|---|---|---|---|---|
| SEQ_ID_NO_1 | GCGCGCGGAG | GCGATGGACC | ACCTGGGCGC | GGACGCGTAC | CTGGTGAGCA | 800 |
| SEQ_ID_NO_14 | GCGCGCGGAG | GCGATGGACC | ACCTGGGCGC | GGACGCGTAC | CTGGTGAGCA | 697 |
| SEQ_ID_NO_11 | GCGCGCGGAG | GCGATGGACC | ACCTGGGCGC | GGACGCGTAC | CTGGTGAGCA | 697 |
| SEQ_ID_NO_8 | GCGCGCGGAG | GCGATGGACC | ACCTGGGCGC | GGACGCGTAC | CTGGTGAGCA | 697 |
| SEQ_ID_NO_5 | GCGCGCGGAG | GCGATGGACC | ACCTGGGCGC | GGACGCGTAC | CTGGTGAGCA | 697 |
| SEQ_ID_NO_3 | GCGCGCGGAG | GCGATGGACC | ACCTGGGCGC | GGACGCGTAC | CTGGTGAGCA | 697 |
| | | | | | | |
| SEQ_ID_NO_1 | CGGACGCGGC | GGCCATGGGC | GCGGCCGCCG | ACTCGCTGGA | CTACATCATC | 850 |
| SEQ_ID_NO_14 | CGGACGCGGC | GGCCATGGGC | GCGGCCGCCG | ACTCGCTGGA | CTACATCATC | 747 |
| SEQ_ID_NO_11 | CGGACGCGGC | GGCCATGGGC | GCGGCCGCCG | ACTCGCTGGA | CTACATCATC | 747 |
| SEQ_ID_NO_8 | CGGACGCGGC | GGCCATGGGC | GCGGCCGCCG | ACTCGCTGGA | CTACATCATC | 747 |
| SEQ_ID_NO_5 | CGGACGCGGC | GGCCATGGGC | GCGGCCGCCG | ACTCGCTGGA | CTACATCATC | 747 |
| SEQ_ID_NO_3 | CGGACGCGGC | GGCCATGGGC | GCGGCCGCCG | ACTCGCTGGA | CTACATCATC | 747 |
| | | | | | | |
| SEQ_ID_NO_1 | GACACGGTGC | CCGTGCACCA | CCCGCTGGAG | CCCTACCTGT | CGCTGCTGAG | 900 |
| SEQ_ID_NO_14 | GACACGGTGC | CCGTGCACCA | CCCGCTGGAG | CCCTACCTGT | CGCTGCTGAG | 797 |
| SEQ_ID_NO_11 | GACACGGTGC | CCGTGCACCA | CCCGCTGGAG | CCCTACCTGT | CGCTGCTGAG | 797 |
| SEQ_ID_NO_8 | GACACGGTGC | CCGTGCACCA | CCCGCTGGAG | CCCTACCTGT | CGCTGCTGAG | 797 |
| SEQ_ID_NO_5 | GACACGGTGC | CCGTGCACCA | CCCGCTGGAG | CCCTACCTGT | CGCTGCTGAG | 797 |
| SEQ_ID_NO_3 | GACACGGTGC | CCGTGCACCA | CCCGCTGGAG | CCCTACCTGT | CGCTGCTGAG | 797 |
| | | | | | | |
| SEQ_ID_NO_1 | GCTGGACGGC | AAGCACGTGC | TGCTGGGCGT | CATCGGCGAG | CGCTGCTGAG | 950 |
| SEQ_ID_NO_14 | GCTGGACGGC | AAGCACGTGC | TGCTGGGCGT | CATCGGCGAG | CGCTGCTGAG | 847 |
| SEQ_ID_NO_11 | GCTGGACGGC | AAGCACGTGC | TGCTGGGCGT | CATCGGCGAG | CGCTGCTGAG | 847 |
| SEQ_ID_NO_8 | GCTGGACGGC | AAGCACGTGC | TGCTGGGCGT | CATCGGCGAG | CGCTGCTGAG | 847 |
| SEQ_ID_NO_5 | GCTGGACGGC | AAGCACGTGC | TGCTGGGCGT | CATCGGCGAG | CGCTGCTGAG | 847 |
| SEQ_ID_NO_3 | GCTGGACGGC | AAGCACGTGC | TGCTGGGCGT | CATCGGCGAG | CGCTGCTGAG | 847 |
| | | | | | | |
| SEQ_ID_NO_1 | TCGTGTCCCC | GATGGTGATG | CTGGGGCGGA | AGGCCATCAC | CCCCTCAGCT | GGAGCTT 999 |
| SEQ_ID_NO_14 | TCGTGTCCCC | GATGGTGATG | CTGGGGCGGA | AGGCCATCAC | CCCCTCAGCT | GG-GGAGCTT 896 |
| SEQ_ID_NO_11 | TCGTGTCCCC | GATGGTGATG | CTGGGGCGGA | AGGCCATCAC | CCCCTCAGCT | GGGGGAGCTT 897 |
| SEQ_ID_NO_8 | TCGTGTCCCC | GATGGTGATG | CTGGGGCGGA | AGGCCATCAC | CCCCTCAGCT | GG-GGAGCTT 896 |
| SEQ_ID_NO_5 | TCGTGTCCCC | GATGGTGATG | CTGGGGCGGA | AGGCCATCAC | CCCCTCAGCT | GG-GGAGCTT 896 |
| SEQ_ID_NO_3 | TCGTGTCCCC | GATGGTGATG | CTGGGGCGGA | AGGCCATCAC | CCCCTCAGCT | GG-GGAGCTT 896 |

| | | | |
|---|---|---|---|
| SEQ_ID_NO_1 | CCTTTAGTAA TTGTGGGCTT TGTGCCGTTCT TGCCGTGTTC TGTTCTGGTT | 1299 |
| SEQ_ID_NO_14 | ---------- ---------- ---------- ---------- ---------- | 1098 |
| SEQ_ID_NO_11 | ---------- ---------- ---------- ---------- ---------- | 1099 |
| SEQ_ID_NO_8 | ---------- ---------- ---------- ---------- ---------- | 1098 |
| SEQ_ID_NO_5 | ---------- ---------- ---------- ---------- ---------- | 1098 |
| SEQ_ID_NO_3 | ---------- ---------- ---------- ---------- ---------- | 1098 |
| | | |
| SEQ_ID_NO_1 | CTGGGCTTTC AGATGAGTTG AAGGATGGTC TGTTTAAATG GCATCAGACT | 1349 |
| SEQ_ID_NO_14 | ---------- ---------- ---------- ---------- ---------- | 1098 |
| SEQ_ID_NO_11 | ---------- ---------- ---------- ---------- ---------- | 1099 |
| SEQ_ID_NO_8 | ---------- ---------- ---------- ---------- ---------- | 1098 |
| SEQ_ID_NO_5 | ---------- ---------- ---------- ---------- ---------- | 1098 |
| SEQ_ID_NO_3 | ---------- ---------- ---------- ---------- ---------- | 1098 |
| | | |
| SEQ_ID_NO_1 | GAATAACTAT ATGTTGTAGT AGTACGTGTT ATACTCGGAG TACGCCACGA | 1399 |
| SEQ_ID_NO_14 | ---------- ---------- ---------- ---------- ---------- | 1098 |
| SEQ_ID_NO_11 | ---------- ---------- ---------- ---------- ---------- | 1099 |
| SEQ_ID_NO_8 | ---------- ---------- ---------- ---------- ---------- | 1098 |
| SEQ_ID_NO_5 | ---------- ---------- ---------- ---------- ---------- | 1098 |
| SEQ_ID_NO_3 | ---------- ---------- ---------- ---------- ---------- | 1098 |
| | | |
| SEQ_ID_NO_1 | TATGGTGTGG TGTCAGTGTC ACCAGCATTC TGGATTTGCA GTTTACCCAA | 1449 |
| SEQ_ID_NO_14 | ---------- ---------- ---------- ---------- ---------- | 1098 |
| SEQ_ID_NO_11 | ---------- ---------- ---------- ---------- ---------- | 1099 |
| SEQ_ID_NO_8 | ---------- ---------- ---------- ---------- ---------- | 1098 |
| SEQ_ID_NO_5 | ---------- ---------- ---------- ---------- ---------- | 1098 |
| SEQ_ID_NO_3 | ---------- ---------- ---------- ---------- ---------- | 1098 |
| | | |
| SEQ_ID_NO_1 | AAAAAAAA | 1457 |
| SEQ_ID_NO_14 | -------- | 1098 |
| SEQ_ID_NO_11 | -------- | 1099 |
| SEQ_ID_NO_8 | -------- | 1098 |
| SEQ_ID_NO_5 | -------- | 1098 |
| SEQ_ID_NO_3 | -------- | 1098 |

Figure 2F

CINNAMYL-ALCOHOL DEHYDROGENASES

CROSS-REFERENCE TO RELATED APPLICATIONS

This application claims priority under 35 U.S.C. §119 to U.S. Provisional Application Ser. No. 61/104,067, filed Oct. 9, 2008, which is incorporated herein by reference in its entirety.

INCORPORATION-BY-REFERENCE OF SEQUENCE LISTING OR TABLE

The material in the accompanying sequence listing is hereby incorporated by reference into this application. The accompanying file, named sequence.txt was created on Oct. 9, 2008, and is 106 KB. The file can be accessed using Microsoft Word on a computer that uses Windows OS.

TECHNICAL FIELD

This document relates to methods, materials, and kits involved in identifying cinnamyl-alcohol dehydrogenases (CAD) alleles in sorghum germplasm and breeding methods to incorporate CAD alleles encoding truncated CAD polypeptides into desired sorghum germplasm lines or elite sorghum breeding lines. Methods for generating truncated CAD coding sequences through mutation of sorghum or preparation of synthetic sequences are also described herein as well as methods for generating transgenic plants expressing truncated CAD coding sequences. This document also relates to sorghum plants having a novel combination of CAD alleles and/or caffeic acid O-methyltransferase (COMT) alleles encoding truncated polypeptides as well as materials and methods for making such plants.

BACKGROUND

Numerous strategies are being employed to enhanced biomass conversion characteristics in dedicated energy crops such as sorghum. Plant transformation, use of naturally occurring variation, and plant breeding can be used to achieve desirable cell wall composition and structure which is determined largely by content and composition of lignin, cellulose, hemicellulose, and the way they are cross-linked. CAD is associated with lignin biosynthesis. In sorghum, there is a need for identifying germplasm having altered lignin or lignin content and developing markers associated with such traits for use in breeding. The truncated CAD sequences described herein and markers associated with such truncations will expedite the selection of superior new varieties of sorghum with enhanced biofuel conversion properties and/or forage properties. For example, the introduction of sweet sorghum and/or truncated CAD traits into a high biomass staygreen sorghum germplasm may improve yields and conversion properties dramatically.

SUMMARY

This document provides materials and methods involved in identifying alleles encoding truncated CAD polypeptides in sorghum germplasm. This document also provides breeding methods to incorporate alleles encoding truncated CAD polypeptides in to desired sorghum germplasm lines or elite sorghum breeding lines. For example, this document provides isolated nucleic acids, transgenic plant cells and plants and plant tissues produced from transgenic plant cells, as well as plants of agronomically elite varieties. This document provides methods for producing plants comprising CAD encoding nucleic acids, for incorporating a desired trait into a sorghum cultivar, for characterizing and breeding sorghum plants, and for modulating the composition of a plant. Also, this document provides kits to genotype a sorghum biological sample. The material, methods and kits provided herein can be used to achieve desirable cell wall composition and structure, and advance the selection of advantageous varieties of sorghum for production of biomass with improved digestibility, which may benefit both humans and animals.

Isolated nucleic acids encoding truncated CAD polypeptides are provided herein. In some embodiments, an isolated nucleic acid comprises a sequence encoding a CAD polypeptide. The CAD polypeptide comprises at least 98% sequence identity to amino acids 1-130 or 1-319 of SEQ ID NO: 6 and terminates at a position corresponding to residue 131 or 320 of SEQ ID NO: 6. In some embodiments, an isolated nucleic acid comprises a sequence encoding a sorghum CAD polypeptide. The sorghum CAD polypeptide comprises at least 80% sequence identity to amino acids 1-130 or 1-319 of SEQ ID NO: 6 and terminates at a position corresponding to residue 131 or 320 of SEQ ID NO: 6. In some embodiments, the nucleic acid encoding a CAD polypeptide having at least 98% or at least 80% sequence identity to amino acids 1-130 or 1-319, and terminating at a position corresponding to residue 131 or 320 of SEQ ID NO: 6 further comprises a thymine corresponding to position 2794 of SEQ ID NO:2, position 2800 of SEQ ID NO: 4, 7, 10, or 13, position 4083 SEQ ID NO: 2, position 4089 of SEQ ID NOs: 4 or 7, position 4090 of SEQ ID NO: 10, position 497 of SEQ ID NO: 1, position 394 of SEQ ID NOs: 3, 5, 8, 11, or 14, position 1064 of SEQ ID NO:1, position 962 of SEQ ID NO:11, or position 961 of SEQ ID NOs: 3, 5, or 8. In some embodiments, the nucleic acid encoding a polypeptide having at least 98% or at least 80% sequence identity to amino acids 1-130 or 1-319, and terminating at a position corresponding to residue 131 or 320 of SEQ ID NO: 6, further comprises at least 80% sequence identity to a nucleotide sequence selected from the group consisting of SEQ ID NO: 1, 2, 3, 4, 5, 7, 8, 10, 11, 13, and 14.

Transgenic plant cells comprising nucleic acids encoding CAD polypeptides are also provided herein. For example, this document provides a transgenic plant cell comprising at least one exogenous nucleic acid. The exogenous nucleic acid comprises a regulatory region operably linked to a nucleic acid. The nucleic acid comprises a sequence encoding a CAD polypeptide or a sorghum CAD polypeptide having least 98% or at least 80% sequence identity to amino acids 1-130 or 1-319 and terminating at a position corresponding to residue 131 or 320 of SEQ ID NO: 6. In some embodiments, a plant produced from the transgenic plant cell has a decrease in the level of CAD activity as compared to the corresponding level in a control plant that does not comprise the nucleic acid. In some embodiments, the plant produced from the transgenic plant cell exhibits a brown midrib phenotype as compared to a control plant that does not comprise the CAD encoding nucleic acid. In some embodiments, the plant produced from the transgenic plant cell has a decrease in the level of lignin as compared to the corresponding level in a control plant that does not comprise the CAD encoding nucleic acid.

Plants and tissues comprising transgenic plant cells are also provided herein. For example, this document provides a plant comprising a transgenic plant cell. The transgenic plant cell comprises at least one exogenous nucleic acid. The exogenous nucleic acid comprises a regulatory region operably linked to a nucleic acid. The nucleic acid comprises a sequence encoding a CAD polypeptide or a sorghum CAD polypeptide having least 98% or at least 80% sequence identity to amino acids 1-130 or 1-319 and terminating at a position corresponding to residue 131 or 320 of SEQ ID NO: 6. In some embodiments, a plant produced from the transgenic plant cell has a decrease in the level of CAD activity as compared to the corresponding level in a control plant that does not comprise the nucleic acid. This document also provides biomass or seed comprising tissue from plants which comprise the transgenic plant cells.

Methods for producing plants comprising CAD encoding nucleic acids are provided herein. For example, in one aspect, a method comprises growing a transgenic plant cell comprising an exogenous nucleic acid. The nucleic acid comprises a sequence encoding a CAD polypeptide having at least 98% sequence identity to amino acids 1-130 or 1-319 of SEQ ID NO: 6 and terminating at a position corresponding to residue 131 or 320 of SEQ ID NO: 6. In another aspect, a method comprises growing a transgenic plant cell comprising an exogenous nucleic acid encoding a *sorghum* CAD polypeptide. The *sorghum* CAD polypeptide comprises at least 80% sequence identity to amino acids 1-130 or 1-319 of SEQ ID NO: 6 and terminates corresponding to residue 131 or 320 of SEQ ID NO: 6.

Methods for characterizing a *sorghum* plant are provided herein. For example, in one aspect, a method comprises detecting a nucleic acid encoding a CAD polypeptide in the *sorghum* plant. The CAD polypeptide has at least 80% sequence identity to amino acids 1-130 or 1-319 of SEQ ID NO: 6 and terminates corresponding to residue 131 or 320 of SEQ ID NO: 6. The nucleic acid can have a thymine corresponding to position 2794 of SEQ ID NO:2, position 2800 of SEQ ID NO: 4, 7, 10, or 13, position 4083 SEQ ID NO: 2, position 4089 of SEQ ID NOs: 4 or 7, position 4090 of SEQ ID NO: 10, position 497 of SEQ ID NO: 1, position 394 of SEQ ID NOs: 3, 5, 8, 11, or 14, position 1064 of SEQ ID NO:1, position 962 of SEQ ID NO:11, or position 961 of SEQ ID NOs: 3, 5, or 8.

This document provides methods of determining the presence of a polynucleotide in a *sorghum* plant. For example, in one aspect, a method comprises contacting at least one probe or primer pair with nucleic acid from the *sorghum* plant. The probe or primer pair is specific for a polynucleotide that encodes a CAD polypeptide. The CAD polypeptide has at least 80% sequence identity to amino acids 1-130 or 1-319 of SEQ ID NO: 6 and terminates at a position corresponding to residue 131 or 320 of SEQ ID NO: 6. The method also comprises determining whether or not the polynucleotide is present in the *sorghum* plant. The probe can be an oligonucleotide, e.g., an oligonucleotide comprising a nucleotide sequence selected from the group consisting of SEQ ID NOs: 34 and 36.

Kits for genotyping a *sorghum* biological sample are provided herein. For example, this document provides a kit comprising a primer pair that specifically amplifies, or a probe that specifically hybridizes to, a polynucleotide that encodes a CAD polypeptide. The CAD polypeptide comprises at least 80% sequence identity to amino acids 1-130 or 1-319 of SEQ ID NO: 6 and terminates at a position corresponding to residues 131 or 320 of SEQ ID NO: 6. In some embodiments, a kit comprises at least one primer of the primer pair or probe having specificity for a thymine corresponding to position 2794 of SEQ ID NO:2, position 2800 of SEQ ID NO: 4, 7, 10, or 13, position 4083 SEQ ID NO: 2, position 4089 of SEQ ID NOs: 4 or 7, position 4090 of SEQ ID NO: 10, position 497 of SEQ ID NO: 1, position 394 of SEQ ID NOs: 3, 5, 8, 11, or 14, position 1064 of SEQ ID NO:1, position 962 of SEQ ID NO:11, or position 961 of SEQ ID NOs: 3, 5, or 8. In some embodiments, a kit comprises at least one primer or probe comprising a nucleotide sequence selected from the group consisting of SEQ ID NO: 34 and 36.

Methods of breeding *sorghum* plants comprising CAD encoding nucleic acids are provided herein. In one aspect, the method comprises crossing two or more *sorghum* plants to produce progeny plants. At least one *sorghum* plant comprises at least one CAD allele encoding a CAD polypeptide having at least 80% sequence identity to amino acids 1-130 or 1-319 of SEQ ID NO: 6, and terminating corresponding to position 131 or 320 of SEQ ID NO: 6. The progeny plants can have at least one allele at a COMT locus that encodes a truncated COMT polypeptide. The method can also comprise identifying one or more of the progeny plants that comprise the at least one CAD allele. The at least one progeny plant can be homozygous for the CAD allele. The method can comprise identifying the CAD allele by a thymine corresponding to position 2794 of SEQ ID NO:2, position 2800 of SEQ ID NO: 4, 7, 10, or 13, position 4083 SEQ ID NO: 2, position 4089 of SEQ ID NOs: 4 or 7, position 4090 of SEQ ID NO: 10, position 497 of SEQ ID NO: 1, position 394 of SEQ ID NOs: 3, 5, 8, 11, or 14, position 1064 of SEQ ID NO:1, position 962 of SEQ ID NO:11, or position 961 of SEQ ID NOs: 3, 5, or 8. In another aspect, the method involves identification with at least one oligonucleotide specific for the CAD allele, e.g., an oligonucleotide comprising a nucleotide sequence set forth in SEQ ID NOs: 34 or 36. The method can also comprise using one or more of the identified progeny plants in a next generation of plant breeding.

A method of introducing a desired trait into a *sorghum* cultivar by marker assisted backcrossing is provided herein. For example, the method can comprise identifying a first *sorghum* plant having at least one CAD allele that encodes a CAD polypeptide. The CAD polypeptide comprises at least 80% sequence identity to amino acids 1-130 or 1-319 of SEQ ID NO: 6 and terminating at a position corresponding to residue 131 or 320 of SEQ ID NO: 6. The method can also comprise crossing the first *sorghum* plant with a second, genetically distinct *sorghum* plant having a desired trait, to produce progeny plants. The desired trait is not a phenotype conferred by the CAD allele. The method can also comprise selecting one or more progeny plants that have the desired trait and have a marker associated with the CAD allele, to produce selected progeny plants. The associated marker can comprise a thymine corresponding to position 2794 of SEQ ID NO:2, position 2800 of SEQ ID NO: 4, 7, 10, or 13, position 4083 SEQ ID NO: 2, position 4089 of SEQ ID NOs: 4 or 7, position 4090 of SEQ ID NO: 10, position 497 of SEQ ID NO: 1, position 394 of SEQ ID NOs: 3, 5, 8, 11, or 14, position 1064 of SEQ ID NO:1, position 962 of SEQ ID NO:11, or position 961 of SEQ ID NOs: 3, 5, or 8. The selected progeny plants can be backcrossed with the first or second plants to produce backcross progeny plants, and selected for backcross progeny plants that have the desired trait and the marker. The backcross progeny plants can have more than one marker associated with the CAD allele, or can be homozygous for the CAD allele. Selection can also be carried out for a marker associated with the desired trait. Backcrossing and selection can be repeated at least three times to produce $BC_4$ or higher backcross progeny plants that have the desired trait and the at least one CAD allele. Such progeny plants can also have the at least one allele at the COMT locus that encodes a truncated COMT polypeptide. In another aspect, a method of introducing a desired trait into a *sorghum* cultivar comprises identifying the CAD allele with an oligonucleotide specific for the CAD allele. For example, the oligonucleotide can comprise a nucleotide sequence selected from the group consisting of SEQ ID NOs: 34 and 36.

Methods of modulating plant composition are provided herein. For example, in one aspect, a method comprises introducing into a plant cell an exogenous nucleic acid encoding a *sorghum* CAD polypeptide. The *sorghum* CAD polypeptide has at least 80% sequence identity to amino acids 1-130 and 1-319 of SEQ ID NO: 6 and terminates corresponding to position 131 or 320 of SEQ ID NO: 6. The composition of a plant produced from the plant cell is modulated as compared to the composition of a control plant that does not comprise the nucleic acid, e.g., decreased lignin content, increased glucan content, increased cellulose content, or increased hemicellulose content.

Plants of an agronomically elite *sorghum* variety are provided herein. For example, this document provides plants that are homozygous at a CAD locus for an allele encoding a truncated CAD polypeptide. In another embodiment, the plants are homozygous at a COMT locus for an allele that encodes a truncated COMT polypeptide. The plants can be male sterile or female sterile.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Figure 1A:
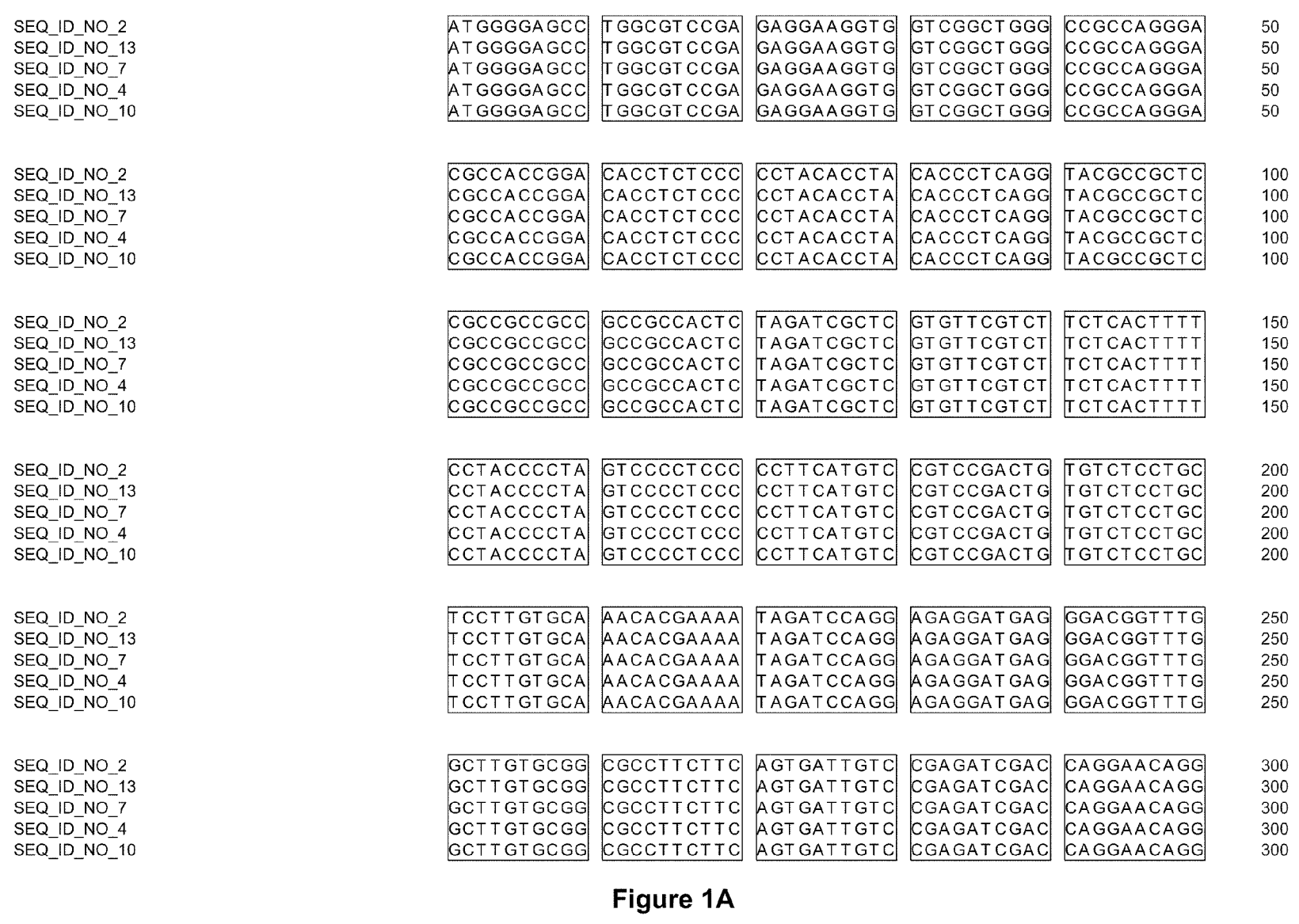
Figure 1B:
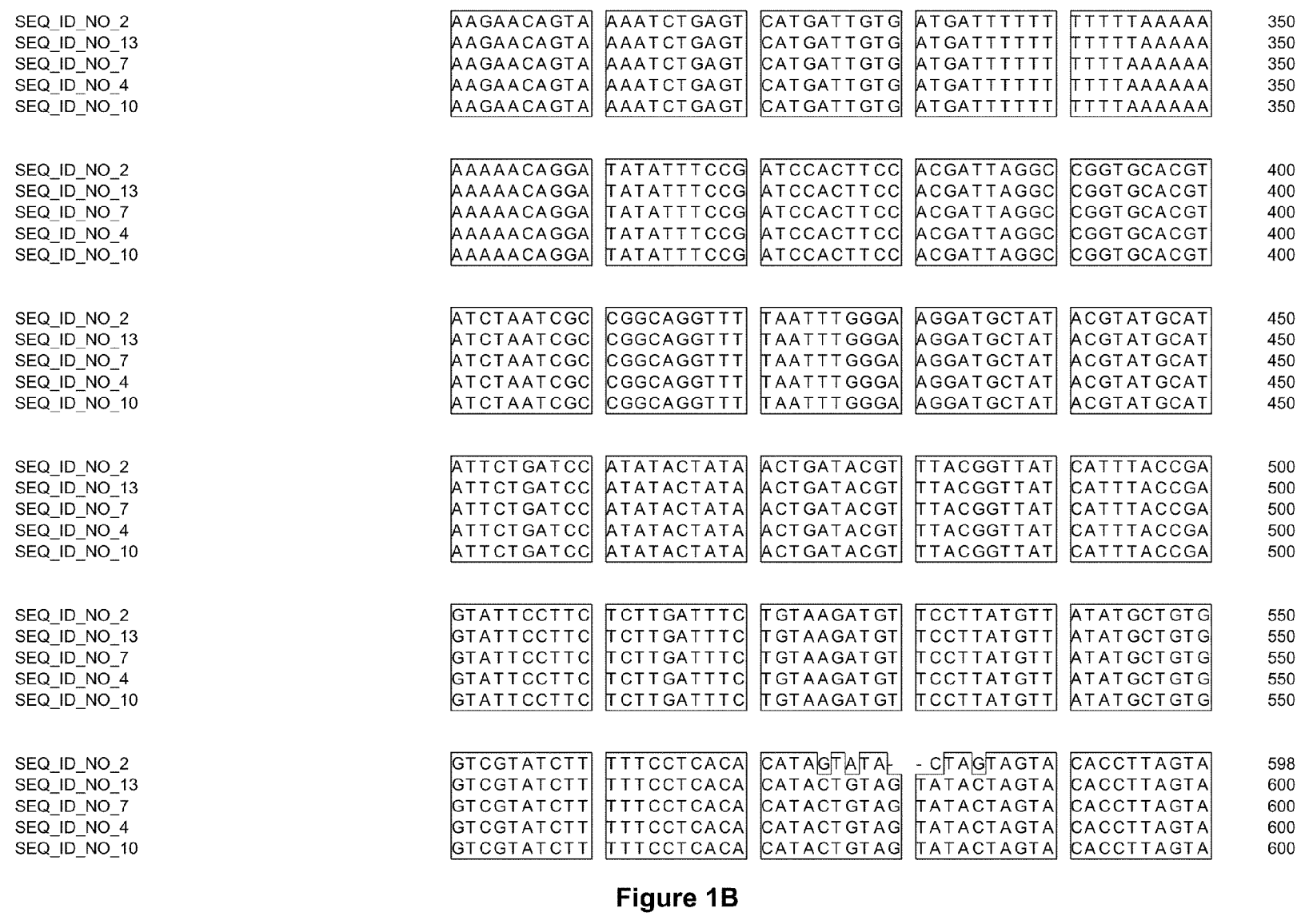
Figure 1D:
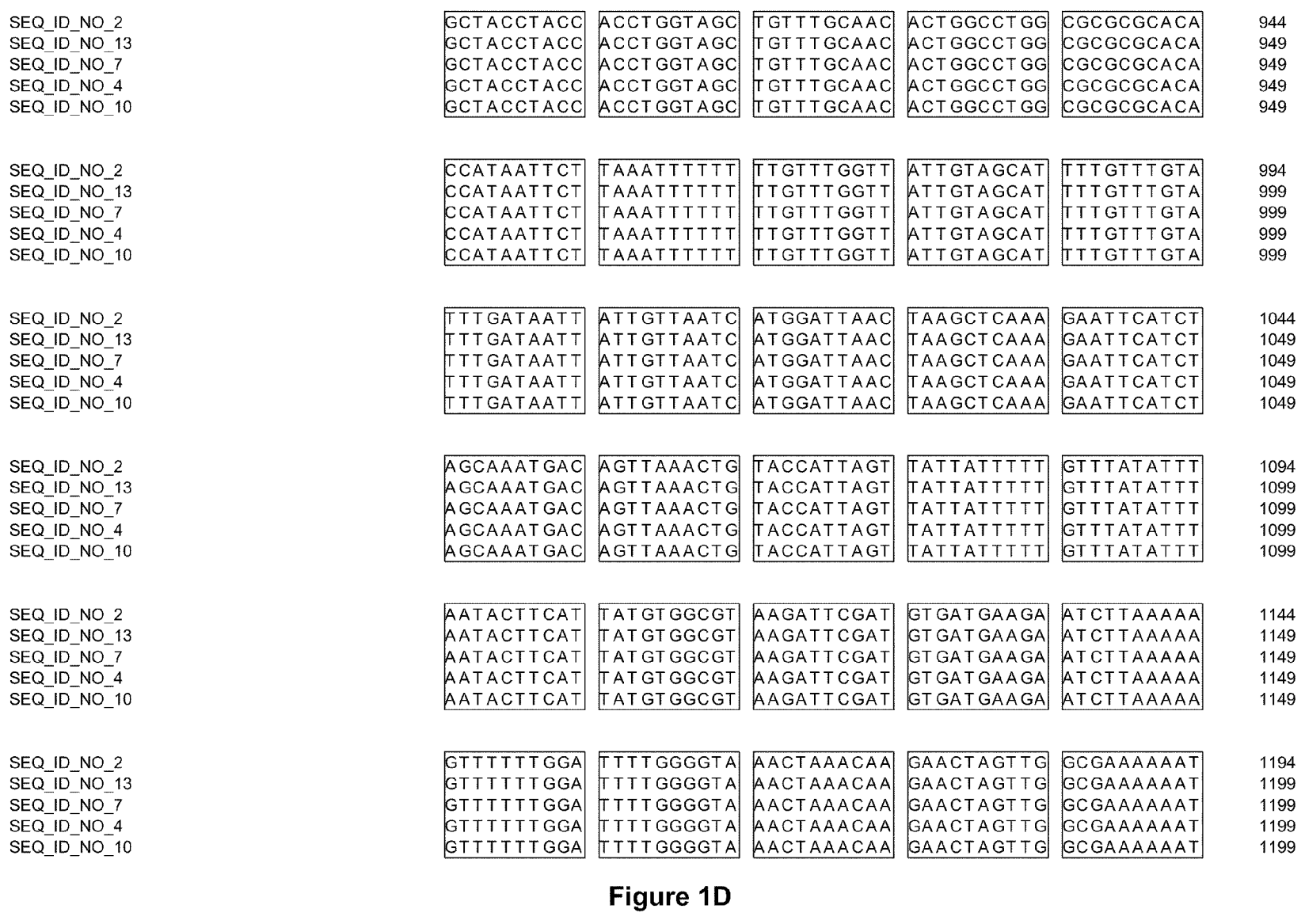
Figure 1E:
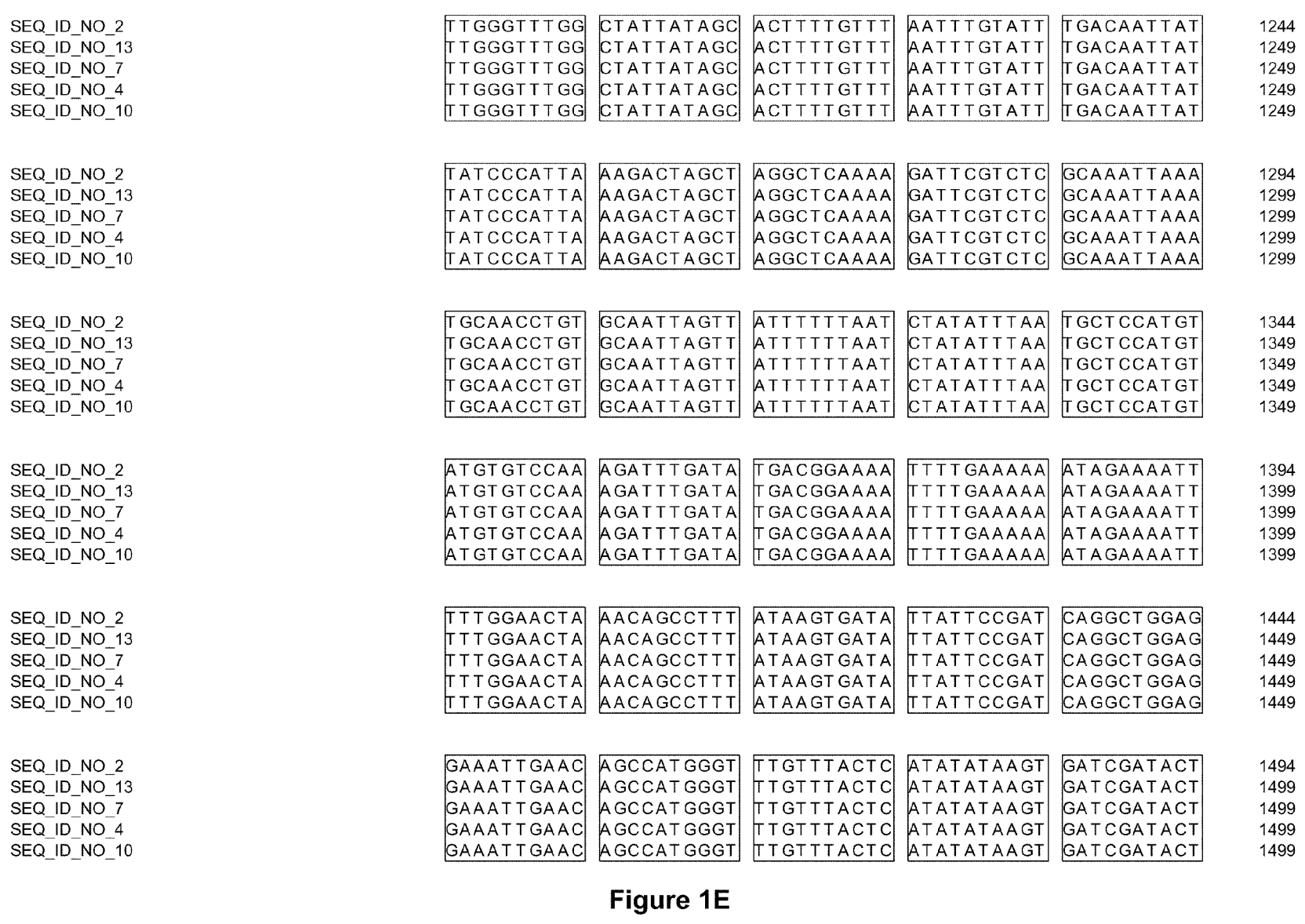
Figure 1G:
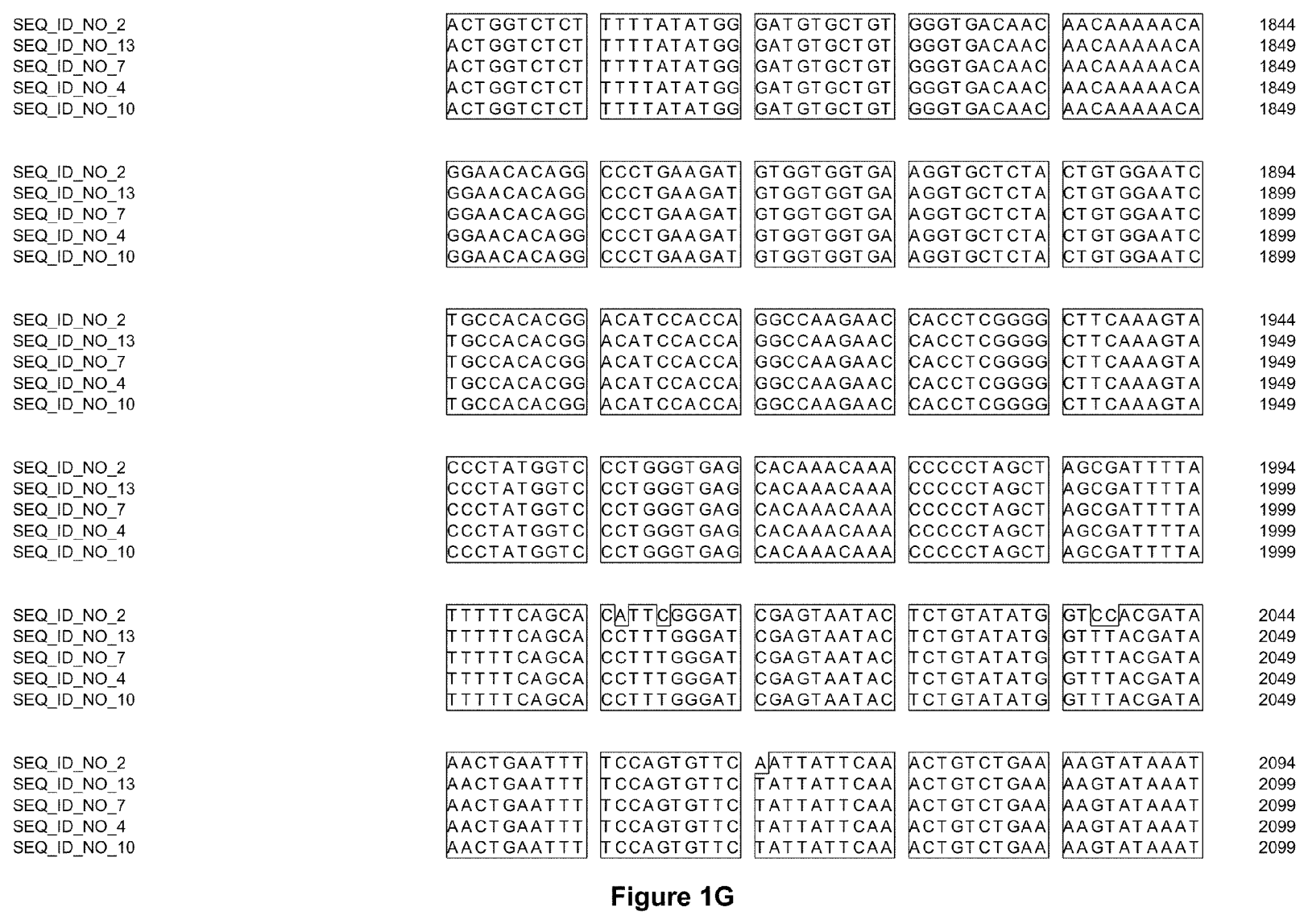
Figure 1H:
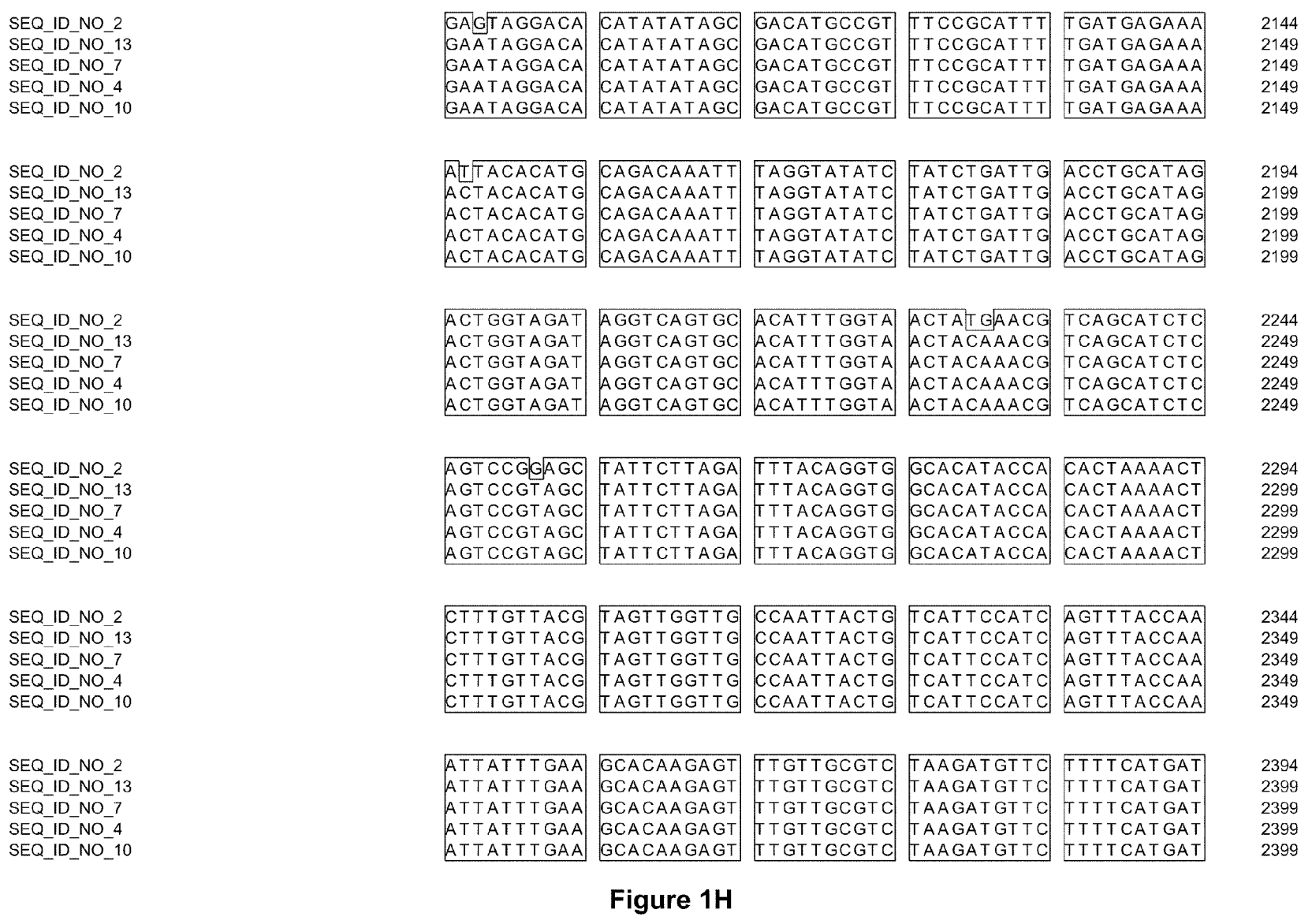
Figure 1M:
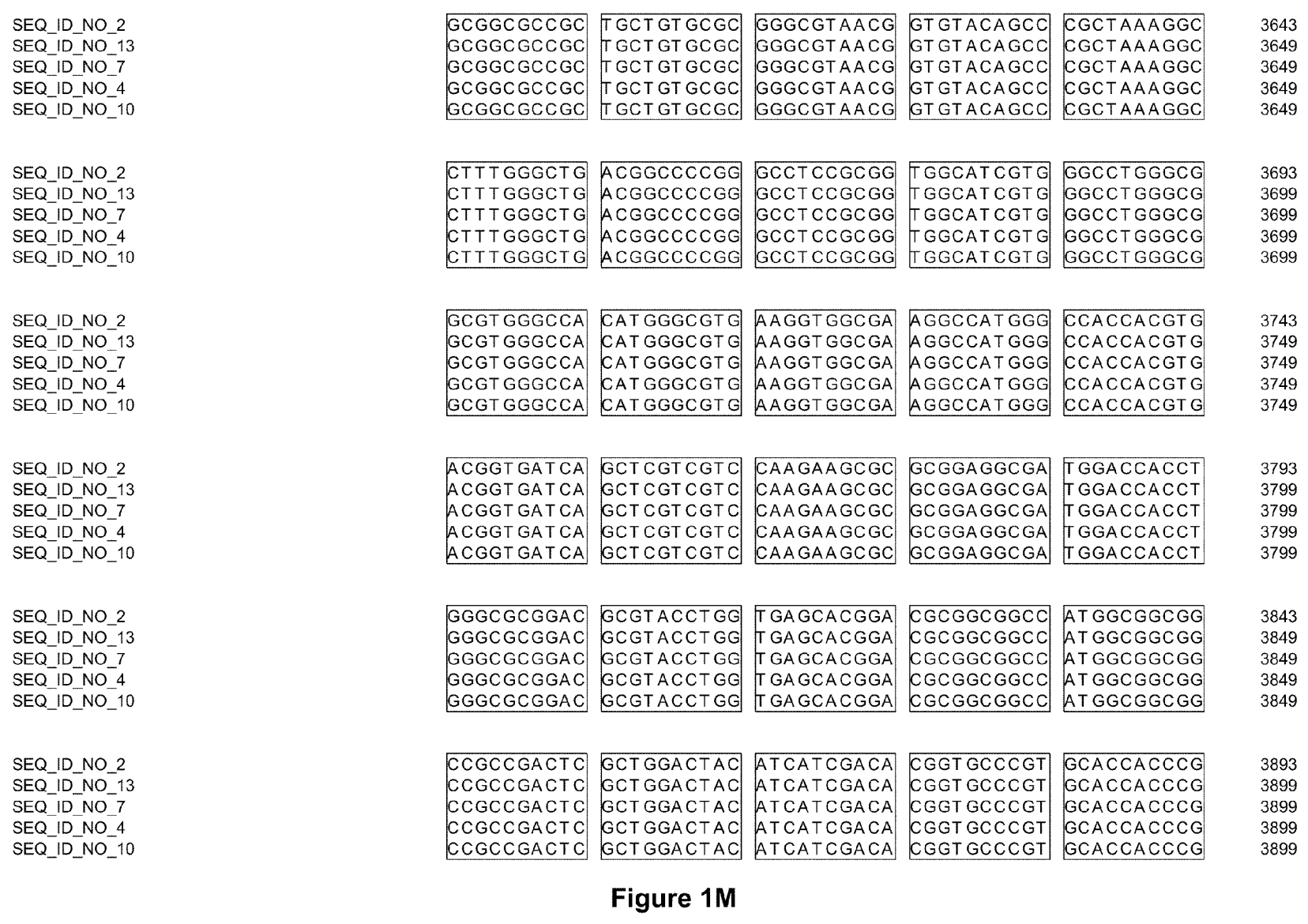

FIG. 1(A-O) is an alignment of *sorghum* CAD genomic nucleotide sequences for alleles corresponding to full length CAD (SEQ ID NO:2 from Ceres germplasm ID No.: PI599692-81733680; and SEQ ID NO:4 from Ceres germplasm ID No.: 22043-81733671, a truncated CAD of 320 amino acids (SEQ ID NO:7 from Ceres germplasm ID No.: PI602730-81733686), truncated CAD of 131 amino acids (SEQ ID NO:13 from Ceres germplasm ID No.: PI535790-81733677), and CAD having frameshift insertion mutation at position 4016 (SEQ ID NO:10 from Ceres germplasm ID No.: BICOLOR-81733675). In all the alignment figures shown herein, a dash in an aligned sequence represents a gap, i.e., a lack of a nucleotide at that position. Identical nucleotides among aligned sequences are identified by boxes. FIG. 1 and the other alignment figure provided herein were generated using the program MUSCLE version 3.52.

FIG. 2(A-F) is an alignment of *sorghum* CAD cDNA sequences for alleles corresponding to full length CAD (SEQ ID NO:1 from GI No. 119852230; SEQ ID NO:3 from Ceres germplasm ID No.: PI599692-81733680; SEQ ID NO:5 from Ceres germplasm ID No.: 22043-81733671; truncated CAD of 320 amino acids (SEQ ID NO:8 from Ceres germplasm ID No.: PI602730-81733686), truncated CAD of 131 amino acids (SEQ ID NO:14 from Ceres germplasm ID No.: PI535790-81733677), and a CAD having a frameshift insertion mutation at position 890 (SEQ ID NO:11 from Ceres germplasm ID No.: BICOLOR-81733675).

DETAILED DESCRIPTION

The brown midrib (BMR) trait results in reduced lignification, reduced cell-wall concentration, increased digestibility and increased voluntary intake of feed by ruminants (Casler et al., 2003). In *sorghum*, BMR phenotypes are typical of some mutants of the CAD and COMT genes. There are at least 28 BMR mutants in *sorghum*, some being spontaneous mutations and others induced by mutagenesis. In addition to the brown vascular tissue pigmentation of the leaf midribs and stems, these BMR mutants often exhibit decreased lignin content in stems and leaves in comparison to wild types or cultivars lacking a BMR phenotype, as CAD and COMT contribute to the lignin biosynthesis pathway. BMR plants have lignin that is less polymerized and contains less phenolic monomers that can affect digestion. Suzuki et al. analyzed stem samples from BMR *sorghum* phenotypes and found increased levels of 5-hydroxy-guaiacyl residues in the cell walls, in comparison to wild types or cultivars lacking a BMR phenotype (Suzuki et al., 1997). Porter et al. describes phenotypes for several *sorghum* BMR mutations (Porter et al., 1978). For example, the content of acid detergent fiber, lignin cellulose, hemicellulose, percent cell wall constituent and in vitro cell wall constituent disappearance in stems and leaves for BMR-6 and BMR-17 mutations in comparison to normal plants.

I. DEFINITIONS

An "allele" is any of one or more alternative forms of a gene. In a diploid cell or organism, the two alleles of a given gene occupy corresponding loci on a pair of homologous chromosomes.

"Amino acid" refers to one of the twenty biologically occurring amino acids and to synthetic amino acids, including D/L optical isomers.

"Biomass" refers to harvestable above ground vegetative matter of plants, typically a mixture of leaves, stems, and reproductive structures. Vegetative matter may be comprised of only leaves or only stems in some instances, and is considered to be biomass. Seeds are not considered vegetative matter and, therefore, compositions that contain primarily only seeds are not considered to be biomass, although it will be appreciated that biomass may contain seeds as part of the mixture. Biomass can be quantified as dry matter yield, which is the mass of biomass produced (usually reported in T/acre) if the contribution of water is subtracted from the fresh mater weight. Dry matter yield (DMY) yield is calculated using the fresh matter weight (FMW) and a measurement of weight percent moisture (M) in the following equation. DMY= ((100−M)/100)*FMW. Biomass can be quantified as fresh matter yield, which is the mass of biomass produced (usually reported in T/acre) on an as-received basis, which includes the weight of moisture.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Locus" refers a position on a chromosome, for example, the region of a chromosome at which a particular gene is located. In a diploid organism, the allele at a particular gene locus on one chromosome may be an allele that is different from the allele at that locus on the homologous chromosome, in which case the organism is considered heterozygous for that locus. If the alleles at a particular locus are the same, the organism is considered homozygous for that locus.

"Modulation" of the level of chemical composition, phenotype, or enzyme activity refers to the change in the level that is observed as a result of expression of, or transcription from, an exogenous nucleic acid in a plant cell. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have various three-dimensional structures. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

A "probe" is a molecule capable of distinguishing among polymorphisms in the genome of an organism. For example, a nucleic acid to which is attached a conventional detectable label or reporter molecule, e.g., a radioactive isotope, ligand, chemiluminescent agent, fluorescent agent, or enzyme can be a probe. Such a probe can be complementary to a strand of a target nucleic acid, such as to a strand of genomic DNA from *sorghum* having a truncated CAD, whether from a *sorghum* plant or from a sample that includes DNA from a *sorghum* plant. Probes include not only deoxyribonucleic or ribonucleic acids but also polyamides and other probe materials that bind specifically to a target DNA sequence and can be used to detect the presence of that target DNA sequence. Hybridization of probes with target DNA can be detected by several methods including polymerase chain reaction (PCR)

based assays, electrophoresis-based assays, or the molecular beacon or dynamic allele-specific hybridization (DASH) assays.

"Primers" are nucleic acids, typically oligonucleotides, that can anneal to a complementary or substantially complimentary target DNA strand to form a hybrid between the primer and the target DNA strand, then can be extended along the target DNA strand by a polymerase. Primer pairs of the present invention can be used for amplification of a specific nucleic acid, e.g., by PCR or other conventional nucleic acid amplification methods.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., The Plant Cell, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. POLYPEPTIDES

Polypeptides described herein include C-terminus truncated CAD polypeptides. Such polypeptides can be lignin-modulating polypeptides. Lignin-modulating polypeptides can be effective to modulate lignin levels when expressed in a plant or plant cell. Such polypeptides typically contain at least one domain indicative of lignin-modulating polypeptides, as described in more detail herein. In some embodiments, lignin-modulating polypeptides have greater than 90% identity to SEQ ID NOs: 6, 9, 12, 15, 18, 21, 24, 27, 30, or 33, as described in more detail herein.

In some embodiments, lignin-modulating polypeptides such as a C-terminus truncated *sorghum* CAD polypeptide can be about 100, 110, 120, 130, 140, 150, 160, 170, 180, 190, 200, 210, 220, 230, 240, 250, 260, 270, 280, 290, 300, 310, 320, 330, 340, or 350 amino acids in length. In some embodiments, lignin-modulating polypeptides such as C-terminus truncated CADs can be 131 or 320 amino acids in length. In some embodiments the truncated CADs are from *sorghum*.

A. Domains Indicative of Truncated CAD Polypeptides

A lignin-modulating polypeptide can contain an Alcohol dehydrogenase GroES-like domain (ADH N), a methyltransferase small domain (MTS), and/or a Zinc-binding dehydrogenase (ADH zinc N), which is predicted to be characteristic of a CAD enzyme. In some embodiments, a C-terminus truncated CAD described herein comprises all or a substantial portion of an ADH N domain. In some embodiments, the C-terminus truncated CAD described herein comprises an ADH N domain and a portion of an ADH zinc N domain. SEQ ID NO: 9 sets forth the amino acid sequence of a truncated CAD clone, identified herein as PI602730-81733686, that is predicted to encode a polypeptide containing a portion of an ADH zinc N domain and ADH N and MTS domains. SEQ ID NO: 15 sets forth the amino acid sequence of a *sorghum* clone, identified herein as PI535790-81733677, that is predicted to encode a polypeptide containing a portion of a ADH N domain.

In some embodiments, the truncated CAD described herein is a naturally occurring polypeptide. In other embodiments, the truncated CAD described herein is synthetic. For example, an allelic variant of a *sorghum* CAD can be identified by BLASTing or designing primers that recognize conserved regions of the gene and amplifying said gene and then synthesizing a nucleic acid that encodes truncated CAD. In other embodiments, site directed mutagenesis may be used to generate desired truncations. A truncated polypeptide may retain certain domains of the naturally occurring polypeptide while lacking others. Thus, length variants that are up to about 2, 5, 10, 20, 30, 40, 50, 60, 70, 80 90, 100, 125, 150, 175, 200, 225 or 300 amino acids shorter or longer than a naturally occurring CAD typically exhibit the lignin-modulating activity of a truncated polypeptide. In some embodiments, a truncated CAD comprises about 10, 15, 20, 25, 30, 35, 40, 45, 50, 55, 60, 65, 70, 75, 80, 85, 90, or 95 amino acids of an ADH N domain. In some embodiments, a truncated CAD comprises about 10, 15, 20, 25, 30, 35, 40, 45, 50, 55, 60, 65, 70, 75, 80, 85, 90, 95, 100, 110, or 120 amino acids of an ADH zinc N domain. In some embodiments, a truncated polypeptide is a dominant negative polypeptide. SEQ ID NO: 9 and 15 sets forth the amino sequence of a lignin-modulating polypeptide that is truncated at the C-terminus end relative to a full length *sorghum* CAD polypeptide. Expression in a plant of such a truncated polypeptide confers a difference in the level of lignin in a tissue of the plant as compared to the corresponding level in tissue of a control plant that does not comprise the truncation.

B. Functional Alleles of Truncated CADs

In some embodiments, one or more functional homologs of a reference lignin-modulating polypeptide defined by one or more of the Pfam descriptions indicated above are suitable for use as lignin-modulating polypeptides or truncations thereof. A functional homolog is a polypeptide that has sequence similarity to a reference truncated CAD polypeptide, and that exhibits a brown midrib phenotype. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a lignin-modulating polypeptide, or by combining domains from the coding sequences for different naturally-occurring lignin-modulating polypeptides ("domain swapping"). The term "functional homolog" is sometimes applied to the nucleic acid that encodes a functionally homologous polypeptide. In some embodiments, a nucleic acid encoding a truncated CAD may be synthesized.

Functional homologs and potential allelic variants can be identified by analysis of nucleotide and polypeptide sequence alignments. For example, performing a query on a database of nucleotide or polypeptide sequences can identify homologs of lignin-modulating polypeptides. Sequence analysis can involve BLAST, Reciprocal BLAST, or PSI-BLAST analysis of nonredundant databases using a lignin-modulating polypeptide amino acid sequence as the reference sequence. Amino acid sequence is, in some instances, deduced from the nucleotide sequence. Those polypeptides in the database that have greater than 90% sequence identity are candidates for allelic variants of a lignin-modulating polypeptide which can be used to make truncations as described herein.

Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in lignin-modulating polypeptides, e.g., conserved functional domains.

Conserved regions can be identified by locating a region within the primary amino acid sequence of a lignin-modulating polypeptide that is a repeated sequence, forms some secondary structure (e.g., alpha helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate. Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity. For example, a truncated CAD may have a conserved ADH domain as compared to CAD amino acid sequences from other species.

Examples of amino acid sequences of allelic variants of the polypeptide set forth in SEQ ID NO: 6 are provided in the Sequence Listing. Such allelic variants include PI602730-81733686 (SEQ ID NO: 9) and PI535790-81733677 (SEQ ID NO: 15). In some cases, an allelic variant of SEQ ID NO: 6 has an amino acid sequence with at least 80% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 6, 9, 12, or 15. In some embodiments, an allelic variant of SEQ ID NO: 6 or 12 is truncated by about 5, 10, 25, 50, 75, 100, 125, 150, 175, 200, 225, 250, 275, or 300 amino acids in length. In some embodiments, the allelic variants are from *sorghum*.

The identification of conserved regions in a truncated lignin-modulating polypeptide facilitates production of variants of truncated lignin-modulating polypeptides. Variants of truncated lignin-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments of nucleic acids set forth in FIG. 1 or FIG. 2 and/or alleles identified in the Sequence Listing. Such a polypeptide includes the conserved regions, arranged in the order from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

Figure 2B:
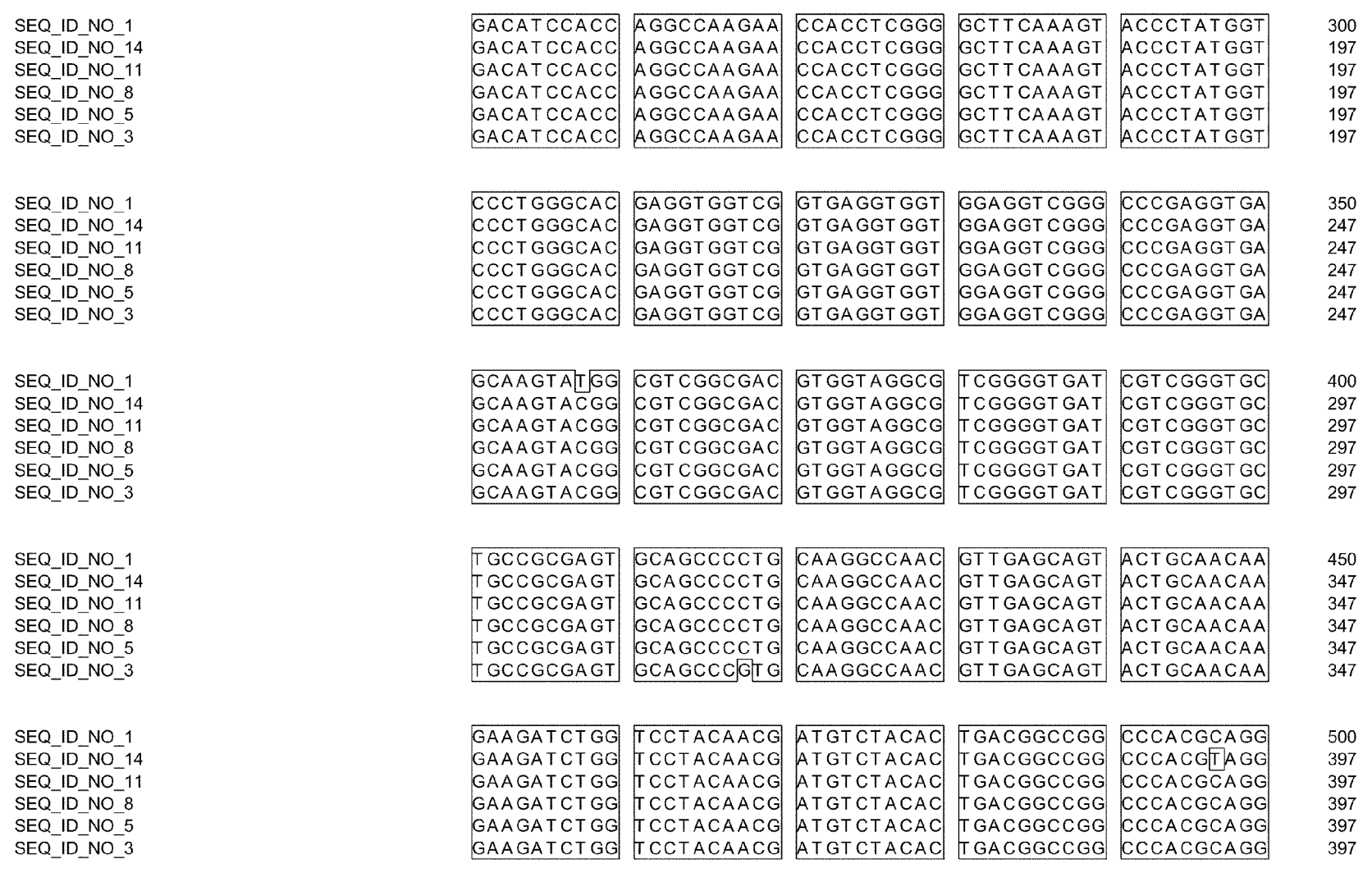
Figure 2C:
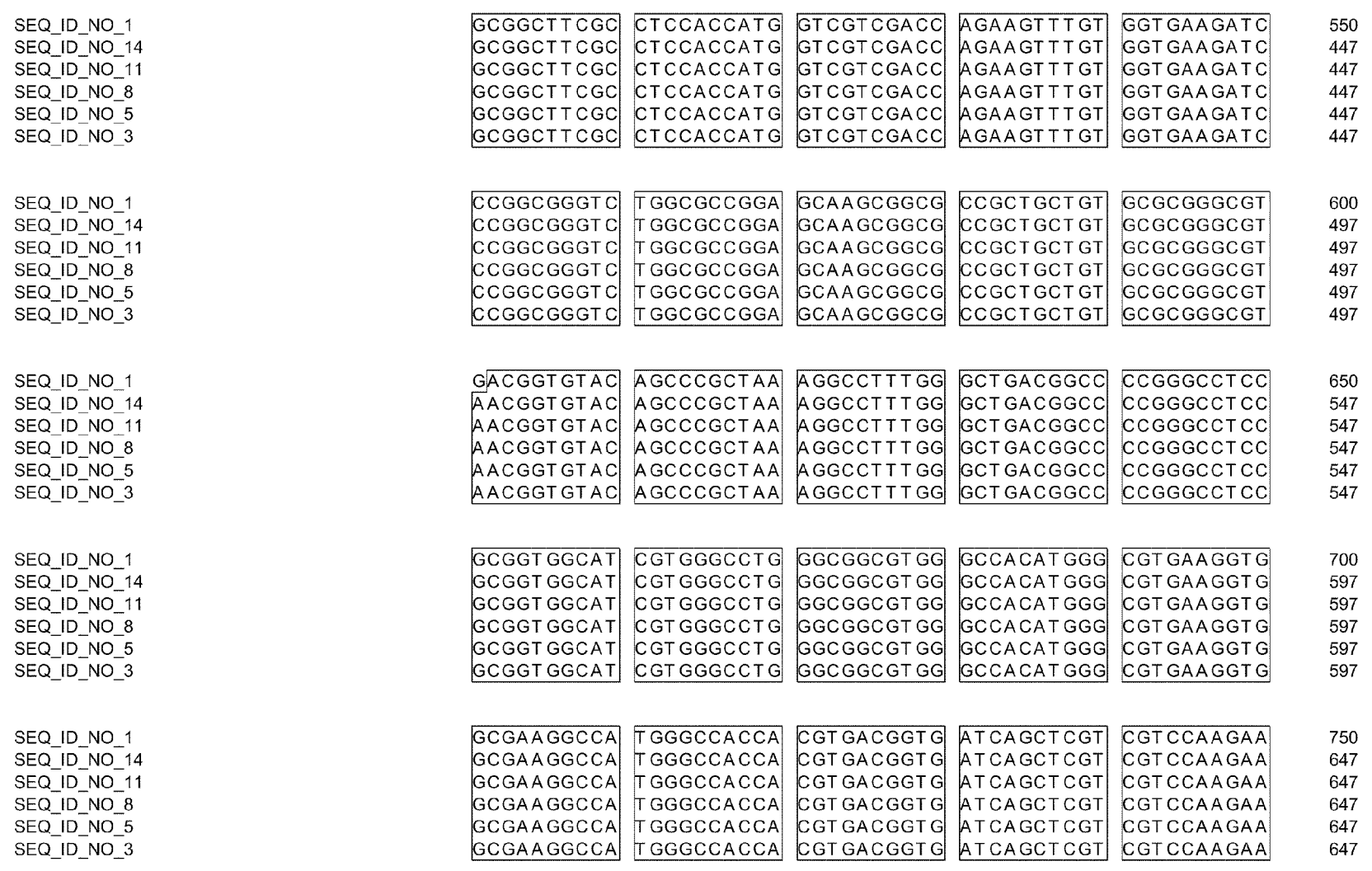
Figure 2E:
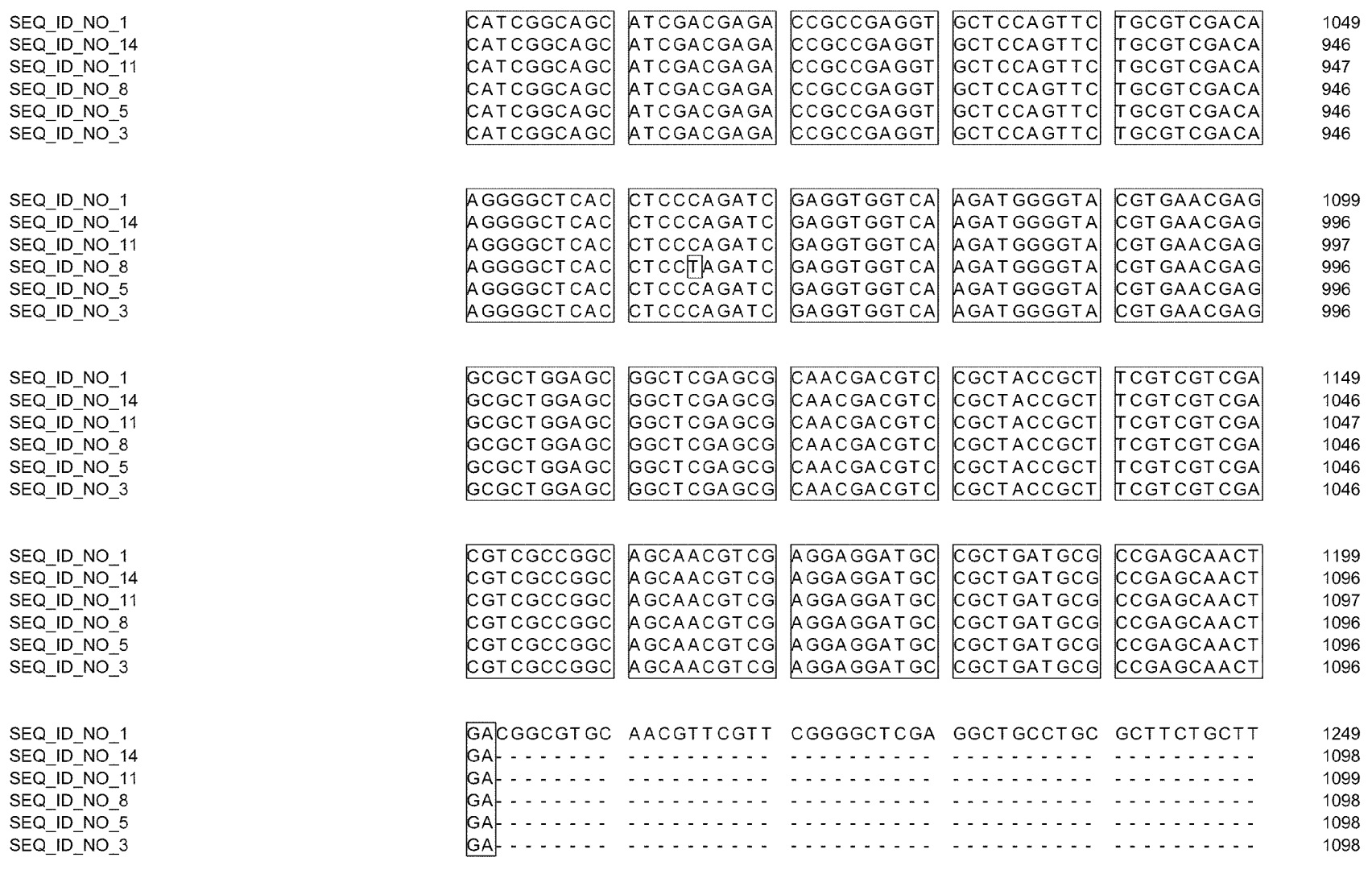

Truncations of CAD homologs or *sorghum* allelic variants of CAD are also described herein. For example, CAD homologs or *sorghum* allelic variants of CAD can be truncated artificially or naturally occurring truncations can be identified which are truncated such that the length of the resulting polypeptide corresponds to the length of the polypeptide of SEQ ID NOs: 9 or 15. Polypeptide sequences of CAD homologs or *sorghum* allelic variants of CAD can be aligned with the truncated CAD sequences of SEQ ID NOs: 9 and/or 15 using, for example, a Clustal program such as ClustalW 1.83. Alternatively, the nucleotide sequences encoding CAD homologs or *sorghum* allelic variants of CAD can be aligned with the truncated nucleotide sequences of SEQ ID NOs: 7 and/or 13 (genomic DNA), or 8 and/or 14 (cDNA) using a Clustal program. The alignments of polypeptides or nucleotides can then be used to determine the corresponding position at which a truncated sequence can terminate. For example in FIG. 1, sequences aligned with SEQ ID NO: 13 that terminate with the nucleotide in the alignment that aligns with position 2802 of SEQ ID NO: 13 are corresponding truncations. In FIG. 1, for example, sequences aligned with SEQ ID NO: 7 that terminate with the nucleotide in the alignment that aligns with position 4091 of SEQ ID NO: 7 are corresponding truncations. In FIG. 2, for example, sequences aligned with SEQ ID NO: 14 that terminate with the nucleotide in the alignment that aligns with position 396 of SEQ ID NO: 14 are corresponding truncations. In FIG. 2, for example, sequences aligned with SEQ ID NO: 8 that terminate with the nucleotide in the alignment that aligns with position 964 of SEQ ID NO: 8 are corresponding truncations.

Various methods for measuring the level of CAD or the activity of CAD are known in the art. In the lignin biosynthesis pathway, CAD is known to be involved in several reduction reactions, including, but not limited to, the reduction of p-Coumaraldehyde to p-Coumaryl alcohol, Caffeyl aldehyde to Caffeyl alcohol, Coniferldahyde to Coniferyl alcohol, and Sinapaldehyde to Sinapyl alcohol. For example, in vitro, substrates can be labeled, using carbon or other means, and CAD from a plant sample or a plant extract comprising CAD can be added to the substrate to be reduced. The amount of label in the product can be used to compare the level of CAD activity among samples.

The composition of each plant sample, including, but not limited to, lignin, glucose, arabinose, fructose, galactose, xylose, cellulose, hemicellulose, 5-hydroxy-guaiacyl, neutral detergent fiber, acid detergent fiber, or acid detergent lignin can be measured by independent analytical chemistry techniques known in the art, typically wet chemical techniques. For example, following pre-treatment by acid, enzymes, or other means, plant samples can be analyzed for glucose using a YSI 2700D Dual-Channel Biochemistry Analyzer (YSI Life Sciences, Yellow Springs, Ohio). Glucan, xylan, arabinan, and lignin contents of a plant or plant part can be determined by ASTM methods E1758-01 (Determination of Biomass Sugars by High Performance Liquid Chromatography) and/or E1721-01 (Determination of Acid Insoluble Residue (Lignin) in Biomass).

C. Percent Identity

In some embodiments, a lignin-modulating polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 6, 9, 12, 15, 18, 21, 24, 27, 30, or 33. Polypeptides having such a percent sequence identity often have a domain indicative of a lignin-modulating polypeptide as discussed above. Amino acid sequences of lignin-modulating polypeptides having at least 80% sequence identity to one of the amino acid sequences set forth in SEQ ID NOs: 6, 9, 12, 15, 18, 21, 24, 27, 30, or 33 can be identified by BLAST as described herein.

"Percent sequence identity" refers to the degree of sequence identity between a reference sequence, e.g., SEQ ID NO:9, and a candidate sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for a candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. In some embodiments, the percent identity is based on the alignment over the length of the shorter sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a lignin-modulating polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 6, 9, 12, 15, 18, 21, 24, 27, 30, or 33. Amino acid sequences of polypeptides having greater than 80% sequence identity to the polypeptide set forth in SEQ ID NO:6 are provided in the Sequence Listing. Truncations of a lignin-modulating polypeptides may have a length that is from 10 percent to 90 percent of the length of the reference sequence, e.g., 10, 20, 30, 40, 50, 60, 70, 80, 90, or 95 percent of the length of the reference sequence.

D. Other Sequences

It should be appreciated that a lignin-modulating polypeptide can include additional amino acids that are not directly involved in lignin modulation, and thus such a polypeptide can be longer than would otherwise be the case. For example, a lignin-modulating polypeptide can include a purification tag, a chloroplast transit peptide, a mitochondrial transit peptide, an amyloplast peptide, or a leader sequence added to the amino or carboxy terminus. In some embodiments, a lignin-modulating polypeptide includes an amino acid sequence that functions as a reporter, e.g., a green fluorescent protein or yellow fluorescent protein.

In some embodiments, the methods and compositions described herein comprise truncated COMT amino acid and nucleic acid sequences that modulate the lignin content of plants. Examples of such truncated COMT sequences include SEQ ID NOs: 21 or 27.

III. NUCLEIC ACIDS

Nucleic acids described herein include nucleic acids that are effective to modulate lignin levels when transcribed in a plant or plant cell. Such nucleic acids include, without limitation, those that encode a lignin-modulating polypeptide and those that can be used to inhibit expression of a lignin-modulating polypeptide via a nucleic acid based method.

A. Nucleic Acids Encoding Lignin-Modulating Polypeptides

Nucleic acids encoding lignin-modulating polypeptides are described herein. Such nucleic acids include those that are less than 80% (e.g., from 10% to less than 45, 50, 55, 60, 65, 70, 75, or 80%) of the length of the full-length nucleic acid set forth in SEQ ID NOs: 1, 2, 4, 10, 16, 22, 28, 31, 3, 5, 17, 23, 29, or 32. Examples of nucleic acids encoding lignin-modulating polypeptides include SEQ ID NOs: 7, 10, 13, 19, 25, 8, 11, 14, 20, and 26, as described in more detail below.

A lignin-modulating nucleic acid can comprise the nucleotide sequence set forth in SEQ ID NO: 7, 8, 10, 11, 13, 14, 19, 20, 25, or 26. Alternatively, a lignin-modulating nucleic acid can be a variant of the nucleic acid having the nucleotide sequence set forth in SEQ ID NO: 1, 2, 4, 7, 10, 13, 16, 19, 22, 25, 28, 31, 3, 5, 8, 11, 14, 17, 20, 23, 26, 29, or 32. For example, a lignin-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1, 2, 4, 7, 10, 13, 16, 19, 22, 25, 28, 31, 3, 5, 8, 11, 14, 17, 20, 23, 26, 29, or 32.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Lignin-Modulating Polypeptide A nucleic acid encoding one of the lignin-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular lignin-modulating polypeptide; i.e., for many amino acids, there is more than one nucleotide triplet that serves as the codon for the amino acid. Thus, codons in the coding sequence for a given lignin-modulating polypeptide can be modified such that optimal expression in a particular plant species is obtained, using appropriate codon bias tables for that species.

In some cases, expression of a lignin-modulating polypeptide inhibits one or more functions of an endogenous polypeptide. For example, a nucleic acid that encodes a dominant negative polypeptide can be used to inhibit protein function. A dominant negative polypeptide typically is truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058.

ii. Inhibition of Expression of a CAD or COMT Polypeptide

Polynucleotides and recombinant constructs described herein can be used to inhibit expression of a CAD or COMT polypeptide in a plant species of interest. See, e.g., Matzke and Birchler, Nature Reviews Genetics 6:24-35 (2005); Akashi et al., Nature Reviews Mol. Cell. Biology 6:413-422 (2005); Mittal, Nature Reviews Genetics 5:355-365 (2004); Dorsett and Tuschl, Nature Reviews Drug Discovery 3: 318-329 (2004); and Nature Reviews RNA interference collection, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding lignin-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., Proc. Natl. Acad. Sci. USA, 92(13): 6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a lignin-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the lignin-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a lignin-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the lignin-modulating polypeptide. In other embodiments, one strand of the stem portion of a double stranded RNA comprises a sequence that is similar or identical to the sequence of an intron, or a fragment thereof, in the pre-mRNA encoding a lignin-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a truncated lignin-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a lignin-modulating polypeptide, or a fragment of such sequences. In some embodiments, the sense or antisense sequence is identical or complementary to a sequence of the regulatory region that drives transcription of the gene encoding a lignin-modulating polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a lignin-modulating polypeptide described herein. The sense sequence complementary to the antisense sequence can be a sequence present within the mRNA of the lignin-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., Plant Physiol., 141:1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

C. Constructs/Vectors

Recombinant constructs provided herein can be used to transform plants or plant cells in order to modulate lignin levels. A recombinant nucleic acid construct can comprise a nucleic acid encoding a lignin-modulating polypeptide as described herein, operably linked to a regulatory region suitable for expressing the lignin-modulating polypeptide in the plant or cell. Thus, a nucleic acid can comprise a coding sequence that encodes any of the lignin-modulating polypeptides as set forth in SEQ ID NOs: 9, 15, 21, or 27, or a variant thereof. Examples of nucleic acids encoding lignin-modulating polypeptides are set forth in SEQ ID NO:7, 8, 13, 14, 19, 20, 25, or 26. The lignin-modulating polypeptide encoded by a recombinant nucleic acid can be a native lignin-modulating polypeptide, or can be heterologous to the cell. In some cases, the recombinant construct contains a nucleic acid that inhibits expression of a lignin-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner. Some suitable regulatory regions initiate transcription only, or predominantly, in certain cell types.

Methods for identifying and characterizing regulatory regions in plant genomic DNA are known, including, for example, those described in the following references: Jordano et al., Plant Cell, 1:855-866 (1989); Bustos et al., Plant Cell, 1:839-854 (1989); Green et al., EMBO J., 7:4035-4044 (1988); Meier et al., Plant Cell, 3:309-316 (1991); and Zhang et al., Plant Physiology, 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; Ser Nos. 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOs-MEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., Proc. Natl. Acad. Sci. USA, 86:7890-7894 (1989)), root cell specific promoters reported by Conkling et al., Plant Physiol., 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., Plant Cell, 1(9):839-853 (1989)), the soybean trypsin inhibitor promoter (Riggs et al., Plant Cell, 1(6):609-621 (1989)), the ACP promoter (Baerson et al., Plant Mol. Biol., 22(2):255-267 (1993)), the stearoyl-ACP desaturase promoter (Slocombe et al., Plant Physiol., 104(4):167-176 (1994)), the soybean a' subunit of β-conglycinin promoter (Chen et al., Proc. Natl. Acad. Sci. USA, 83:8560-8564 (1986)), the oleosin promoter (Hong et al., Plant Mol. Biol., 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., Mol. Cell. Biol., 13:5829-5842 (1993)), the beta-amylase promoter, and the barley hordein promoter. Other maturing endosperm promoters include the YP0092, PT0676, and PT0708 promoters.

iv. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (Larix laricina), the pine cab6 promoter (Yamamoto et al., Plant Cell Physiol., 35:773-778 (1994)), the Cab-1 promoter from wheat (Fejes et al., Plant Mol. Biol., 15:921-932 (1990)), the CAB-1 promoter from spinach (Lubberstedt et al., Plant Physiol., 104: 997-1006 (1994)), the cab1R promoter from rice (Luan et al., Plant Cell, 4:971-981 (1992)), the pyruvate orthophosphate dikinase (PPDK) promoter from corn (Matsuoka et al., Proc. Natl. Acad. Sci. USA, 90:9586-9590 (1993)), the tobacco Lhcb1*2 promoter (Cerdan et al., Plant Mol. Biol., 33:245-255 (1997)), the *Arabidopsis thaliana* SUC2 sucrose-H+ symporter promoter (Truernit et al., Planta, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

v. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, Plant Cell, 3(10):1051-1061 (1991)), the Commelina yellow mottle virus (CoYMV) promoter (Medberry et al., Plant Cell, 4(2):185-192 (1992)), and the rice tungro bacilliform virus (RTBV) promoter (Dai et al., Proc. Natl. Acad. Sci. USA, 101(2):687-692 (2004)).

vi. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

vii. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

viii. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA(b) and CryIA(c) (Braga et al. 2003, Journal of new seeds 5:209-221).

ix. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

x. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a truncated lignin-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous lignin-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a lignin-modulating polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of lignin. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in lignin level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), *Triticosecale* (triticum—wheat×rye) and bamboo.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea.*

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Rosa* spp. (rose), *Dianthus caryophyllus* (carnation), *Petunia* spp. (petunia) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus,* and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum,* and *Zea.* In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp.×*Miscanthus* sp.)

In some embodiments, the truncated *sorghum* CAD sequences of the methods and composition described herein are from wild, weedy, or cultivated *sorghum* species such as, but not limited to, *Sorghum almum, Sorghum amplum, Sorghum angustum, Sorghum arundinaceum, Sorghum bicolor* (such as *bicolor, guinea, caudatum, kafir,* and *durra*), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare,* or hybrids such as *Sorghum×almum,* or *Sorghum×drummondii.*

D. Transgenic Plant Phenotypes

In some embodiments, a plant in which expression of at least one lignin-modulating polypeptide is modulated can have decreased levels of lignin. For example, a lignin-modulating polypeptide described herein can be expressed in a transgenic plant, resulting in decreased levels of lignin. Decreased levels of lignin may mean decreased levels of total lignin, and/or ratios of Syringyl liginin, Guaiacyl lignin, and p-Hydroxyphenyl lignin monomers. The lignin level can be decreased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the lignin level in a corresponding control plant that does not express the transgene. In some embodiments, a plant in which expression of a lignin-modulating polypeptide is modulated can have decreased levels of lignin in harvestable biomass. Decreases in lignin in such plants can provide improved biomass to biofuel conversion. In some embodiments, a plant in which expression of a lignin-modulating polypeptide is modulated can have increased or decreased levels of lignin in one or more plant tissues, e.g., leaf tissues, or stem tissues. In some embodiments, a truncated CAD described herein is transformed into and expressed in *sorghum* that is already positive for one or more alleles encoding truncated polypeptides of CAD and/or COMT. In such embodiments, lignin content may be further decreased from the content found in the parent plants. Lignin content of a sample can be analyzed using methods standard in the art.

Typically, a difference in the amount of lignin in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the amount of lignin is statistically significant at $p<0.01$, $p<0.005$, or $p<0.001$. A statistically significant difference in, for example, the amount of lignin in a transgenic plant compared to the amount in cells of a control plant indicates that the recombinant nucleic acid present in the transgenic plant results in altered lignin levels.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, 51 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

E. Other Phenotypes

In some embodiments, the transgenic or non-transgenic plants identified or produced by the methods described herein have modulated lignin content in comparison to plants that do not comprise endogenous or exogenous genes encoding at least one truncated CAD allele. In such embodiments, the lignin content can be decreased by about 1, 2, 3, 4, 5, 6, 7, 8, 9, 10, 15, 20, 25, 30, 35, 40, 50, 60, 70, or 80 percent. In some embodiments, the transgenic or non-transgenic plants identified or produced by the methods described herein have modified yield of fermentable sugars in comparison to plants that do not comprise endogenous or exogenous genes encoding at least one truncated CAD allele. Such sorghum plants having one or more truncated CAD alleles as described herein have an increase in the yield of fermentable sugars, such as but not limited to, glucose, arabinose, fructose, galactose, or xylose, wherein the yield is increased by about 5, 10, 15, 20, 25, 30, 35, 40, 45, 50, 55, 60, 65, 70, 75, 80, 85, or 90 percent. In some embodiments, the transgenic plants described herein or the non-transgenic plants identified or produced by the methods described herein have altered lignin in comparison to plants that do not comprise endogenous or exogenous genes encoding at least one truncated CAD allele. In some embodiments, the altered lignin has a decrease in guaiacyl and syringyl residues. In some embodiments, the developmental gradient of lignin is altered. In some embodiments, the cell wall composition is altered. In some embodiments, lignin subunit composition is altered.

In some embodiments, the transgenic plants described herein or the non-transgenic plants identified or produced by the methods described herein comprise one or more truncated CAD sequences and one or more truncated COMT sequences.

V. PLANT GENOTYPING

The ability to characterize an individual by its genome is based on differences in nucleotide sequences among individuals. Typically, genetic markers are polymorphic regions of a genome and the complementary oligonucleotides which bind to these regions. The major causes of polymorphisms, and thus the major sources of genetic markers, are insertions (additions), deletions, nucleotide substitutions (point mutations), recombination events, and transposable elements within the genome of individuals in a plant population. As one example, point mutations can result from errors in DNA replication or damage to the DNA. As another example, insertions and deletions can result from inaccurate recombination events. As yet another example, variation can arise from the insertion or excision of a transposable element (a DNA sequence that has the ability to move or to jump to new locations with the genome, autonomously or non-autonomously).

Described herein are methods and kits for determining the genotype of a *sorghum* plant comprising detecting in the genome of the plant at least a first polymorphism at a CAD locus. The methods, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method. In one embodiment, described herein are a method for identifying *sorghum* plant lines with a truncated CAD comprising supplying a nucleic acid sample for a *sorghum* plant, providing amplification primers for amplifying a region of a *sorghum* plant corresponding to a truncated CAD gene present in said nucleic acid sample, applying said amplification primers to said nucleic acid sample such that amplification of said region of said CAD gene occurs, and identifying *sorghum* plants having a truncated CAD based on the presence of one or more mutations that confer a truncation in said amplified nucleic acid sample.

Polymorphisms may be detected by means known in the art. For example, molecular markers specific to CAD truncations can be used. Examples, of molecular markers include, oligonucleotides, single nucleotide polymorphisms (SNPs), multinucleotide polymorphisms, an insertion or a deletion of at least one nucleotide (indel), a simple sequence repeat (SSR), a restriction fragment length polymorphism (RFLP), an EST sequence or a unique nucleotide sequence of 20-40 bases used as a probe (oligonucleotides), a random amplified polymorphic DNA (RAPD) marker, or an arbitrary fragment length polymorphism (AFLP). As will be evident to one of skill, the number and type of markers required can differ. Markers can be used in conjunction with labeling or PCR to detect and score polymorphisms. Discovery, detection, and genotyping of various genetic markers have been well described in the literature. See, e.g., Henry, ed. (2001) Plant Genotyping. The DNA Fingerprinting of Plants Wallingford: CABI Publishing; Phillips and Vasil, eds. (2001) DNA-based Markers in Plants Dordrecht: Kluwer Academic Publishers; Pejic et al. (1998) "Comparative analysis of genetic similarity among maize inbred lines detected by RFLPs, RAPDs, SSRs and AFLPs" *Theor. App. Genet.* 97: 1248-1255; Bhattramakki et al. (2002) "Insertion-deletion polymorphisms in 3' regions of maize genes occur frequently and can be used as highly informative genetic markers" *Plant Mol. Biol.* 48: 539-47; Nickerson et al. (1997) "PolyPhred: automating the detection and genotyping of single nucleotide substitutions using fluorescence-based resequencing" *Nucleic Acids Res.* 25: 2745-2751; Underhill et al. (1997) "Detection of numerous Y chromosome biallelic polymorphisms by denaturing high-performance liquid chromatography" *Genome Res.* 7: 996-1005; Rafalski et al. (2002) "The genetic diversity of components of rye hybrids" *Cell Mol Biol Lett* 7: 471-5; Ching and Rafalski (2002) "Rapid genetic mapping of ests using SNP pyrosequencing and indel analysis" *Cell Mol Biol Lett.* 7: 803-10; and Powell et al. (1996) "The comparison of RFLP, RAPD, AFLP and SSR (microsatellite) markers for germplasm analysis" *Mol. Breeding.* 2: 225-238.

In some embodiments, where nucleic acids are used to identify a truncated CAD, the nucleic acids can be shorter in length than the truncated CAD sequence, and comprise the truncating stop codon or a sequence complimentary to the truncating stop codon. In some embodiments, the nucleic acids used to identify a truncated CAD terminate with the truncating stop codon or a sequence complimentary to the truncating stop codon. In some embodiments, the nucleic acids used to identify a truncated CAD are about 4, 5, 6, 7, 8, 9, 10, 12, 14, 16, 18, 20, 25, 30, 35, 40, 45, 50, 55, or 60 nucleotides in length. Such polynucleotides may be used as primers or probes.

In some embodiments, oligonucleotides specific to wild-type (wt) and mutant CAD alleles can be used to detect and score the genotype of a *sorghum* plant. For example, the CAD alleles of SEQ ID NOs: 7 and 13 can be detected and scored using SEQ ID NOs: 34 and/or 36. Such SNP sequences can be amplified in PCR reactions to detect and score genotypes of CAD alleles. In some embodiments, the polymorphism detected is a difference in a CAD nucleotide sequence which results in a stop codon. For example, SEQ ID NOs: 7 and 13 have single nucleotide differences that result in stop codons at positions 4089 and 2800, respectively. SNPs can be discovered and detected by any of a number of techniques known in the art. For example, SNPs can be detected by direct sequencing of DNA segments, e.g., amplified by PCR, from several individuals (see, e.g., Ching et al. (2002) "SNP frequency, haplotype structure and linkage disequilibrium in elite maize inbred lines" BMC Genetics 3: 19). As another example, SNPs can be discovered by computer analysis of available sequences (e.g., ESTs, STSS) derived from multiple genotypes (see, e.g., Marth et al. (1999) "A general approach to single-nucleotide polymorphism discovery" Nature Genetics 23: 452-456 and Beutow et al. (1999) "Reliable identification of large numbers of candidate SNPs from public EST data" Nature Genetics 21: 323-325). Indels, insertions or deletions of one or more nucleotides, can also be discovered by sequencing and/or computer analysis, e.g., simultaneously with SNP discovery. Similarly, SNPs can be genotyped by sequencing. SNPs can also be genotyped by various other methods (including high throughput methods) known in the art, for example, using DNA chips, allele-specific hybridization, allele-specific PCR, and primer extension techniques. See, e.g., Lindblad-Toh et al. (2000) "Large-scale discovery and genotyping of single-nucleotide polymorphisms in the mouse" Nature Genetics 24: 381-386; Bhattramakki and Rafalski (2001) "Discovery and application of single nucleotide polymorphism markers in plants" in Plant Genotyping: The DNA Fingerprinting of Plants, CABI Publishing; Syvanen (2001) "Accessing genetic variation: genotyping single nucleotide polymorphisms" Nat. Rev. Genet. 2: 930-942; Kuklin et al. (1998) "Detection of single-nucleotide polymorphisms with the WAVE TM DNA fragment analysis system" Genetic Testing 1: 201-206; Gut (2001) "Automation in genotyping single nucleotide polymorphisms" Hum. Mutat. 17: 475-492; Lemieux (2001) "Plant genotyping based on analysis of single nucleotide polymorphisms using microarrays" in Plant Genotyping: The DNA Fingerprinting of Plants, CABI Publishing; Edwards and Mogg (2001) "Plant genotyping by analysis of single nucleotide polymorphisms" in Plant Genotyping: The DNA Fingerprinting of Plants, CABI Publishing; Ahmadian et al. (2000) "Single-nucleotide polymorphism analysis by pyrosequencing" Anal. Biochem. 280: 103-110; Useche et al. (2001) "High-throughput identification, database storage and analysis of SNPs in EST sequences" Genome Inform Ser Workshop Genome Inform 12: 194-203; Pastinen et al. (2000) "A system for specific, high-throughput genotyping by allele-specific primer extension on microarrays" Genome Res. 10: 1031-1042; Hacia (1999) "Determination of ancestral alleles for human single-nucleotide polymorphisms using high-density oligonucleotide arrays" Nature Genet. 22: 164-167; and Chen et al. (2000) "Microsphere-based assay for single-nucleotide polymorphism analysis using single base chain extension" Genome Res. 10: 549-557. Multinucleotide polymorphisms can be discovered and detected by analogous methods.

In some embodiments, where the CAD truncation is generated by mutagenesis, the CAD alleles are first sequenced and then oligonucleotides specific to the mutant sequence can be designed and synthesized based on the nucleic acid sequence. In some embodiments, where the CAD mutation is synthesized and introduced into a plant, oligonucleotides specific to the truncation can be designed and synthesized based on the nucleic acid sequence. Synthesized mutants may be based on the nucleotide sequence of any *sorghum* CAD allele.

In some embodiments of the methods and kits described herein, one or more sets of oligonucleotides, each capable of recognizing the presence or absence of a specific and defined genomic position, is used. For organisms with more chromosomes more oligonucleotides are desirable. The lower limit is one oligonucleotide pair and the upper limit is set by the desired resolution capacity of the method and the test kit. Hybridization of the oligonucleotides to DNA from the *sorghum* plant is preferably recorded in situ by any conventional labelling system, applying for instance terminal transferase and conventional recordable labels. As an alternative to in situ labelling the hybridized sample DNA may be released from the solid support and subsequently hybridized with labelled polynucleotide sequences corresponding to each of the original oligonucleotide sequences attached to the solid support. Hybridization is optionally reversible and the solid support can be returned to its original state for reuse. A labelled dideoxynucleotide can be incorporated at the end of the oligonucleotide provided that the oligonucleotide is hybridized to genomic DNA as template. The nucleotide sequence at the genomic position adjacent to the region matching the oligonucleotide is known and therefore the particular nucleotide which will be incorporated (A, C, G, T or U) is known. Co-dominant scoring is achieved using paired, i.e. two or parallel, i.e. three, flanking oligonucleotide sequences. The results obtained are recorded as full, empty, failure or null alleles and can be used to distinguish between heterozygous and/or homozygous genotypes. Optional post-hybridization treatments, including washing and digestion, are provided in order to remove sample DNA not fully hybridized to the solid support-attached oligonucleotide sequences, for example before and after labelling. The presence or absence of hybridization is recorded using a method allowing the recording of the hybridization state.

VI. PLANT BREEDING

One or more of the methods of breeding described herein can be used with the sequences described herein. In particular, the primer pairs and probes described herein are of value in breeding programs because when incorporating the truncated CAD alleles into a different genetic background, such as an elite cultivar, a modified backcrossing scheme can be used, where the inheritance of the truncated CAD alleles is tracked with the primer pairs or probes. This eliminates the need for self-pollination to reveal the phenotype associated with homozygosity for a truncated CAD allele, and thus saves time and effort.

*Sorghum* plants are bred in most cases by self pollination techniques. With the incorporation of male sterility (either genetic or cytoplasmic) cross pollination breeding techniques can also be utilized. *Sorghum* has a perfect flower with both male and female parts in the same flower located in the panicle. The flowers are usually in pairs on the panicle branches. Natural pollination occurs in *sorghum* when anthers (male flowers) open and pollen falls onto receptive stigma (female flowers). Because of the close proximity of male (anthers) and female (stigma) in the panicle, self pollination can be high. Cross pollination may occur when wind or convection currents move pollen from the anthers of one plant to receptive stigma on another plant. Cross pollination is greatly enhanced with incorporation of male sterility which renders male flowers nonviable without affecting the female flowers. Successful pollination in the case of male sterile flowers requires cross pollination.

The development of *sorghum* hybrids requires the development of homozygous inbred lines, the crossing of these lines, and the evaluation of the crosses. Pedigree breeding methods, and to a lesser extent population breeding methods, are used to develop inbred lines from breeding populations. Breeding programs combine desirable traits from two or more inbred lines into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding five or more generations of selfing and selection is practiced. $F_1$ to $F_2$; $F_2$ to $F_3$; $F_3$ to $F_4$; $F_4$ to $F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate genes(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A hybrid *sorghum* variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The hybrid is more vigorous than its inbred parents. This hybrid vigor, or heterosis, can be manifested in many ways, including increased vegetative growth and increased yield.

The development of a hybrid *sorghum* variety involves five steps: (1) the formation of "restorer" and "non-restorer" germplasm pools; (2) the selection of superior plants from various "restorer" and "non-restorer" germplasm pools; (3) the selfing of the superior plants for several generations to produce a series of inbred lines, which although different from each other, each breed true and are highly uniform; (4) the conversion of inbred lines classified as non-restorers to cytoplasmic male sterile (CMS) forms, and (5) crossing the selected cytoplasmic male sterile (CMS) inbred lines with selected fertile inbred lines (restorer lines) to produce the hybrid progeny ($F_1$).

Because *sorghum* is normally a self pollinated plant and because both male and female flowers are in the same panicle, large numbers of hybrid seed can only be produced by using cytoplasmic male sterile (CMS) inbreds. Inbred male sterile lines are developed by converting inbred lines to CMS. This is achieved by transferring the chromosomes of the line to be sterilized into sterile cytoplasm by a series of backcrosses, using a male sterile line as a female parent and the line to be sterilized as the recurrent and pollen parent in all crosses. After conversion to male sterility the line is designated the (A) line. Lines with fertility restoring genes cannot be converted into male sterile A-lines. The original line is designated the (B) line.

Flowers of the CMS inbred are fertilized with pollen from a male fertile inbred carrying genes which restore male fertility in the hybrid ($F_1$) plants. An important consequence of the homozygosity and homogeneity of the inbred lines is that the hybrid between any two inbreds will always be the same. Once the inbreds that give the best hybrid have been identified, the hybrid seed can be reproduced indefinitely as long as the homogeneity of the inbred parent is maintained.

A single cross hybrid is produced when two inbred lines are crossed to produce the $F_1$ progeny. Much of the hybrid vigor exhibited by $F_1$ hybrids is lost in the next generation ($F_2$). Consequently, seed from hybrid varieties is not typically used for planting stock.

Hybrid *sorghum* can be produced using wind to move the pollen. Alternating strips of the cytoplasmic male sterile inbred (female) and the male fertile inbred (male) are planted in the same field. Wind moves the pollen shed by the male inbred to receptive stigma on the female. Providing that there is sufficient isolation from sources of foreign *sorghum* pollen, the stigma of the male sterile inbred (female) will be fertilized only with pollen from the male fertile inbred (male). The resulting seed, born on the male sterile (female) plants is therefore hybrid and will form hybrid plants that have full fertility restored. In some embodiments, if the hybrid *sorghum* is used as forage or for biomass production, then it may be unnecessary to restore fertility.

In some embodiments, inbred parental lines, elite breeding lines, or hybrid *sorghum* are bred by the methods described herein to comprise one or more alleles for which the CAD coding sequence is truncated relative to a wild-type CAD coding sequence and one or more alleles for which the COMT coding sequence is truncated relative to a wild-type COMT coding sequence. In some embodiments, the *sorghum* plants developed are high biomass varieties for biofuel production.

In some embodiments, other breeding methods may be used in conjunction or as part of the methods described herein.

A. Recurrent Selection and Mass Selection

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are self pollinated or cross pollinated with each other to form progeny for another population. This population is planted and again superior plants are selected to self pollinate or cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties. The number of parental plant varieties, populations, wild accessions, ecotypes, etc., that are used to generate a synthetic can vary from as little as 10 to as much as 500. Typically, about 100 to 300 varieties, populations, etc., are used a parents for the synthetic variety. Seed from the parental seed production plot of a synthetic variety can be sold to the farmer. Alternatively, seed from the parental seed production plot can subsequently undergo one or two generations of multiplication, depending on the amount of seed produced in the parental plot and the demand for seed.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

B. Mutation Breeding

Mutation breeding is another method of introducing new traits into *sorghum*. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (such as from 2500 to 2900 nm), or chemical mutagens (such as base analogues (5-bromouracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, 1993. Principles of Cultivar Development, Macmillan Publishing Company. In addition, mutations created in other *sorghum* plants may be used to produce a backcross conversion of *sorghum* that comprises such mutation. In addition, mutations created in other lines may be used to produce a backcross conversion of elite lines that comprise such mutations.

C. Breeding with Molecular Markers

The plant genotyping techniques described herein may be used in marker-assisted plant breeding methods in *sorghum*. In addition, techniques such as Isozyme Electrophoresis, Arbitrarily Primed Polymerase Chain Reaction (AP-PCR), DNA Amplification Fingerprinting (DAF), and Sequence Characterized Amplified Regions (SCARs) can be used in marker-assisted breeding.

One use of the plant genotyping techniques described herein is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

D. Genomic selection

One potential problem with marker assisted selection is that only a limited proportion of the total genetic variance is captured by the markers. An alternative to tracing a limited number of QTL with markers is to trace all the QTL. This can be done by dividing the entire genome up into chromosome segments, for example defined by adjacent markers, and then tracing all the chromosome segments. This method was termed genomic selection by Meuwissen et al. 2001 "Prediction of total genetic value using genome-wide dense marker maps" Genetics 157:1819-1829. With the availability of high-density marker maps and cost effective genotyping, genomic selection methods can provide faster genetic gain than can be achieved by current selection methods based on phenotypes and pedigree. Some of the factors driving the accuracy of genomic selection include marker density and marker type (i.e., microsatellite and SNP markers). With genomic selection, selection is typically on the sum of estimates of effects of all marker intervals across the genome, fitted either as fixed (fixed GS) or random (random GS) effects. Responses to selection are tracked by indices over generations. The efficiency of genomic selection over standard marker assisted selection depends on stringency of the threshold used for QTL detection. One skilled in the art can optimize factors that affect genomic selection for a particular species such as *Sorghum* species.

E. Production of Double Haploids

The production of double haploids can also be used for the development of plants with a homozygous phenotype in the breeding program. For example, a *sorghum* cultivar as a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989 and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, 1959, Am. Nat. 93:381-382; Sharkar and Coe, 1966, Genetics 54:453-464), KEMS (Deimling, Roeber, and Geiger, 1997, Vortr. Pflanzenzuchtg 38:203-224), or KMS and ZMS (Chalyk, Bylich & Chebotar, 1994, MNL 68:47; Chalyk & Chebotar, 2000, Plant Breeding 119:363-364), and indeterminate gametophyte (ig) mutation (Kermicle 1969 Science 166:1422-1424).

Methods for obtaining haploid plants are also disclosed in Kobayashi, M. et al., J. Heredity 71(1):9-14, 1980, Pollacsek, M., Agronomie (Paris) 12(3):247-251, 1992; Cho-Un-Haing et al., J. Plant Biol., 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S.

Thus, one embodiment is a process for making a substantially homozygous *sorghum* progeny plant by producing or obtaining a seed from the cross of two *sorghum* plants and applying double haploid methods to the $F_1$ seed or $F_1$ plant or to a subsequent filial generation. Based on studies in maize, such methods can decrease the number of generations required to produce a variety with similar genetics or characteristics to *sorghum*. See Bernardo, R. and Kahler, A. L., Theor. Appl. Genet. 102:986-992, 2001. Descriptions of other breeding methods that are commonly used for different traits and crops can be found in one of several reference books (e.g., Allard, 1960; Simmonds, 1979; Sneep et al., 1979; Fehr, 1987).

F. Backcrossing

A plant breeding technique called backcrossing can be utilized wherein essentially all of the desired morphological and physiological characteristics of a variety are recovered in addition to a single gene that is transferred into the variety via the backcrossing technique. Backcrossing methods can be used to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental *sorghum* plant that contributes the gene for the desired characteristic is termed the nonrecurrent or donor parent. This terminology refers to the fact that the nonrecurrent parent is used one time in the backcross protocol and therefore does not recur. The parental *sorghum* plant to which the gene or genes from the nonrecurrent parent are transferred is known as the recurrent parent as it is used for several rounds in the backcrossing protocol (Poehlman & Sleper, 1994; Fehr, Principles of Cultivar Development pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *sorghum* plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are sometimes not selected for in the development of a new variety but that can be improved by backcrossing techniques. Single gene traits may or may not be transgenic; examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959, 185; 5,973,234 and 5,977,445; the disclosures of which are specifically hereby incorporated by reference in their entirety.

G. Pedigree Breeding

Pedigree breeding starts with the crossing of two genotypes, having one or more desirable characteristics that is lacking or which complements the other. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. In some embodiments, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a *sorghum* variety may be crossed with another variety to produce a first generation progeny plant. The first generation progeny plant may then be back-crossed to one of its parent varieties to create a $BC_1$ or $BC_2$. Progeny are selfed and selected so that the newly developed variety has many of the attributes of the recurrent parent and yet several of the desired attributes of the non-recurrent parent. This approach leverages the value and strengths of the recurrent parent for use in new *sorghum* varieties.

VII. ARTICLES OF MANUFACTURE

Transgenic and non-transgenic plants described herein have various uses in the agricultural and energy production industries. For example, transgenic plants described herein can be used to make animal feed and food products. Such plants, however, are often particularly useful as a feedstock for energy production.

Transgenic plants described herein often produce biomass with decreased or altered lignin content, relative to control plants that lack the exogenous nucleic acid. Non-transgenic plants described herein, such as those produced or selected by the methods described herein often produce biomass with decreased or altered lignin content, relative to control plants that lack one or more of the nucleic acids described herein. In some embodiments, such plants provide equivalent or even increased yields of grain and/or biomass per hectare relative to control plants when grown under conditions of reduced inputs such as fertilizer and/or water. Thus, such transgenic and non-transgenic plants can be used to provide yield quality improvements at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the lignin composition of the plant material. By providing improved yields at an equivalent or even decreased cost of production, the transgenic plants described herein improve profitability for farmers and processors as well as decrease costs to consumers.

Seeds from plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

Kits for genotyping plants for identification, selection, or breeding can comprise a means of detection of the presence of a truncated CAD in a sample of *sorghum* DNA. In some embodiments, a kit comprises one or more SNPs, such as SEQ ID NOs: 34-37, or a protein encoded by a polynucleotide as described herein. In some embodiments, a kit comprises one or more polynucleotide SNPs specific to a truncated CAD 131 to 320 amino acids in length. In some embodiments, a kit comprises one or more polynucleotide SNPs specific to a C-terminus truncated *sorghum* COMT, such as those described by Bout and Vermerris, which is in incorporated by reference herein in its entirety (Bout and Vermerris, 2003, A candidate-gene approach to clone the *sorghum* Brown midrib gene encoding COMT, Mol. Gen. Genomics 269:205-214). The kits described herein may be useful for genetic identity determination, phylogenetic studies, parenthood determinations, genotyping, haplotyping, pedigree analysis, forensic identification and/or plant breeding particularly with co-dominant scoring.

In an embodiment, a kit may further comprise reagents for DNA amplification-detection technology such as PCR or TaqMan™. In another embodiment a kit may further comprise reagents for probe hybridization-detection technology such as Southern Blots, Northern Blots, in-situ Hybridization, or microarrays. In another embodiment, a kit may comprise reagents for antibody binding-detection technology such as Western Blots, ELISA's, SELDI mass spectrometry or test strips. In another embodiment, a kit may comprise reagents for lignin content analysis technology. In some embodiments, a kit may comprise instructions for one or more of the methods described above.

The invention will be further described in the following examples, which do not limit the scope of the invention described in the claims.

VIII. EXAMPLES

Example 1

Transgenic *Arabidopsis* plants

Each isolated nucleic acid described herein that encodes a truncated CAD can be cloned into a Ti plasmid vector containing a phosphinothricin acetyltransferase gene which confers Finale™ resistance to transformed plants. Constructs can be made using any of the nucleic acids described herein, each operably linked to a promoter or regulatory element. Wild-type *Arabidopsis thaliana* ecotype Wassilewskija (Ws) plants can be transformed separately with each construct. The transformations can be performed essentially as described in Bechtold et al., C. R. Acad. Sci. Paris, 316:1194-1199 (1993).

The presence of each vector containing a nucleic acid described herein in the respective transgenic *Arabidopsis* line transformed with the vector can be confirmed by Finale™ resistance, PCR amplification from green leaf tissue extract, and/or sequencing of PCR products. As controls, wild-type *Arabidopsis* ecotype Ws plants can be transformed with an empty vector.

Example 2

Genotyping of *Sorghum* Plants Having a C-Terminus Truncated Sorghum CAD

DNA samples were extracted from *sorghum* GRIN germplasm accession nos.: PI 535790, PI 535806, PI 599692, PI 599697, PI 599705, PI 599720, PI 599731, PI 599740, PI 599750, PI 602730, PI 602740, PI 602898, PI 602902, PI 602906, PI 602910, PI 602914, PI 606705, PI 606706, and Ceres accession nos.:BICOLOR-81733675, GRAINERIII-81733676 (Conventional *Sorghum* Sudangrass Hybrid), 98093-81733674 (Conventional type Hybrid Forage *Sorghum*), SS1-81733673 (Sudan×Sudan), 22043-81733671 (*sorghum* sudangrass Hybrid), and 24213-81733672 (Hybrid forage *sorghum* (Long season)). The CAD alleles were amplified from each accession using oligonucleotide primer sets for PCR (SEQ ID NOs: 38-61). PCR amplification products were sequenced and analyzed.

CAD nucleotide sequences of *sorghum* accessions PI602730-81733686 and PI535790-81733677 were analyzed and each contained a different point mutation altering a single nucleotide (C→T), each of which resulted in a premature stop codon (SEQ ID NOs: 7 and 13).

Oligonucleotides were developed having specificity to the SNPs in the nucleic acid sequences of wild type and mutant CAD alleles (SEQ ID NOs: 34-37). The oligonucleotides were tested on DNA extracted from *sorghum* accessions. PI602730-81733686 and PI602910-85802580 were homozygous for a CAD allele featuring a SNP resulting in a premature stop codon encoding a truncated polypeptide of 320 amino acids. PI535790-81733677, PI535806-81733678, PI602740-81733687, PI602902-81733689, and PI602906-81733690 were homozygous for a CAD allele featuring a SNP resulting in a premature stop codon encoding a truncated polypeptide of 131 amino acids. Accessions 22043 and 24213 were heterozygous for the CAD allele encoding the 131 amino acid truncated CAD polypeptide. Results of oligonucleotide assisted genotyping are shown in Table 1.

TABLE 1

SNP Genotyping of Sorghum Accessions.

| Accession | Plant ID | CAD Truncation 1 (BMR-6 131 aa) with T C/T | CAD Truncation 2 (BMR-17 320 aa) with T C/T | gDNA SEQ ID NO: | cDNA SEQ ID NO: |
|---|---|---|---|---|---|
| PI 535790 | N105 | T | C | 13 | 14 |
| PI 535806 | N121 | T | C | | Same as PI 602906 |
| PI 599692 | MP26 | C | C | 2 | 3 |
| PI 599697 | MP31 | C | C | | Same as PI 599705 |
| PI 599705 | MP39 | C | C | 25 | 26 |
| PI 599720 | MP54 | T | C | | Same as PI 602906 |
| PI 599731 | MP65 | C | C | | Same as PI 599705 |
| PI 599740 | MP74 | C | C | | Same as PI 599692 |
| PI 599750 | MP84 | C | C | | Same as PI 599705 |
| PI 602730 | BMP449 | C | T | 7 | 8 |
| PI 602740 | BMP454 | T | C | | Same as PI 535790 |
| PI 602898 | AMP11 | C | C | | Same as PI 599705 |
| PI 602902 | AMP13 | T | C | | Same as PI 602906 |
| PI 602906 | AMP15 | T | C | 22 | 23 |
| PI 602910 | AMP17 | C | T | | Same as PI 602730 |
| PI 602914 | AMP19 | C | C | 28 | 29 |
| PI 606705 | Tift 98bmrA1 | C | C | | Same as PI 599705 |
| PI 606706 | Tift 98bmrB1 | C | C | | Same as PI 599705 |
| BICOLOR | | C | C | 10 | 11 |
| GRAINERIII | | C | C | | Same as PI 599705 |
| 98093 | | C | C | | Same as PI 599705 |
| SS1 | | C | C | 31 | 32 |
| 22043 | | C/T | C | 4 | 5 |
| 24213 | | C/T | C | Same as PI 599705 | Same as PI 599705 |

Example 3

Breeding of *Sorghum* Plants Having a Truncated CAD

The oligonucleotides described herein can be used in marker assisted breeding to produce inbred *sorghum* lines that are homozygous for a CAD allele encoding a truncated CAD polypeptide, which can be crossed to make hybrid *sorghum* that are homozygous for the CAD allele encoding a truncated CAD polypeptide. For example, PI602730-81733686 can be crossed with a male sterile (A-line) that does not contain a CAD allele encoding a truncated CAD polypeptide but which has agronomically desirable traits. The resulting progeny in $F_2$ generations can be screened using the oligonucleotides for plants that are heterozygous or homozygous for the CAD allele encoding truncated CAD polypeptides and are male sterile. Such progeny can be backcrossed to the A-line and through generations of selection a new A-line can be developed which is homozygous for the CAD allele encoding a truncated CAD polypeptide. The same process can be applied to B and R lines, so that the three lines can be used to produce hybrid seed that is homozygous for the CAD allele encoding a truncated CAD polypeptide.

Example 4

Determination of Functional Homologs or Allelic Variants by Reciprocal BLAST

A process known as Reciprocal BLAST (Rivera et al., Proc. Natl. Acad. Sci. USA, 95:6239-6244 (1998)) can be used to identify potential functional homolog sequences as well as allelic variants from databases consisting of all available public and proprietary peptide sequences, including NR from NCBI and peptide translations from Ceres clones.

Before starting a Reciprocal BLAST process, a specific reference polypeptide can be searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides can be designated as a cluster.

The BLASTP version 2.0 program from Washington University at Saint Louis, Mo., USA can be used to determine BLAST sequence identity and E-value. The BLASTP version 2.0 program includes the following parameters: 1) an E-value cutoff of 1.0e-5; 2) a word size of 5; and 3) the –postsw option. The BLAST sequence identity can be calculated based on the alignment of the first BLAST HSP (High-scoring Segment Pairs) of the identified potential functional homolog or allelic variant sequence with a specific reference polypeptide. The number of identically matched residues in the BLAST HSP alignment can be divided by the HSP length, and then multiplied by 100 to get the BLAST sequence identity. The HSP length typically includes gaps in the alignment, but in some cases gaps can be excluded.

The main Reciprocal BLAST process consists of two rounds of BLAST searches; forward search and reverse search. In the forward search step, a reference polypeptide sequence, "polypeptide A," from source species SA can be BLASTed against all protein sequences from a species of interest. Top hits can be determined using an E-value cutoff of 10-5 and a sequence identity cutoff of 35%. Among the top hits, the sequence having the lowest E-value can be designated as the best hit, and considered a potential functional homolog or ortholog. Any other top hit that had a sequence identity of 80% or greater to the best hit or to the original reference polypeptide can be considered a potential functional homolog or ortholog as well. This process can be repeated for all species of interest. Allelic variants typically have higher sequence identity to a reference sequence, i.e., greater than 90%, and originating from the same species as the reference sequence. Allelic variants can be compared to available genome reference maps and inter-species comparative maps to determine the likelihood that the allelic variants identified correlate to the same locus.

In the reverse search round, the top hits identified in the forward search from all species can be BLASTed against all protein sequences from the source species SA. A top hit from the forward search that returned a polypeptide from the aforementioned cluster as its best hit can also be considered as a potential functional homolog.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid comprising a nucleotide sequence encoding a CAD polypeptide, wherein said CAD polypeptide has at least 98% sequence identity to amino acids 1-130 or 1-319 of SEQ ID NO: 6 and terminates at a position corresponding to residue 131 or 320 of SEQ ID NO: 6.

2. The nucleic acid of claim 1, wherein said CAD polypeptide is from *sorghum*.

3. The nucleic acid of claim 1, wherein said nucleic acid is a synthetic nucleic acid.

4. An isolated nucleic acid comprising a nucleotide sequence encoding a *sorghum* CAD polypeptide, wherein said *sorghum* CAD polypeptide has at least 80% sequence identity to amino acids 1-130 or 1-319 of SEQ ID NO: 6 and terminates at a position corresponding to residue 131 or 320 of SEQ ID NO: 6.

5. The nucleic acid of claim 1 or 4, wherein said nucleotide sequence comprises a thymine corresponding to position 2794 of SEQ ID NO:2, position 2800 of SEQ ID NO: 4, 7, 10, or 13, position 4083 SEQ ID NO: 2, position 4089 of SEQ ID NOs: 4 or 7, position 4090 of SEQ ID NO: 10, position 497 of SEQ ID NO: 1, position 394 of SEQ ID NOs: 3, 5, 8, 11, or 14, position 1064 of SEQ ID NO:1, position 962 of SEQ ID NO:11, or position 961 of SEQ ID NOs: 3, 5, or 8.

6. The nucleic acid of claim 1 or 4, having at least 80% sequence identity to a nucleotide sequence selected from the group consisting of SEQ ID NO: 1, 2, 3, 4, 5, 7, 8, 10, 11, 13, and 14.

7. A method of characterizing a *sorghum* plant comprising detecting a nucleic acid encoding a CAD polypeptide in said *sorghum* plant, wherein said CAD polypeptide has at least 80% sequence identity to amino acids 1-130 or 1-319 of SEQ ID NO: 6 and terminates at a position corresponding to residue 131 or 320 of SEQ ID NO: 6.

8. The method of claim 7, wherein said nucleic acid comprises a thymine corresponding to position 2794 of SEQ ID NO:2, position 2800 of SEQ ID NO: 4, 7, 10, or 13, position 4083 SEQ ID NO: 2, position 4089 of SEQ ID NOs: 4 or 7, position 4090 of SEQ ID NO: 10, position 497 of SEQ ID NO: 1, position 394 of SEQ ID NOs: 3, 5, 8, 11, or 14, position 1064 of SEQ ID NO:1, position 962 of SEQ ID NO:11, or position 961 of SEQ ID NOs: 3, 5, or 8.

9. A method of determining the presence of a polynucleotide in a *sorghum* plant, comprising:
 a) contacting at least one probe or primer pair with nucleic acid from said *sorghum* plant, wherein said probe or primer pair is specific for a polynucleotide that encodes a CAD polypeptide, wherein said CAD polypeptide has at least 80% sequence identity to amino acids 1-130 or 1-319 of SEQ ID NO: 6 and terminates at a position corresponding to residue 131 or 320 of SEQ ID NO: 6; and,
 b) determining whether or not said polynucleotide is present in said *sorghum* plant.

10. The method of claim 9, wherein said probe comprises at least one oligonucleotide.

11. The method of claim 10, wherein said oligonucleotide comprises a nucleotide sequence selected from the group consisting of SEQ ID NOs: 34 and 36.

12. A kit for genotyping a *sorghum* biological sample, said kit comprising a primer pair that specifically amplifies, or a probe that specifically hybridizes to, a polynucleotide that encodes a CAD polypeptide having at least 80% sequence identity to amino acids 1-130 or 1-319 of SEQ ID NO: 6 and terminating at a position corresponding to residues 131 or 320 of SEQ ID NO: 6.

13. The kit of claim 12, wherein at least one primer of said primer pair or probe has specificity for a thymine corresponding to position 2794 of SEQ ID NO:2, position 2800 of SEQ ID NO: 4, 7, 10, or 13, position 4083 SEQ ID NO: 2, position 4089 of SEQ ID NOs: 4 or 7, position 4090 of SEQ ID NO: 10, position 497 of SEQ ID NO: 1, position 394 of SEQ ID NOs: 3, 5, 8, 11, or 14, position 1064 of SEQ ID NO:1, position 962 of SEQ ID NO:11, or position 961 of SEQ ID NOs: 3, 5, or 8.

14. The kit of claim 12, wherein said at least one primer or said probe comprises a nucleotide sequence selected from the group consisting of SEQ ID NO: 34 and 36.

\* \* \* \* \*

UNITED STATES PATENT AND TRADEMARK OFFICE
CERTIFICATE OF CORRECTION

PATENT NO. : 8,298,794 B2
APPLICATION NO. : 12/575991
DATED : October 30, 2012
INVENTOR(S) : Timothy Swaller It is certified that error appears in the above-identified patent and that said Letters Patent is hereby corrected as shown below:

Column 126, Line 62 (Claim 5), please delete "NO:" and insert --NOs:--, therefor. (second occurrence)

Column 126, Line 63 (Claim 5), after "4083" insert --of--.

Column 127, Line 3 (Claim 6), please delete "NO:" and insert --NOs:--, therefor.

Column 127, Line 13 (Claim 8), please delete "NO:" and insert --NOs:--, therefor.

Column 127, Line 14 (Claim 8), after "4083" insert --of--.

Column 128, Line 18 (Claim 13), please delete "NO:" and insert --NOs:--, therefor. (first occurrence)

Column 128, Line 18 (Claim 13), after "4083" insert --of--.

Column 128, Line 26 (Claim 14), please delete "NO:" and insert --Nos:--, therefor.

Signed and Sealed this
Twenty-sixth Day of March, 2013

Teresa Stanek Rea
*Acting Director of the United States Patent and Trademark Office*

SEQUENCE LISTING

```
<160> NUMBER OF SEQ ID NOS: 61

<210> SEQ ID NO 1
<211> LENGTH: 1457
<212> TYPE: DNA
<213> ORGANISM: Sorghum bicolor
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Full length Cinnamyl-alcohol Dehydrogenase
<220> FEATURE:
<221> NAME/KEY: misc_feature
<223> OTHER INFORMATION: GI No. 119852230
<220> FEATURE:
<221> NAME/KEY: misc_feature
<223> OTHER INFORMATION: Encodes the peptide sequence at SEQ ID NO. 6

<400> SEQUENCE: 1
gatcgcccac cctctcggcc tctccaggcc gccgccggct ccgtcgtcgt gttccccgac        60
gcccgtagcg ttcgaccgcg gccagtccca gtccaagagg agaatgggga gcctggcgtc       120
cgagaggaag gtggtcggct gggccgccag ggacgccacc ggacacctct cccctacac       180 ctacaccctc aggaacacag gccctgaaga tgtggtggtg aaggtgctct actgtggaat       240
ctgccacacg gacatccacc aggccaagaa ccacctcggg gcttcaaagt accctatggt       300
ccctgggcac gaggtggtcg gtgaggtggt ggaggtcggg cccgaggtga gcaagtatgg       360
cgtcggcgac gtggtaggcg tcggggtgat cgtcgggtgc tgccgcgagt gcagcccctg       420
caaggccaac gttgagcagt actgcaacaa gaagatctgt tcctacaacg atgtctacac       480
tgacggccgg cccacgcagg gcggcttcgc ctccaccatg gtcgtcgacc agaagtttgt       540
ggtgaagatc ccggcgggtc tggcgccgga gcaagcggcg ccgctgctgt gcgcgggcgt       600
gacggtgtac agcccgctaa aggcctttgg gctgacggcc ccgggcctcc gcggtggcat       660
cgtgggcctg ggcggcgtgg gccacatggg cgtgaaggtg gcgaaggcca tgggccacca       720
cgtgacggtg atcagctcgt cgtccaagaa gcgcgcggag gcgatggacc acctgggcgc       780
ggacgcgtac ctggtgagca cggacgcggc ggccatggcg gcggccgccg actcgctgga       840
```

| | |
|---|---|
| ctacatcatc gacacggtgc ccgtgcacca cccgctggag ccctacctgt cgctgctgag | 900 |
| gctggacggc aagcacgtgc tgctgggcgt catcggcgag cccctcagct tcgtgtcccc | 960 |
| gatggtgatg ctggggcgga aggccatcac ggggagcttc atcggcagca tcgacgagac | 1020 |
| cgccgaggtg ctccagttct gcgtcgacaa ggggctcacc tcccagatcg aggtggtcaa | 1080 |
| gatggggtac gtgaacgagg cgctggagcg gctcgagcgc aacgacgtcc gctaccgctt | 1140 |
| cgtcgtcgac gtcgccggca gcaacgtcga ggaggatgcc gctgatgcgc cgagcaactg | 1200 |
| acggcgtgca acgttcgttc ggggctcgag gctgcctgcg cttctgcttc ctttagtaat | 1260 |
| tgtgggcttt gtgcgttctt gccgtgttct gttctggttc tgggcttcca gatgagttga | 1320 |
| aggatggtct gtttaaatgg catcagactg aataactata tgttgtagta gtacgtgtta | 1380 |
| tactcggagt acgccacgat atggtgtggt gtcagtgtca ccagcattct ggatttgcag | 1440 |
| tttacccaaa aaaaaaa | 1457 |

<210> SEQ ID NO 2
<211> LENGTH: 4292
<212> TYPE: DNA
<213> ORGANISM: Sorghum bicolor
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. PI599692-81733680
<220> FEATURE:
<221> NAME/KEY: misc_feature
<223> OTHER INFORMATION: Full length Cinnamyl-alcohol Dehydrogenase
<220> FEATURE:
<221> NAME/KEY: misc_feature
<223> OTHER INFORMATION: Encodes the peptide sequence at SEQ ID NO. 6

<400> SEQUENCE: 2

| | |
|---|---|
| atggggagcc tggcgtccga gaggaaggtg gtcggctggg ccgccaggga cgccaccgga | 60 |
| cacctctccc cctacaccta cacctcagg tacgccgctc cgccgccgcc gccgccactc | 120 |
| tagatcgctc gtgttcgtct tctcactttt cctaccccta gtcccctccc ccttcatgtc | 180 |
| cgtccgactg tgtctcctgc tccttgtgca aacacgaaaa tagatccagg agaggatgag | 240 |
| ggacggtttg gcttgtgcgg cgccttcttc agtgattgtc cgagatcgac caggaacagg | 300 |
| aagaacagta aaatctgagt catgattgtg atgatttttt ttttttaaaa aaaaacagga | 360 |
| tatatttccg atccacttcc acgattaggc cggtgcacgt atctaatcgc cggcaggttt | 420 |
| taatttggga aggatgctat acgtatgcat attctgatcc atatactata actgatacgt | 480 |
| ttacggttat catttaccga gtattccttc tcttgatttc tgtaagatgt tccttatgtt | 540 |
| atatgctgtg gtcgtatctt tttcctcaca catagtatac tagtagtaca ccttagtagg | 600 |
| agcactactc cacaacaaac gcatgcatgc gcatgcgcgg cagcatgcgc atgatacgtc | 660 |
| ttcaactcct ggtccaactc tagtgccgcc gcacatgcat gtatggatgc cacggttgag | 720 |
| gatatatttt tgcttcaaca ttaatatttg tgccctgcac ctgcactgca cgcgagtttg | 780 |
| acgacgtttc gtacagaccc agtagccaac gtgttgtgga gtagcttgtc gtactggcag | 840 |
| gtacaatacc agcaaaccta aaatatggat acgggtgatg acaccgtacc tacagctacc | 900 |
| taccaccctgg tagctgtttg caacactggc ctggcgcgcg cacaccataa ttcttaaatt | 960 |
| tttttgttt ggttattgta gcattttgtt tgtatttgat aattattgtt aatcatggat | 1020 |
| taactaagct caaagaattc atctagcaaa tgacagttaa actgtaccat tagttattat | 1080 |
| ttttgtttat atttaatact tcattatgtg gcgtaagatt cgatgtgatg aagaatctta | 1140 |

```
aaaagttttt tggattttgg ggtaaactaa acaagaacta gttggcgaaa aaatttgggt    1200
ttggctatta tagcactttt gtttaatttg tatttgacaa ttattatccc attaaagact    1260
agctaggctc aaaagattcg tctcgcaaat taaatgcaac ctgtgcaatt agttatttt     1320 taatctatat ttaatgctcc atgtatgtgt ccaaagattt gatgtgacgg aaaattttga    1380
aaaaatagaa aattttttgga actaaacagc ctttataagt gatattattc cgatcaggct   1440
ggaggaaatt gaacagccat gggtttgttt actcatatat aagtgatcga tactgttgat    1500
tattccgatc aggctggagg aaattgaaca gcactacata aacccttggc tttcggttca    1560
ttaagtagta gtagtcttaa tagtagtagt ggtcactagg ttatgtggtg cagtaatttg    1620
aaagcatcca tccatcgcct gcatatactt ttattattgc ttcgagagaa gactcttgca    1680
ctgctttctc atgtcatcaa ctactagtgt acgatgatac tatctagcta actgtggcgg    1740
ttcttgcata tttctatatg ctgctggtcc ttctgcaaga ataaactaat taacactggt    1800 ctcttttttat atgggatgtg ctgtgggtga caacaacaaa aacaggaaca caggccctga   1860
agatgtggtg gtgaaggtgc tctactgtgg aatctgccac acggacatcc accaggccaa    1920
gaaccacctc ggggcttcaa agtaccctat ggtccctggg tgagcacaaa caaacccct     1980 agctagcgat tttattttc agcacattcg ggatcgagta atactctgta tatggtccac     2040
gataaactga attttccagt gttcaattat tcaaactgtc tgaaaagtat aaatgagtag    2100
gacacatata tagcgacatg ccgtttccgc attttgatga gaaaattaca catgcagaca    2160
aatttaggta tatctatctg attgacctgc atagactggt agataggtca gtgcacattt    2220
ggtaactatg aacgtcagca tctcagtccg gagctattct tagatttaca ggtggcacat    2280
accacactaa aactctttgt tacgtagttg gttgccaatt actgtcattc catcagttta    2340
ccaaattatt tgaagcacaa gagtttgttg cgtctaagat gttcttttca tgatagctaa    2400
agagctgcag aaatgagtag taaagcaaac cccaccggcc ggcctatata ccttttttct    2460
gacatgtttg cgagggggaa aaaattaaat aaacataaac ttttcctgac agcacaacca    2520
ctccactact gcgaactgat aatgtgcaca ctagctatca tgggttggtt tttgctaatg    2580
tcgtgtgtct gaaacttttg caggcacgag gtggtcggtg aggtggtgga ggtcgggccc    2640
gaggtgagca agtacggcgt cggcgacgtg gtaggcgtcg gggtgatcgt cgggtgctgc    2700
cgcgagtgca gcccgtgcaa ggccaacgtt gagcagtact gcaacaagaa gatctggtcc    2760
tacaacgatg tctacactga cggccggccc acgcagggcg gcttcgcctc caccatggtc    2820
gtcgaccaga agtgagtttc ttgaaactga aaactaatca tcaggttcat tcagcgttat    2880
cttgcctgca gtgttctagc tagagataat ttcttgtttt tttttaaaaa aaaagttgg     2940 tctgaagtct gaactaagca agaaatagtt gagcttcagt ttgaactttt gtggaagtgg    3000
atggtgatgt ccaatccttc tagaaaaggt ggaggggaga gtatatgggt atgggaaaaa    3060
atttatcatt gagagagtcc atcatcgtcc agctgcaagt cagcgtatgg atgccttgtg    3120
gtgaccaggc aagagtgtga tgtgaaaagt acgacgtggt gtgctttact ggctcatctt    3180
tgtcaagttg aaccataacc acagaagccg aatcctcacc tactactcac tactcatgtc    3240
tgaagattgg tcatccaaac catcactggt tgttgggaga aatggggata actttctcca    3300
tcgtttgatt ccaaacttgc ctgcgacttt agtgtactgt ctttttcagt cagtgggcaa    3360
atcacactac ctaatccaac aactctttga gatagcgatt gcttgttttt ttttaaaaaa    3420
aaaatgggat atatgtgtga attatgatag aacagtaact cctgaagcta ttttatttgg    3480
tgctagttaa atactatcca acaactcttt gagatagcga ttgcttgttg ataattaatg    3540
```

-continued

| | |
|---|---|
| cattttgttt caggtttgtg gtgaagatcc cggcgggtct ggcgccggag caagcggcgc | 3600 |
| cgctgctgtg cgcgggcgta acggtgtaca gcccgctaaa ggccttggg ctgacggccc | 3660 |
| cgggcctccg cggtggcatc gtgggcctgg gcggcgtggg ccacatgggc gtgaaggtgg | 3720 |
| cgaaggccat gggccaccac gtgacggtga tcagctcgtc gtccaagaag cgcgcggagg | 3780 |
| cgatggacca cctgggcgcg gacgcgtacc tggtgagcac ggacgcggcg gccatggcgg | 3840 |
| cggccgccga ctcgctggac tacatcatcg acacggtgcc cgtgcaccac ccgctggagc | 3900 |
| cctacctgtc gctgctgagg ctggacggca agcacgtgct gctgggcgtc atcggcgagc | 3960 |
| ccctcagctt cgtgtccccg atggtgatgc tggggcggaa ggccatcacg gggagcttca | 4020 |
| tcggcagcat cgacgagacc gccgaggtgc tccagttctg cgtcgacaag gggctcacct | 4080 |
| cccagatcga ggtggtcaag atggggtacg tgaacgaggc gctggagcgg ctcgagcgca | 4140 |
| acgacgtccg ctaccgcttc gtcgtcgacg tcgccggcag caacgtcgag gaggatgccg | 4200 |
| ctgatgcgcc gagcaactga cggcgtgcaa cgttcgttcg gggctcgagg ctgcctgcgc | 4260 |
| ttctgcttcc tttagtaatg gtgggcttaa aa | 4292 |

<210> SEQ ID NO 3
<211> LENGTH: 1098
<212> TYPE: DNA
<213> ORGANISM: Sorghum bicolor
<220> FEATURE:
<221> NAME/KEY: misc_feature
<223> OTHER INFORMATION: cDNA
<220> FEATURE:
<221> NAME/KEY: misc_feature
<223> OTHER INFORMATION: Ceres ID No. PI599692-81733680
<220> FEATURE:
<221> NAME/KEY: misc_feature
<223> OTHER INFORMATION: Full length Cinnamyl-alcohol Dehydrogenase
<220> FEATURE:
<221> NAME/KEY: misc_feature
<223> OTHER INFORMATION: Encodes the peptide sequence at SEQ ID NO. 6

<400> SEQUENCE: 3

| | |
|---|---|
| atggggagcc tggcgtccga gaggaaggtg gtcggctggg ccgccaggga cgccaccgga | 60 |
| cacctctccc cctacaccta cccctcagg aacacaggcc ctgaagatgt ggtggtgaag | 120 |
| gtgctctact gtggaatctg ccacacggac atccaccagg ccaagaacca cctcggggct | 180 |
| tcaaagtacc ctatggtccc tgggcacgag gtggtcggtg aggtggtgga ggtcgggccc | 240 |
| gaggtgagca agtacggcgt cggcgacgtg gtaggcgtcg gggtgatcgt cgggtgctgc | 300 |
| cgcgagtgca gcccgtgcaa ggccaacgtt gagcagtact gcaacaagaa gatctggtcc | 360 |
| tacaacgatg tctacactga cggccggccc acgcagggcg gcttcgcctc caccatggtc | 420 |
| gtcgaccaga agtttgtggt gaagatcccg gcgggtctgg cgccggagca agcggcgccg | 480 |
| ctgctgtgcg cgggcgtaac ggtgtacagc ccgctaaagg cctttgggct gacggccccg | 540 |
| ggcctccgcg gtggcatcgt gggcctgggc ggcgtgggcc acatgggcgt gaaggtggcg | 600 |
| aaggccatgg ccaccacgt gacggtgatc agctcgtcgt ccaagaagcg cgcggaggcg | 660 |
| atggaccacc tgggcgcgga cgcgtacctg gtgagcacgg acgcggcggc catggcggcg | 720 |
| gccgccgact cgctggacta catcatcgac acggtgcccg tgcaccaccc gctggagccc | 780 |
| tacctgtcgc tgctgaggct ggacggcaag cacgtgctgc tgggcgtcat cggcgagccc | 840 |
| ctcagcttcg tgtccccgat ggtgatgctg gggcggaagg ccatcacggg gagcttcatc | 900 |
| ggcagcatcg acgagaccgc cgaggtgctc cagttctgcg tcgacaaggg gctcacctcc | 960 |
| cagatcgagg tggtcaagat ggggtacgtg aacgaggcgc tggagcggct cgagcgcaac | 1020 |

```
gacgtccgct accgcttcgt cgtcgacgtc gccggcagca acgtcgagga ggatgccgct    1080
gatgcgccga gcaactga                                                  1098

<210> SEQ ID NO 4
<211> LENGTH: 4298
<212> TYPE: DNA
<213> ORGANISM: Artificial Sequence
<220> FEATURE:
<223> OTHER INFORMATION: Sorghum x Sudangrass
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. 22043-81733671
<220> FEATURE:
<221> NAME/KEY: misc_feature
<223> OTHER INFORMATION: Full length Cinnamyl-alcohol Dehydrogenase
<220> FEATURE:
<221> NAME/KEY: misc_feature
<223> OTHER INFORMATION: Encodes the peptide sequence at SEQ ID NO. 6

<400> SEQUENCE: 4
atggggagcc tggcgtccga gaggaaggtg gtcggctggg ccgccaggga cgccaccgga     60
cacctctccc cctacaccta caccctcagg tacgccgctc cgccgccgcc gccgccactc    120
tagatcgctc gtgttcgtct tctcactttt cctaccccta gtcccctccc ccttcatgtc    180
cgtccgactg tgtctcctgc tccttgtgca aacacgaaaa tagatccagg agaggatgag    240
ggacggtttg gcttgtgcgg cgccttcttc agtgattgtc cgagatcgac caggaacagg    300
aagaacagta aaatctgagt catgattgtg atgatttttt ttttaaaaaa aaaaacagga    360
tatatttccg atccacttcc acgattaggc cggtgcacgt atctaatcgc cggcaggttt    420
taatttggga aggatgctat acgtatgcat attctgatcc atatactata actgatacgt    480
ttacggttat catttaccga gtattccttc tcttgatttc tgtaagatgt tccttatgtt    540
atatgctgtg gtcgtatctt tttcctcaca catactgtag tatactagta caccttagta    600
ggagcactac tccacaacaa acgcatgcat gcgcatgcgc gcggcagcat gcgcatgata    660
ggtcttcaac tccaggtcca actctagtgc cgccgcacat gcatgtatgg atgccacggt    720
tgaggatata ttttgcttca atattaatat ttgtgccctg cacctgcact gcacgtgagt    780
ttgacgacgt tcgtacagga cccagtagcc aacgtgttgt gtggagtagc ttgtcgtact    840
ggcaggtaca ataccagcaa acctaaaata tggatacggg tgatgacacc gtacctacag    900
ctacctacca cctggtagct gttttgcaaca ctggcctggc gcgcgcacac cataattctt    960 aaatttttt tgtttggtta ttgtagcatt ttgtttgtat ttgataatta ttgttaatca    1020
tggattaact aagctcaaag aattcatcta gcaaatgaca gttaaactgt accattagtt    1080 attattttg tttatattta atacttcatt atgtggcgta agattcgatg tgatgaagaa    1140
tcttaaaaag tttttttggat tttggggtaa actaaacaag aactagttgg cgaaaaaatt    1200
tgggtttggc tattatagca cttttgttta atttgtattt gacaattatt atcccattaa    1260
agactagcta ggctcaaaag attcgtctcg caaattaaat gcaacctgtg caattagtta    1320 tttttaatc tatatttaat gctccatgta tgtgtccaaa gatttgatat gacggaaaat    1380
tttgaaaaaa tagaaaattt ttggaactaa acagccttta taagtgatat tattccgatc    1440
aggctggagg aaattgaaca gccatgggtt tgtttactca tatataagtg atcgatactg    1500
ttgattattc cgatcaggct ggaggaaatt gaacagcact acataaaccc ttggctttcg    1560
gttcattaag tagtagtagt cttaatagta gtagtggtca ctaggttatg tggtgcagta    1620
```

```
atttgaaagc atccatccat cgcctgcata tacttttatt attgcttcga gagaagactc   1680
ttgcactgct ttctcatgtc atcaactact agtgtacgat gatactatct agctaactgt   1740
ggcggttctt gcatatttct atatgctgct ggtccttctg caagaataaa ctaattaaca   1800
ctggtctctt tttatatggg atgtgctgtg ggtgacaaca acaaaaacag gaacacaggc   1860
cctgaagatg tggtggtgaa ggtgctctac tgtggaatct gccacacgga catccaccag   1920
gccaagaacc acctcgggc ttcaaagtac cctatggtcc ctgggtgagc acaaacaaac    1980
cccctagcta gcgatttat ttttcagcac ctttgggatc gagtaatact ctgtatatgg    2040
tttacgataa actgaatttt ccagtgttct attattcaaa ctgtctgaaa agtataaatg   2100
aataggacac atatatagcg acatgccgtt tccgcatttt gatgagaaaa ctacacatgc   2160
agacaaattt aggtatatct atctgattga cctgcataga ctggtagata ggtcagtgca   2220
catttggtaa ctacaaacgt cagcatctca gtccgtagct attcttagat ttacaggtgg   2280
cacataccac actaaaactc tttgttacgt agttggttgc caattactgt cattccatca   2340
gtttaccaaa ttatttgaag cacaagagtt tgttgcgtct aagatgttct tttcatgata   2400
gctaaagagc tgcagaaatg agtagtaaag caaaccccac cggccggcct atatacctt    2460 tttctgacat gtttgcgagg gggaaaaaaa ttaaataaac ataaactttt cctgacagca   2520
caaccactcc actactgcga actgataatg tgcacactag ctatcatggg ttggttttg    2580 ctaatgtcgt gtgtctgaaa cttttgcagg cacgaggtgg tcggtgaggt ggtggaggtc   2640
gggcccgagg tgagcaagta cggcgtcggc gacgtggtag gcgtcgggt gatcgtcggg    2700 tgctgccgcg agtgcagccc ctgcaaggcc aacgttgagc agtactgcaa caagaagatc   2760
tggtcctaca acgatgtcta cactgacggc cggcccacgc agggcggctt cgcctccacc   2820
atggtcgtcg accagaagtg agtttcttga aactgaaaac taatcatcag gttcattcag   2880
cgttatcttg cctgcagtgt tctagctaga gataatttct tgttttttt ttttaaaaaa    2940 agttggtctg aagtctgaac taagcaagaa atagttgagc ttcagtttga acttttgtgg   3000
aagtggatgg tgatgtccaa tccttctaga aaggtggag gggagagtat atgggtatgg    3060
gaaaaaattt atcattgaga gagtccatca tcgtccagct gcaagtcagc gtatggatgc   3120
cttgtggtga ccaggcaaga gtgtgatgtg aaaagtacga cgtggtgtgc tttactggct   3180
catctttgtc aagttgaacc ataaccacag aagccgaatc ctcacctact actcactact   3240
catgtctgaa gattggtcat ccaaaccatc actggttgtt gggagaaatg gggataactt   3300
tctccatcgt ttgattccaa acttgcctgc gactttagtg tactgtcttt ttcagtcagt   3360
gggcaaatca cactacctaa tccaacaact cttgagata gcgattgctt gttttttt     3420 aaaaaaaaaa tgggatatat gtgtgaatta tgatagaaca gtaactcctg aagctatttt   3480
atttggtgct agttaaatac tatccaacaa ctctttgaga tagcgattgc ttgttgataa   3540
ttaatgcatt ttgtttcagg tttgtggtga agatcccggc gggtctggcg ccggagcaag   3600
cggcgccgct gctgtgcgcg ggcgtaacgg tgtacagccc gctaaaggcc tttgggctga   3660
cggccccggg cctccgcggt ggcatcgtgg gcctgggcgg cgtgggccac atgggcgtga   3720
aggtggcgaa ggccatgggc caccacgtga cggtgatcag ctcgtcgtcc aagaagcgcg   3780
cggaggcgat ggaccacctg ggcgcggacg cgtacctggt gagcacggac gcggcggcca   3840
tggcggcggc cgccgactcg ctggactaca tcatcgacac ggtgcccgtg caccacccgc   3900
tggagcccta cctgtcgctg ctgaggctgg acggcaagca cgtgctgctg ggcgtcatcg   3960
gcgagcccct cagcttcgtg tccccgatgg tgatgctggg gcggaaggcc atcacgggga   4020
```

-continued

```
gcttcatcgg cagcatcgac gagaccgccg aggtgctcca gttctgcgtc gacaaggggc    4080
tcacctccca gatcgaggtg gtcaagatgg ggtacgtgaa cgaggcgctg gagcggctcg    4140
agcgcaacga cgtccgctac cgcttcgtcg tcgacgtcgc cggcagcaac gtcgaggagg    4200
atgccgctga tgcgccgagc aactgacggc gtgcaacgtt cgttcgggc tcgaggctgc     4260 ctgcgcttct gcttcctta aaatgggggg gcctaaag                              4298
```

<210> SEQ ID NO 5
<211> LENGTH: 1098
<212> TYPE: DNA
<213> ORGANISM: Artificial Sequence
<220> FEATURE:
<221> NAME/KEY: misc_feature
<223> OTHER INFORMATION: Sorghum x Sudangrass
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Ceres ID No. 22043-81733671
<220> FEATURE:
<221> NAME/KEY: misc_feature
<223> OTHER INFORMATION: Full length Cinnamyl-alcohol Dehydrogenase
<220> FEATURE:
<221> NAME/KEY: misc_feature
<223> OTHER INFORMATION: Encodes the peptide sequence at SEQ ID NO. 6

<400> SEQUENCE: 5

```
atggggagcc tggcgtccga gaggaaggtg gtcggctggg ccgccaggga cgccaccgga      60
cacctctccc cctacaccta caccctcagg aacacaggcc ctgaagatgt ggtggtgaag     120
gtgctctact gtggaatctg ccacacggac atccaccagg ccaagaacca cctcggggct     180
tcaaagtacc ctatggtccc tgggcacgag gtggtcggtg aggtggtgga ggtcgggccc     240
gaggtgagca agtacggcgt cggcgacgtg gtaggcgtcg gggtgatcgt cgggtgctgc     300
cgcgagtgca gccctgcaa ggccaacgtt gagcagtact gcaacaagaa gatctggtcc      360
tacaacgatg tctacactga cggccggccc acgcagggcg gcttcgcctc caccatggtc     420
gtcgaccaga gtttgtggt gaagatcccg gcgggtctgg cgccggagca agcggcgccg     480
ctgctgtgcg cgggcgtaac ggtgtacagc ccgctaaagg cctttgggct gacggccccg     540
ggcctccgcg gtggcatcgt gggcctgggc ggcgtgggcc acatgggcgt gaaggtggcg     600
aaggccatgg ccaccacgt gacggtgatc agctcgtcgt ccaagaagcg cgcggaggcg     660
atggaccacc tgggcgcgga cgcgtacctg gtgagcacgg acgcggcggc catggcggcg     720
gccgccgact cgctggacta catcatcgac acggtgcccg tgcaccaccc gctggagccc     780
tacctgtcgc tgctgaggct ggacggcaag cacgtgctgc tgggcgtcat cggcgagccc     840
ctcagcttcg tgtccccgat ggtgatgctg gggcggaagg ccatcacggg gagcttcatc     900
ggcagcatcg acgagaccgc cgaggtgctc cagttctgcg tcgacaaggg gctcacctcc     960
cagatcgagg tggtcaagat ggggtacgtg aacgaggcgc tggagcggct cgagcgcaac    1020
gacgtccgct accgcttcgt cgtcgacgtc gccggcagca acgtcgagga ggatgccgct    1080
gatgcgccga gcaactga                                                  1098
```

<210> SEQ ID NO 6
<211> LENGTH: 365
<212> TYPE: PRT
<213> ORGANISM: Sorghum bicolor
<220> FEATURE:
<221> NAME/KEY: misc_feature
<223> OTHER INFORMATION: GI No. 119852230
<220> FEATURE:

```
<221> NAME/KEY: misc_feature
<223> OTHER INFORMATION: Ceres ID No. PI599692-81733680
<220> FEATURE:
<221> NAME/KEY: misc_feature
<223> OTHER INFORMATION: Ceres ID No. 22043-81733671
<220> FEATURE:
<221> NAME/KEY: misc_feature
<223> OTHER INFORMATION: Full length Cinnamyl-alcohol Dehydrogenase
<220> FEATURE:
<221> NAME/KEY: misc_feature
<222> LOCATION: (34)..(149)
<223> OTHER INFORMATION: Pfam Name: Alcohol dehydrogenase GroES-like
     domain
<220> FEATURE:
<221> NAME/KEY: misc_feature
<222> LOCATION: (165)..(316)
<223> OTHER INFORMATION: Pfam Name: Methyltransferase small domain
<220> FEATURE:
<221> NAME/KEY: misc_feature
<222> LOCATION: (180)..(315)
<223> OTHER INFORMATION: Pfam Name: Zinc-binding dehydrogenase

<400> SEQUENCE: 6

Met Gly Ser Leu Ala Ser Glu Arg Lys Val Val Gly Trp Ala Ala Arg
1               5                   10                  15

Asp Ala Thr Gly His Leu Ser Pro Tyr Thr Tyr Thr Leu Arg Asn Thr
            20                  25                  30

Gly Pro Glu Asp Val Val Lys Val Leu Tyr Cys Gly Ile Cys His
        35                  40                  45

Thr Asp Ile His Gln Ala Lys Asn His Leu Gly Ala Ser Lys Tyr Pro
    50                  55                  60

Met Val Pro Gly His Glu Val Val Gly Glu Val Val Glu Val Gly Pro
65                  70                  75                  80

Glu Val Ser Lys Tyr Gly Val Gly Asp Val Val Gly Val Gly Val Ile
                85                  90                  95

Val Gly Cys Cys Arg Glu Cys Ser Pro Cys Lys Ala Asn Val Glu Gln
            100                 105                 110

Tyr Cys Asn Lys Lys Ile Trp Ser Tyr Asn Asp Val Tyr Thr Asp Gly
        115                 120                 125

Arg Pro Thr Gln Gly Gly Phe Ala Ser Thr Met Val Val Asp Gln Lys
    130                 135                 140

Phe Val Val Lys Ile Pro Ala Gly Leu Ala Pro Glu Gln Ala Ala Pro
145                 150                 155                 160

Leu Leu Cys Ala Gly Val Thr Val Tyr Ser Pro Leu Lys Ala Phe Gly
                165                 170                 175

Leu Thr Ala Pro Gly Leu Arg Gly Gly Ile Val Gly Leu Gly Gly Val
            180                 185                 190

Gly His Met Gly Val Lys Val Ala Lys Ala Met Gly His His Val Thr
        195                 200                 205

Val Ile Ser Ser Ser Lys Lys Arg Ala Glu Ala Met Asp His Leu
    210                 215                 220

Gly Ala Asp Ala Tyr Leu Val Ser Thr Asp Ala Ala Met Ala Ala
225                 230                 235                 240

Ala Ala Asp Ser Leu Asp Tyr Ile Ile Asp Thr Val Pro Val His His
                245                 250                 255

Pro Leu Glu Pro Tyr Leu Ser Leu Leu Arg Leu Asp Gly Lys His Val
            260                 265                 270

Leu Leu Gly Val Ile Gly Glu Pro Leu Ser Phe Val Ser Pro Met Val
        275                 280                 285

Met Leu Gly Arg Lys Ala Ile Thr Gly Ser Phe Ile Gly Ser Ile Asp
    290                 295                 300
```

```
Glu Thr Ala Glu Val Leu Gln Phe Cys Val Asp Lys Gly Leu Thr Ser
305                 310                 315                 320

Gln Ile Glu Val Val Lys Met Gly Tyr Val Asn Glu Ala Leu Glu Arg
            325                 330                 335

Leu Glu Arg Asn Asp Val Arg Tyr Arg Phe Val Val Asp Val Ala Gly
        340                 345                 350

Ser Asn Val Glu Glu Asp Ala Ala Asp Ala Pro Ser Asn
    355                 360                 365

<210> SEQ ID NO 7
<211> LENGTH: 4226
<212> TYPE: DNA
<213> ORGANISM: Sorghum bicolor
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. PI602730-81733686
<220> FEATURE:
<221> NAME/KEY: misc_feature
<223> OTHER INFORMATION: Truncated Cinnamyl-alcohol Dehydrogenase 2
<220> FEATURE:
<221> NAME/KEY: misc_feature
<223> OTHER INFORMATION: BMR-17
<220> FEATURE:
<221> NAME/KEY: misc_feature
<223> OTHER INFORMATION: Encodes the peptide sequence at SEQ ID NO. 9

<400> SEQUENCE: 7
atggggagcc tggcgtccga gaggaaggtg gtcggctggg ccgccaggga cgccaccgga      60
cacctctccc cctacaccta caccctcagg tacgccgctc cgccgccgcc gccgccactc     120
tagatcgctc gtgttcgtct tctcactttt cctacccta gtccctccc ccttcatgtc      180 cgtccgactg tgtctcctgc tccttgtgca aacacgaaaa tagatccagg agaggatgag     240
ggacggtttg gcttgtgcgg cgccttcttc agtgattgtc cgagatcgac caggaacagg     300
aagaacagta aaatctgagt catgattgtg atgatttttt ttttaaaaaa aaaaacagga     360
tatatttccg atccacttcc acgattaggc cggtgcacgt atctaatcgc cggcaggttt     420
taatttggga aggatgctat acgtatgcat attctgatcc atatactata actgatacgt     480
ttacggttat catttaccga gtattccttc tcttgatttc tgtaagatgt tccttatgtt     540
atatgctgtg gtcgtatctt tttcctcaca catactgtag tatactagta caccttagta     600
ggagcactac tccacaacaa acgcatgcat gcgcatgcgc gcggcagcat gcgcatgata     660
ggtcttcaac tccaggtcca actctagtgc cgccgcacat gcatgtatgg atgccacggt     720
tgaggatata ttttgcttca atattaatat ttgtgccctg cacctgcact gcacgtgagt     780
ttgacgacgt ttcgtacaga cccagtagcc aacgtgttgt gtggagtagc ttgtcgtact     840
ggcaggtaca ataccagcaa acctaaaata tggatacggg tgatgacacc gtacctacag     900
ctacctacca cctggtagct gtttgcaaca ctggcctggc gcgcgcacac cataattctt     960 aaatttttt tgtttggtta ttgtagcatt tgtttgtat ttgataatta ttgttaatca     1020
tggattaact aagctcaaag aattcatcta gcaaatgaca gttaaactgt accattagtt     1080
attatttttg tttatattta atacttcatt atgtggcgta agattcgatg tgatgaagaa     1140
tcttaaaaag ttttttggat tttggggtaa actaaacaag aactagttgg cgaaaaaatt     1200
tgggtttggc tattatagca cttttgttta atttgtattt gacaattatt atcccattaa     1260
agactagcta ggctcaaaag attcgtctcg caaattaaat gcaacctgtg caattagtta     1320
```

```
tttttttaatc tatatttaat gctccatgta tgtgtccaaa gatttgatat gacggaaaat    1380
tttgaaaaaa tagaaaattt ttggaactaa acagccttta taagtgatat tattccgatc    1440
aggctggagg aaattgaaca gccatgggtt tgtttactca tatataagtg atcgatactg    1500
ttgattattc cgatcaggct ggaggaaatt gaacagcact acataaaccc ttggctttcg    1560
gttcattaag tagtagtagt cttaatagta gtagtggtca ctaggttatg tggtgcagta    1620
atttgaaagc atccatccat cgcctgcata tacttttatt attgcttcga gagaagactc    1680
ttgcactgct ttctcatgtc atcaactact agtgtacgat gatactatct agctaactgt    1740
ggcggttctt gcatatttct atatgctgct ggtccttctg caagaataaa ctaattaaca    1800
ctggtctctt tttatatggg atgtgctgtg ggtgacaaca acaaaaacag gaacacaggc    1860
cctgaagatg tggtggtgaa ggtgctctac tgtggaatct gccacacgga catccaccag    1920
gccaagaacc acctcggggc ttcaaagtac cctatggtcc ctgggtgagc acaaacaaac    1980
cccctagcta gcgattttat ttttcagcac ctttgggatc gagtaatact ctgtatatgg    2040
tttacgataa actgaatttt ccagtgttct attattcaaa ctgtctgaaa agtataaatg    2100
aataggacac atatatagcg acatgccgtt tccgcatttt gatgagaaaa ctacacatgc    2160
agacaaattt aggtatatct atctgattga cctgcataga ctggtagata ggtcagtgca    2220
catttggtaa ctacaaacgt cagcatctca gtccgtagct attcttagat ttacaggtgg    2280
cacataccac actaaaactc tttgttacgt agttggttgc caattactgt cattccatca    2340
gtttaccaaa ttatttgaag cacaagagtt tgttgcgtct aagatgttct tttcatgata    2400
gctaaagagc tgcagaaatg agtagtaaag caaaccccac cggccggcct atatacccttt    2460 tttctgacat gtttgcgagg gggaaaaaaa ttaaataaac ataaactttt cctgacagca    2520
caaccactcc actactgcga actgataatg tgcacactag ctatcatggg ttggtttttg    2580
ctaatgtcgt gtgtctgaaa cttttgcagg cacgaggtgg tcggtgaggt ggtggaggtc    2640
gggcccgagg tgagcaagta cggcgtcggc gacgtggtag gcgtcgggt gatcgtcggg    2700 tgctgccgcg agtgcagccc ctgcaaggcc aacgttgagc agtactgcaa caagaagatc    2760
tggtcctaca acgatgtcta cactgacggc cggcccacgc agggcggctt cgcctccacc    2820
atggtcgtcg accagaagtg agtttcttga aactgaaaac taatcatcag gttcattcag    2880
cgttatcttg cctgcagtgt tctagctaga gataatttct tgttttttttt ttttaaaaaa    2940 agttggtctg aagtctgaac taagcaagaa atagttgagc ttcagtttga acttttgtgg    3000
aagtggatgg tgatgtccaa tccttctaga aaggtggag gggagagtat atgggtatgg    3060
gaaaaatttt atcattgaga gagtccatca tcgtccagct gcaagtcagc gtatggatgc    3120
cttgtggtga ccaggcaaga gtgtgatgtg aaaagtacga cgtggtgtgc tttactggct    3180
catctttgtc aagttgaacc ataaccacag aagccgaatc ctcacctact actcactact    3240
catgtctgaa gattggtcat ccaaaccatc actggttgtt gggagaaatg gggataactt    3300
tctccatcgt ttgattccaa acttgcctgc gactttagtg tactgtcttt ttcagtcagt    3360
gggcaaatca cactacctaa tccaacaact ctttgagata cgattgcttt gtttttttttt    3420 aaaaaaaaaa tgggatatat gtgtgaatta tgatagaaca gtaactcctg aagctatttt    3480
atttggtgct agttaaatac tatccaacaa ctctttgaga tagcgattgc ttgttgataa    3540
ttaatgcatt ttgtttcagg tttgtggtga agatcccggc gggtctggcg ccggagcaag    3600
cggcgccgct gctgtgcgcg ggcgtaacgg tgtacagccc gctaaaggcc tttgggctga    3660
cggccccggg cctccgcggt ggcatcgtgg gcctgggcgg cgtgggccac atgggcgtga    3720
```

| aggtggcgaa ggccatgggc caccacgtga cggtgatcag ctcgtcgtcc aagaagcgcg | 3780 |
| cggaggcgat ggaccacctg ggcgcggacg cgtacctggt gagcacggac gcggcggcca | 3840 |
| tggcggcggc cgccgactcg ctggactaca tcatcgacac ggtgcccgtg caccaccgc | 3900 |
| tggagcccta cctgtcgctg ctgaggctgg acggcaagca cgtgctgctg ggcgtcatcg | 3960 |
| gcgagcccct cagcttcgtg tccccgatgg tgatgctggg cggaaggcc atcacgggga | 4020 |
| gcttcatcgg cagcatcgac gagaccgccg aggtgctcca gttctgcgtc gacaagggc | 4080 |
| tcacctccta gatcgaggtg gtcaagatgg ggtacgtgaa cgaggcgctg agcggctcg | 4140 |
| agcgcaacga cgtccgctac cgcttcgtcg tcgacgtcgc cggcagcaac gtcgaggagg | 4200 |
| atgccgctga tgcgccgagc aactga | 4226 |

<210> SEQ ID NO 8
<211> LENGTH: 1098
<212> TYPE: DNA
<213> ORGANISM: Sorghum bicolor
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Ceres ID No. PI602730-81733686
<220> FEATURE:
<221> NAME/KEY: misc_feature
<223> OTHER INFORMATION: Truncated Cinnamyl-alcohol Dehydrogenase 2
<220> FEATURE:
<221> NAME/KEY: misc_feature
<223> OTHER INFORMATION: Encodes the peptide sequence at SEQ ID NO. 9

<400> SEQUENCE: 8

| atggggagcc tggcgtccga gaggaaggtg gtcggctggg ccgccaggga cgccaccgga | 60 |
| cacctctccc cctacaccta cccctcagg aacacaggcc ctgaagatgt ggtggtgaag | 120 |
| gtgctctact gtggaatctg ccacacggac atccaccagg ccaagaacca cctcggggct | 180 |
| tcaaagtacc ctatggtccc tgggcacgag gtggtcggtg aggtggtgga ggtcgggccc | 240 |
| gaggtgagca agtacggcgt cggcgacgtg gtaggcgtcg gggtgatcgt cgggtgctgc | 300 |
| cgcgagtgca gccccctgcaa ggccaacgtt gagcagtact gcaacaagaa gatctggtcc | 360 |
| tacaacgatg tctacactga cggccggccc acgcagggcg gcttcgcctc caccatggtc | 420 |
| gtcgaccaga gtttgtggt gaagatcccg gcgggtctgg cgccggagca agcggcgccg | 480 |
| ctgctgtgcg cgggcgtaac ggtgtacagc ccgctaaagg cctttgggct gacggccccg | 540 |
| ggcctccgcg gtggcatcgt gggcctgggc ggcgtgggcc acatgggcgt gaaggtggcg | 600 |
| aaggccatgg gccaccacgt gacggtgatc agctcgtcgt ccaagaagcg cgcggaggcg | 660 |
| atggaccacc tgggcgcgga cgcgtacctg gtgagcacgg acgcggcggc catggcggcg | 720 |
| gccgccgact cgctggacta catcatcgac acggtgcccg tgcaccaccc gctggagccc | 780 |
| tacctgtcgc tgctgaggct ggacggcaag cacgtgctgc tgggcgtcat cggcgagccc | 840 |
| ctcagcttcg tgtccccgat ggtgatgctg gggcggaagg ccatcacggg gagcttcatc | 900 |
| ggcagcatcg acgagaccgc cgaggtgctc cagttctgcg tcgacaaggg gctcacctcc | 960 |
| tagatcgagg tggtcaagat ggggtacgtg aacgaggcgc tggagcggct cgagcgcaac | 1020 |
| gacgtccgct accgcttcgt cgtcgacgtc gccggcagca acgtcgagga ggatgccgct | 1080 |
| gatgcgccga gcaactga | 1098 |

<210> SEQ ID NO 9
<211> LENGTH: 320
<212> TYPE: PRT

```
<213> ORGANISM: Sorghum bicolor
<220> FEATURE:
<221> NAME/KEY: misc_feature
<223> OTHER INFORMATION: Ceres ID No. PI602730-81733686
<220> FEATURE:
<221> NAME/KEY: misc_feature
<223> OTHER INFORMATION: Truncated Cinnamyl-alcohol Dehydrogenase 2
<220> FEATURE:
<221> NAME/KEY: misc_feature
<222> LOCATION: (34)..(149)
<223> OTHER INFORMATION: Pfam Name: Alcohol dehydrogenase GroES-like
      domain
<220> FEATURE:
<221> NAME/KEY: misc_feature
<222> LOCATION: (165)..(316)
<223> OTHER INFORMATION: Pfam Name: Methyltransferase small domain
<220> FEATURE:
<221> NAME/KEY: misc_feature
<222> LOCATION: (180)..(315)
<223> OTHER INFORMATION: Pfam Name: Zinc-binding dehydrogenase

<400> SEQUENCE: 9

Met Gly Ser Leu Ala Ser Glu Arg Lys Val Val Gly Trp Ala Ala Arg
  1               5                  10                  15

Asp Ala Thr Gly His Leu Ser Pro Tyr Thr Tyr Thr Leu Arg Asn Thr
             20                  25                  30

Gly Pro Glu Asp Val Val Lys Val Leu Tyr Cys Gly Ile Cys His
         35                  40                  45

Thr Asp Ile His Gln Ala Lys Asn His Leu Gly Ala Ser Lys Tyr Pro
     50                  55                  60

Met Val Pro Gly His Glu Val Val Gly Glu Val Val Glu Val Gly Pro
 65                  70                  75                  80

Glu Val Ser Lys Tyr Gly Val Gly Asp Val Val Gly Val Gly Val Ile
                 85                  90                  95

Val Gly Cys Cys Arg Glu Cys Ser Pro Cys Lys Ala Asn Val Glu Gln
            100                 105                 110

Tyr Cys Asn Lys Lys Ile Trp Ser Tyr Asn Asp Val Tyr Thr Asp Gly
            115                 120                 125

Arg Pro Thr Gln Gly Gly Phe Ala Ser Thr Met Val Val Asp Gln Lys
        130                 135                 140

Phe Val Val Lys Ile Pro Ala Gly Leu Ala Pro Glu Gln Ala Ala Pro
145                 150                 155                 160

Leu Leu Cys Ala Gly Val Thr Val Tyr Ser Pro Leu Lys Ala Phe Gly
                165                 170                 175

Leu Thr Ala Pro Gly Leu Arg Gly Gly Ile Val Gly Leu Gly Gly Val
            180                 185                 190

Gly His Met Gly Val Lys Val Ala Lys Ala Met Gly His His Val Thr
        195                 200                 205

Val Ile Ser Ser Ser Ser Lys Lys Arg Ala Glu Ala Met Asp His Leu
    210                 215                 220

Gly Ala Asp Ala Tyr Leu Val Ser Thr Asp Ala Ala Met Ala Ala
225                 230                 235                 240

Ala Ala Asp Ser Leu Asp Tyr Ile Ile Asp Thr Val Pro Val His His
                245                 250                 255

Pro Leu Glu Pro Tyr Leu Ser Leu Leu Arg Leu Asp Gly Lys His Val
            260                 265                 270

Leu Leu Gly Val Ile Gly Glu Pro Leu Ser Phe Val Ser Pro Met Val
        275                 280                 285

Met Leu Gly Arg Lys Ala Ile Thr Gly Ser Phe Ile Gly Ser Ile Asp
    290                 295                 300
```

```
Glu Thr Ala Glu Val Leu Gln Phe Cys Val Asp Lys Gly Leu Thr Ser
305                 310                 315                 320
```

<210> SEQ ID NO 10
<211> LENGTH: 4227
<212> TYPE: DNA
<213> ORGANISM: Sorghum bicolor
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. BICOLOR-81733675
<220> FEATURE:
<221> NAME/KEY: misc_feature
<223> OTHER INFORMATION: Cinnamyl-alcohol Dehydrogenase having
      insertional frame shift at position 4020
<220> FEATURE:
<221> NAME/KEY: misc_feature
<223> OTHER INFORMATION: Encodes the peptide sequence at SEQ ID NO. 12

<400> SEQUENCE: 10

```
atggggagcc tggcgtccga aggaaggtg  gtcggctggg ccgccaggga cgccaccgga      60
cacctctccc cctacaccta cccctcagg  tacgccgctc cgccgccgcc gccgccactc     120
tagatcgctc gtgttcgtct tctcactttt cctacccta  gtcccctccc ccttcatgtc     180
cgtccgactg tgtctcctgc tccttgtgca aacacgaaaa tagatccagg agaggatgag     240
ggacggtttg gcttgtgcgg cgccttcttc agtgattgtc cgagatcgac caggaacagg     300
aagaacagta aaatctgagt catgattgtg atgattttt  ttttaaaaaa aaaaacagga     360
tatatttccg atccacttcc acgattaggc cggtgcacgt atctaatcgc cggcaggttt     420
taatttggga aggatgctat acgtatgcat attctgatcc atatactata actgatacgt     480
ttacggttat catttaccga gtattccttc tcttgatttc tgtaagatgt tccttatgtt     540
atatgctgtg gtcgtatctt tttcctcaca catactgtag tatactagta caccttagta     600
ggagcactac tccacaacaa acgcatgcat gcgcatgcgc gcggcagcat gcgcatgata     660
ggtcttcaac tccaggtcca actctagtgc cgccgcacat gcatgtatgg atgccacggt     720
tgaggatata ttttgcttca atattaatat ttgtgccctg cacctgcact gcacgtgagt     780
ttgacgacgt tcgtacagac cccagtagcc aacgtgttgt gtggagtagc ttgtcgtact     840
ggcaggtaca ataccagcaa acctaaaata tggatacggg tgatgacacc gtacctacag     900
ctacctacca cctggtagct gtttgcaaca ctggcctggc gcgcgcacac cataattctt     960
aaatttttt  tgtttggtta ttgtagcatt tgtttgtat  ttgataatta ttgttaatca    1020
tggattaact aagctcaaag aattcatcta gcaaatgaca gttaaactgt accattagtt    1080
attattttg  tttatattta atacttcatt atgtggcgta agattcgatg tgatgaagaa    1140
tcttaaaaag ttttttggat tttggggtaa actaaacaag aactagttgg cgaaaaaatt    1200
tgggtttggc tattatagca cttttgttta atttgtattt gacaattatt atcccattaa    1260
agactagcta ggctcaaaag attcgtctcg caaattaaat gcaacctgtg caattagtta    1320
ttttttaatc tatatttaat gctccatgta tgtgtccaaa gatttgatat gacggaaaat    1380
tttgaaaaaa tagaaaattt ttggaactaa acagcctttta taagtgatat tattccgatc    1440
aggctggagg aaattgaaca gccatgggtt tgtttactca tatataagtg atcgatactg    1500
ttgattattc cgatcaggct ggaggaaatt gaacagcact acataaaccc ttggctttcg    1560
gttcattaag tagtagtagt cttaatagta gtagtggtca ctaggttatg tggtgcagta    1620
atttgaaagc atccatccat cgcctgcata tacttttatt attgcttcga gagaagactc    1680
```

```
ttgcactgct ttctcatgtc atcaactact agtgtacgat gatactatct agctaactgt    1740
ggcggttctt gcatatttct atatgctgct ggtccttctg caagaataaa ctaattaaca    1800
ctggtctctt tttatatggg atgtgctgtg ggtgacaaca acaaaaacag gaacacaggc    1860
cctgaagatg tggtggtgaa ggtgctctac tgtggaatct gccacacgga catccaccag    1920
gccaagaacc acctcggggc ttcaaagtac cctatggtcc ctgggtgagc acaaacaaac    1980
cccctagcta gcgattttat ttttcagcac ctttgggatc gagtaatact ctgtatatgg    2040
tttacgataa actgaatttt ccagtgttct attattcaaa ctgtctgaaa agtataaatg    2100
aataggacac atatatagcg acatgccgtt tccgcatttt gatgagaaaa ctacacatgc    2160
agacaaattt aggtatatct atctgattga cctgcataga ctggtagata ggtcagtgca    2220
catttggtaa ctacaaacgt cagcatctca gtccgtagct attcttagat ttacaggtgg    2280
cacataccac actaaaactc tttgttacgt agttggttgc caattactgt cattccatca    2340
gtttaccaaa ttatttgaag cacaagagtt tgttgcgtct aagatgttct tttcatgata    2400
gctaaagagc tgcagaaatg agtagtaaag caaaccccac cggccggcct atatacccttt    2460 tttctgacat gtttgcgagg gggaaaaaaa ttaaataaac ataaactttt cctgacagca    2520
caaccactcc actactgcga actgataatg tgcacactag ctatcatggg ttggtttttg    2580
ctaatgtcgt gtgtctgaaa cttttgcagg cacgaggtgg tcggtgaggt ggtggaggtc    2640
gggcccgagg tgagcaagta cggcgtcggc gacgtggtag gcgtcggggt gatcgtcggg    2700
tgctgccgcg agtgcagccc ctgcaaggcc aacgttgagc agtactgcaa caagaagatc    2760
tggtcctaca acgatgtcta cactgacggc cggcccacgc agggcggctt cgcctccacc    2820
atggtcgtcg accagaagtg agtttcttga aactgaaaac taatcatcag gttcattcag    2880
cgttatcttg cctgcagtgt tctagctaga gataatttct tgttttttt ttttaaaaaa    2940 agttggtctg aagtctgaac taagcaagaa atagttgagc ttcagtttga acttttgtgg    3000
aagtggatgg tgatgtccaa tccttctaga aaaggtggag gggagagtat atgggtatgg    3060 gaaaaattt atcattgaga gagtccatca tcgtccagct gcaagtcagc gtatggatgc    3120
cttgtggtga ccaggcaaga gtgtgatgtg aaaagtacga cgtggtgtgc tttactggct    3180
catctttgtc aagttgaacc ataaccacag aagccgaatc ctcacctact actcactact    3240
catgtctgaa gattggtcat ccaaaccatc actggttgtt gggagaaatg gggataactt    3300
tctccatcgt ttgattccaa acttgcctgc gactttagtg tactgtcttt ttcagtcagt    3360
gggcaaatca cactacctaa tccaacaact cttttgagata gcgattgctt gtttttttt    3420 aaaaaaaaaa tgggatatat gtgtgaatta tgatagaaca gtaactcctg aagctatttt    3480
atttggtgct agttaaatac tatccaacaa ctctttgaga tagcgattgc ttgttgataa    3540
ttaatgcatt ttgtttcagg tttgtggtga agatcccggc gggtctggcg ccggagcaag    3600
cggcgccgct gctgtgcgcg ggcgtaacgg tgtacagccc gctaaaggcc tttgggctga    3660
cggccccggg cctccgcggt ggcatcgtgg gcctgggcgg cgtgggccac atgggcgtga    3720
aggtggcgaa ggccatgggc caccacgtga cggtgatcag ctcgtcgtcc aagaagcgcg    3780
cggaggcgat ggaccacctg ggcgcggacg cgtacctggt gagcacggac gcggcggcca    3840
tggcggcggc cgccgactcg ctggactaca tcatcgacac ggtgcccgtg caccacccgc    3900
tggagcccta cctgtcgctg ctgaggctgg acggcaagca cgtgctgctg ggcgtcatcg    3960
gcgagcccct cagcttcgtg tccccgatgg tgatgctggg gcggaaggcc atcacggggg    4020
agcttcatcg gcagcatcga cgagaccgcc gaggtgctcc agttctgcgt cgacaagggg    4080
```

```
ctcacctccc agatcgaggt ggtcaagatg gggtacgtga acgaggcgct ggagcggctc    4140
gagcgcaacg acgtccgcta ccgcttcgtc gtcgacgtcg ccggcagcaa cgtcgaggag    4200
gatgccgctg atgcgccgag caactga                                       4227
```

<210> SEQ ID NO 11
<211> LENGTH: 1099
<212> TYPE: DNA
<213> ORGANISM: Sorghum bicolor
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Ceres ID No. BICOLOR-81733675
<220> FEATURE:
<221> NAME/KEY: misc_feature
<223> OTHER INFORMATION: Cinnamyl-alcohol Dehydrogenase having
    insertional frame shift at position 890
<220> FEATURE:
<221> NAME/KEY: misc_feature
<223> OTHER INFORMATION: Encodes the peptide sequence at SEQ ID NO. 12

<400> SEQUENCE: 11

```
atggggagcc tggcgtccga gaggaaggtg gtcggctggg ccgccaggga cgccaccgga     60
cacctctccc cctacaccta cccctcagg aacacaggcc ctgaagatgt ggtggtgaag    120
gtgctctact gtggaatctg ccacacggac atccaccagg ccaagaacca cctcggggct    180
tcaaagtacc ctatggtccc tgggcacgag gtggtcggtg aggtggtgga ggtcgggccc    240
gaggtgagca agtacggcgt cggcgacgtg gtaggcgtcg gggtgatcgt cgggtgctgc    300
cgcgagtgca gccccctgca aggccaacgtt gagcagtact gcaacaagaa gatctggtcc    360
tacaacgatg tctacactga cggccggccc acgcagggcg gcttcgcctc caccatggtc    420
gtcgaccaga agtttgtggt gaagatcccg gcgggtctgg cgccggagca agcggcgccg    480
ctgctgtgcg cgggcgtaac ggtgtacagc ccgctaaagg cctttgggct gacggccccg    540
ggcctccgcg gtggcatcgt gggcctgggc ggcgtgggcc acatgggcgt gaaggtggcg    600
aaggccatgg gccaccacgt gacggtgatc agctcgtcgt ccaagaagcg cgcggaggcg    660
atggaccacc tgggcgcgga cgcgtacctg gtgagcacgg acgcggcggc catggcggcg    720
gccgccgact cgctggacta catcatcgac acggtgcccg tgcaccaccc gctggagccc    780
tacctgtcgc tgctgaggct ggacggcaag cacgtgctgc tgggcgtcat cggcgagccc    840
ctcagcttcg tgtccccgat ggtgatgctg gggcggaagg ccatcacggg ggagcttcat    900
cggcagcatc gacgagaccg ccgaggtgct ccagttctgc gtcgacaagg gctcaccctc    960
ccagatcgag gtggtcaaga tggggtacgt gaacgaggcg ctggagcggc tcgagcgcaa   1020
cgacgtccgc taccgcttcg tcgtcgacgt cgccggcagc aacgtcgagg aggatgccgc   1080
tgatgcgccg agcaactga                                              1099
```

<210> SEQ ID NO 12
<211> LENGTH: 360
<212> TYPE: PRT
<213> ORGANISM: Sorghum bicolor
<220> FEATURE:
<221> NAME/KEY: misc_feature
<223> OTHER INFORMATION: Ceres ID No. BICOLOR-81733675
<220> FEATURE:
<221> NAME/KEY: misc_feature
<223> OTHER INFORMATION: Cinnamyl-alcohol Dehydrogenase having
    insertional frame shift
<220> FEATURE:
<221> NAME/KEY: misc_feature
<222> LOCATION: (34)..(149)

<223> OTHER INFORMATION: Pfam Name: Alcohol dehydrogenase GroES-like domain
<220> FEATURE:
<221> NAME/KEY: misc_feature
<222> LOCATION: (180)..(315)
<223> OTHER INFORMATION: Pfam Name: Zinc-binding dehydrogenase

<400> SEQUENCE: 12

Met Gly Ser Leu Ala Ser Glu Arg Lys Val Gly Trp Ala Ala Arg
1               5                   10                  15

Asp Ala Thr Gly His Leu Ser Pro Tyr Thr Tyr Thr Leu Arg Asn Thr
                20                  25                  30

Gly Pro Glu Asp Val Val Lys Val Leu Tyr Cys Gly Ile Cys His
                35                  40                  45

Thr Asp Ile His Gln Ala Lys Asn His Leu Gly Ala Ser Lys Tyr Pro
50                      55                      60

Met Val Pro Gly His Glu Val Gly Glu Val Val Glu Val Gly Pro
65                  70                  75                  80

Glu Val Ser Lys Tyr Gly Val Gly Asp Val Gly Val Gly Val Ile
                85                  90                  95

Val Gly Cys Cys Arg Glu Cys Ser Pro Cys Lys Ala Asn Val Glu Gln
                100                 105                 110

Tyr Cys Asn Lys Lys Ile Trp Ser Tyr Asn Asp Val Tyr Thr Asp Gly
                115                 120                 125

Arg Pro Thr Gln Gly Gly Phe Ala Ser Thr Met Val Val Asp Gln Lys
            130                 135                 140

Phe Val Val Lys Ile Pro Ala Gly Leu Ala Pro Glu Gln Ala Ala Pro
145                 150                 155                 160

Leu Leu Cys Ala Gly Val Thr Val Tyr Ser Pro Leu Lys Ala Phe Gly
                165                 170                 175

Leu Thr Ala Pro Gly Leu Arg Gly Ile Val Gly Leu Gly Gly Val
                180                 185                 190

Gly His Met Gly Val Lys Val Ala Lys Ala Met Gly His His Val Thr
                195                 200                 205

Val Ile Ser Ser Ser Lys Lys Arg Ala Glu Ala Met Asp His Leu
                210                 215                 220

Gly Ala Asp Ala Tyr Leu Val Ser Thr Asp Ala Ala Met Ala Ala
225                 230                 235                 240

Ala Ala Asp Ser Leu Asp Tyr Ile Ile Asp Thr Val Pro Val His His
                245                 250                 255

Pro Leu Glu Pro Tyr Leu Ser Leu Leu Arg Leu Asp Gly Lys His Val
                260                 265                 270

Leu Leu Gly Val Ile Gly Glu Pro Leu Ser Phe Val Ser Pro Met Val
                275                 280                 285

Met Leu Gly Arg Lys Ala Ile Thr Gly Glu Leu His Arg Gln His Arg
290                 295                 300

Arg Asp Arg Arg Gly Ala Pro Val Leu Arg Arg Gln Gly Ala His Leu
305                 310                 315                 320

Pro Asp Arg Gly Gly Gln Asp Gly Val Arg Glu Arg Gly Ala Gly Ala
                325                 330                 335

Ala Arg Ala Gln Arg Arg Pro Leu Pro Leu Arg Arg Arg Arg Arg
            340                 345                 350

Gln Gln Arg Arg Gly Gly Cys Arg
            355                 360

<210> SEQ ID NO 13

```
<211> LENGTH: 4298
<212> TYPE: DNA
<213> ORGANISM: Sorghum bicolor
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. PI535790-81733677
<220> FEATURE:
<221> NAME/KEY: misc_feature
<223> OTHER INFORMATION: Truncated Cinnamyl-alcohol Dehydrogenase 1
<220> FEATURE:
<221> NAME/KEY: misc_feature
<223> OTHER INFORMATION: BMR-6
<220> FEATURE:
<221> NAME/KEY: misc_feature
<223> OTHER INFORMATION: Encodes the peptide sequence at SEQ ID NO. 15

<400> SEQUENCE: 13
atggggagcc tggcgtccga gaggaaggtg gtcggctggg ccgccaggga cgccaccgga      60
cacctctccc cctacaccta cccctcagg tacgccgctc cgccgccgcc gccgccactc     120
tagatcgctc gtgttcgtct tctcactttt cctaccccta gtcccctccc ccttcatgtc     180
cgtccgactg tgtctcctgc tccttgtgca aacacgaaaa tagatccagg agaggatgag     240
ggacggtttg gcttgtgcgg cgccttcttc agtgattgtc cgagatcgac caggaacagg     300
aagaacagta aaatctgagt catgattgtg atgattttt tttttaaaaa aaaaacagga     360
tatatttccg atccacttcc acgattaggc cggtgcacgt atctaatcgc cggcaggttt     420
taatttggga aggatgctat acgtatgcat attctgatcc atatactata actgatacgt     480
ttacggttat catttaccga gtattccttc tcttgatttc tgtaagatgt tccttatgtt     540
atatgctgtg gtcgtatctt tttcctcaca catactgtag tatactagta caccttagta     600
ggagcactac tccacaacaa acgcatgcat gcgcatgcgc gcggcagcat gcgcatgata     660
ggtcttcaac tccaggtcca actctagtgc cgccgcacat gcatgtatgg atgccacggt     720
tgaggatata ttttgcttca atattaatat ttgtgccctg cacctgcact gcacgtgagt     780
ttgacgacgt ttcgtacaga cccagtagcc aacgtgttgt gtggagtagc ttgtcgtact     840
ggcaggtaca ataccagcaa acctaaaata tggatacggg tgatgacacc gtacctacag     900
ctacctacca cctggtagct gttttgcaaca ctggcctggc gcgcgcacac cataattctt     960
aaattttttt tgtttggtta ttgtagcatt ttgtttgtat ttgataatta ttgttaatca    1020
tggattaact aagctcaaag aattcatcta gcaaatgaca gttaaactgt accattagtt    1080 attattttttg tttatattta atacttcatt atgtggcgta agattcgatg tgatgaagaa    1140
tcttaaaaag tttttttggat tttggggtaa actaaacaag aactagttgg cgaaaaaatt    1200
tgggtttggc tattatagca cttttgttta atttgtattt gacaattatt atcccattaa    1260
agactagcta ggctcaaaag attcgtctcg caaattaaat gcaacctgtg caattagtta    1320
ttttttaatc tatatttaat gctccatgta tgtgtccaaa gatttgatat gacggaaaat    1380
tttgaaaaaa tagaaaattt ttggaactaa acagccttta taagtgatat tattccgatc    1440
aggctggagg aaattgaaca gccatgggtt tgtttactca tatataagtg atcgatactg    1500
ttgattattc cgatcaggct ggaggaaatt gaacagcact acataaaccc ttggctttcg    1560
gttcattaag tagtagtagt cttaatagta gtagtggtca ctaggttatg tggtgcagta    1620
atttgaaagc atccatccat cgcctgcata tactttttatt attgcttcga gagaagactc    1680
ttgcactgct ttctcatgtc atcaactact agtgtacgat gatactatct agctaactgt    1740
ggcggttctt gcatatttct atatgctgct ggtccttctg caagaataaa ctaattaaca    1800
```

```
ctggtctctt tttatatggg atgtgctgtg ggtgacaaca acaaaaacag gaacacaggc    1860
cctgaagatg tggtggtgaa ggtgctctac tgtggaatct gccacacgga catccaccag    1920
gccaagaacc acctcgggc ttcaaagtac cctatggtcc ctgggtgagc acaaacaaac     1980
cccctagcta gcgattttat ttttcagcac ctttgggatc gagtaatact ctgtatatgg    2040
tttacgataa actgaatttt ccagtgttct attattcaaa ctgtctgaaa agtataaatg    2100
aataggacac atatatagcg acatgccgtt tccgcatttt gatgagaaaa ctacacatgc    2160
agacaaattt aggtatatct atctgattga cctgcataga ctggtagata ggtcagtgca    2220
catttggtaa ctacaaacgt cagcatctca gtccgtagct attcttagat ttacaggtgg    2280
cacataccac actaaaactc tttgttacgt agttggttgc caattactgt cattccatca    2340
gtttaccaaa ttatttgaag cacaagagtt tgttgcgtct aagatgttct tttcatgata    2400
gctaaagagc tgcagaaatg agtagtaaag caaaccccac cggccggcct atatacctttt   2460 tttctgacat gtttgcgagg gggaaaaaaa ttaaataaac ataaactttt cctgacagca    2520
caaccactcc actactgcga actgataatg tgcacactag ctatcatggg ttggttttttg   2580 ctaatgtcgt gtgtctgaaa cttttgcagg cacgaggtgg tcggtgaggt ggtggaggtc    2640
gggcccgagg tgagcaagta cggcgtcggc gacgtggtag gcgtcggggt gatcgtcggg    2700
tgctgccgcg agtgcagccc ctgcaaggcc aacgttgagc agtactgcaa caagaagatc    2760
tggtcctaca acgatgtcta cactgacggc cggcccacgt agggcggctt cgcctccacc    2820
atggtcgtcg accagaagtg agtttcttga aactgaaaac taatcatcag gttcattcag    2880
cgttatcttg cctgcagtgt tctagctaga gataatttct tgtttttttt ttttaaaaaa    2940
agttggtctg aagtctgaac taagcaagaa atagttgagc ttcagtttga acttttgtgg    3000
aagtggatgg tgatgtccaa tccttctaga aaaggtggag gggagagtat atgggtatgg    3060 gaaaaattt atcattgaga gagtccatca tcgtccagct gcaagtcagc gtatggatgc     3120
cttgtggtga ccaggcaaga gtgtgatgtg aaaagtacga cgtggtgtgc tttactggct    3180
catctttgtc aagttgaacc ataaccacag aagccgaatc ctcacctact actcactact    3240
catgtctgaa gattggtcat ccaaaccatc actggttgtt gggagaaatg gggataactt    3300
tctccatcgt ttgattccaa acttgcctgc gactttagtg tactgtcttt ttcagtcagt    3360
gggcaaatca cactacctaa tccaacaact cttttgagata gcgattgctt gtttttttttt  3420 aaaaaaaaaa tgggatatat gtgtgaatta tgatagaaca gtaactcctg aagctattttt   3480 atttggtgct agttaaatac tatccaacaa ctctttgaga tagcgattgc ttgttgataa    3540
ttaatgcatt ttgtttcagg tttgtggtga agatcccggc gggtctggcg ccggagcaag    3600
cggcgccgct gctgtgcgcg ggcgtaacgg tgtacagccc gctaaaggcc tttgggctga    3660 cggcccggg cctccgcggt ggcatcgtgg gcctgggcgg cgtgggccac atgggcgtga     3720
aggtggcgaa ggccatgggc caccacgtga cggtgatcag ctcgtcgtcc aagaagcgcg    3780
cggaggcgat ggaccacctg gcgcggacg cgtacctggt gagcacggac gcggcggcca    3840
tggcggcggc cgccgactcg ctggactaca tcatcgacac ggtgcccgtg caccacccgc    3900
tggagcccta cctgtcgctg ctgaggctga acggcaagca cgtgctgctg ggcgtcatcg    3960
gcgagcccct cagcttcgtg tccccgatgg tgatgctggg gcggaaggcc atcacgggga    4020
gcttcatcgg cagcatcgac gagaccgccg aggtgctcca gttctgcgtc gacaaggggc    4080
tcacctccca gatcgaggtg gtcaagatgg ggtacgtgaa cgaggcgctg gagcggctcg    4140
agcgcaacga cgtccgctac cgcttcgtcg tcgacgtcgc cggcagcaac gtcgaggagg    4200
```

```
atgccgctga tgcgccgagc aactgacggc gtgcaacgtt cgttcgggc tcgaggctgc   4260 ctgcgcttct gcttccttta gtaattgtgg gcttaaaa                          4298

<210> SEQ ID NO 14
<211> LENGTH: 1098
<212> TYPE: DNA
<213> ORGANISM: Sorghum bicolor
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Ceres ID No. PI535790-81733677
<220> FEATURE:
<221> NAME/KEY: misc_feature
<223> OTHER INFORMATION: Truncated Cinnamyl-alcohol Dehydrogenase 1
<220> FEATURE:
<221> NAME/KEY: misc_feature
<223> OTHER INFORMATION: Encodes the peptide sequence at SEQ ID NO. 15

<400> SEQUENCE: 14
atggggagcc tggcgtccga gaggaaggtg gtcggctggg ccgccaggga cgccaccgga    60
cacctctccc cctacaccta cccctcagg aacacaggcc ctgaagatgt ggtggtgaag   120
gtgctctact gtggaatctg ccacacggac atccaccagg ccaagaacca cctcggggct   180
tcaaagtacc ctatggtccc tgggcacgag gtggtcggtg aggtggtgga ggtcgggccc   240
gaggtgagca agtacggcgt cggcgacgtg gtaggcgtcg gggtgatcgt cgggtgctgc   300
cgcgagtgca gccctgcaa ggccaacgtt gagcagtact gcaacaagaa gatctggtcc   360
tacaacgatg tctacactga cggccggccc acgtagggcg gcttcgcctc caccatggtc   420
gtcgaccaga gtttgtggt gaagatcccg gcgggtctgg cgccggagca gcggcgccg    480 ctgctgtgcg cgggcgtaac ggtgtacagc ccgctaaagg cctttgggct gacggccccg   540
ggcctccgcg gtggcatcgt gggcctgggc ggcgtgggcc acatgggcgt gaaggtggcg   600
aaggccatgg ccaccacgt gacggtgatc agctcgtcgt ccaagaagcg cgcggaggcg   660
atggaccacc tgggcgcgga cgcgtacctg gtgagcacgg acgcggcggc catggcggcg   720
gccgccgact cgctggacta catcatcgac acggtgcccg tgcaccaccc gctggagccc   780
tacctgtcgc tgctgaggct ggacggcaag cacgtgctgc tgggcgtcat cggcgagccc   840
ctcagcttcg tgtccccgat ggtgatgctg gggcggaagg ccatcacggg gagcttcatc   900
ggcagcatcg acgagaccgc cgaggtgctc cagttctgcg tcgacaaggg gctcaccct   960 cagatcgagg tggtcaagat ggggtacgtg aacgaggcgc tggagcggct cgagcgcaac  1020
gacgtccgct accgcttcgt cgtcgacgtc gccggcagca acgtcgagga ggatgccgct  1080
gatgcgccga gcaactga                                              1098

<210> SEQ ID NO 15
<211> LENGTH: 131
<212> TYPE: PRT
<213> ORGANISM: Sorghum bicolor
<220> FEATURE:
<221> NAME/KEY: misc_feature
<223> OTHER INFORMATION: Ceres ID No. PI535790-81733677
<220> FEATURE:
<221> NAME/KEY: misc_feature
<223> OTHER INFORMATION: Truncated Cinnamyl-alcohol Dehydrogenase 1
<220> FEATURE:
<221> NAME/KEY: misc_feature
<222> LOCATION: (34)..(114)
<223> OTHER INFORMATION: Pfam Name: Alcohol dehydrogenase GroES-like
      domain
```

<400> SEQUENCE: 15

```
Met Gly Ser Leu Ala Ser Glu Arg Lys Val Val Gly Trp Ala Ala Arg
1               5                   10                  15

Asp Ala Thr Gly His Leu Ser Pro Tyr Thr Tyr Thr Leu Arg Asn Thr
            20                  25                  30

Gly Pro Glu Asp Val Val Lys Val Leu Tyr Cys Gly Ile Cys His
        35                  40                  45

Thr Asp Ile His Gln Ala Lys Asn His Leu Gly Ala Ser Lys Tyr Pro
50                  55                  60

Met Val Pro Gly His Glu Val Val Gly Glu Val Val Glu Val Gly Pro
65                  70                  75                  80

Glu Val Ser Lys Tyr Gly Val Gly Asp Val Val Gly Val Gly Val Ile
                85                  90                  95

Val Gly Cys Cys Arg Glu Cys Ser Pro Cys Lys Ala Asn Val Glu Gln
            100                 105                 110

Tyr Cys Asn Lys Lys Ile Trp Ser Tyr Asn Asp Val Tyr Thr Asp Gly
        115                 120                 125

Arg Pro Thr
    130
```

<210> SEQ ID NO 16
<211> LENGTH: 2829
<212> TYPE: DNA
<213> ORGANISM: Sorghum bicolor
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. BTx623-85889356
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<223> OTHER INFORMATION: Encodes the peptide sequence at SEQ ID NO. 18

<400> SEQUENCE: 16

```
atgggtcga cggcggagga cgtggcggcg gtggcggacg aggaggcgtg catgtacgcg      60
atgcagctgg cgtcgtcgtc gatcctcccc atgacgctga agaacgcgct ggagctgggc     120
ctgctggagg tgcttcagaa ggacgccggc aaggcgctgg cggcggagga ggtggtggcg     180
cggctgcccg tggcgccgac gaaccccgcc gcggcggaca tggtggaccg catgctccgc     240
ctcctcgcct cctacgacgt cgtgaagtgc agatggagg acaaggacgg caagtacgag      300
cgtcggtact ccgccgcccc cgtcggcaag tggctcaccc ctaacgagga cggcgtctcc     360
atggccgccc tcgcgctcat gaaccaggac aaggtcctca tggagagctg gtgagtagtc     420
gtcgtcagag cacatctcgc cccacctcac catttcatct gtagatcagt tgttgctttg     480
ctgttgatat gatgctggcg tgctagctgc atgatgatga gctcgctcat cattagtact     540
agctagtgat ttattttgtc atttaatttt ttccaagtaa aattgattga ggtgcactac     600
tagtactagc tgctagtaca aagctggcag tagtttaagtt atccatgata taatatttga    660
ctaaaacaaa aaaatatttt ttttacaaaa aagggaagt aagctcaagt tcttcctaaa      720
aaaatgtaga gtaggatgga aaagtaagca aaggacggac cacttgtcat ctccactatc    780
cagtgggcga gacttcggcg aaccttggag aaggagagca ttattggcca actctctctc    840 taatttttt ttcctggatt cgcaaaactg gagccgtcga tcgccggact tattactgac    900
ggctcacatg gatcatggaa ttctgcgaaa ttcctgatct agactttgc gaaactccgt    960
```

-continued

```
tcagtcattc accaactgat ggtgaatctt cagactctca aattgtttgg tgtttggtgt     1020
gtgtgaagtg ggtgtagaaa agaggcagtt ggaccacagg cgactgactg acccattacc     1080
atgtcactga tgctgataga ttcttgccct gttccttta gaaacttttg cacagatcga      1140
tatctgtagc agttttcctt tcatgcaatt tttgactagt ttaaaatgtt cagaccggac     1200
agtgacttca gagttcagac acatgggcct tgtttagtta ggccctgttt agttccccac     1260
aaaaaaaaat ttcatccatc ccatcgaatc tttgaacaca tgcatggaac attaaatgta    1320
aataaaaaat aaactaatta cacagtttgg ttgaaaatcg cgagacgaat cttttaagcc     1380
tagttagtcc atgattagcc ttaagtgcta cagtaaccta catgtgctaa tgacagatta    1440
attatagtta atagatttgt cttgcagttt cctgatgagc tatgtaattt gttttttat      1500 tagttttaa aaaccctcc cgacatcatt ctgacatatc cgatgtgaca tccaaaaatt       1560
tttcattcac aatctaaaca gatccttacc aaaaaatt tgcaaaatct ttcagattct      1620
ccgtcacatc aaatctttag acgcatgcat aaaatatta acatagtcaa aataaaaac      1680 taattacaaa gtttagtcgg aattgacgag acgaatcttt tgagtctagt tagtctatga    1740
ttggataata tttgtcaaat acaaacaaaa atggtactat tttatttg caaattttt       1800 tgaactaaac aaggccatgg cagcagtaac agtccattat tctacatggg catggcgttg    1860
tgctgtagtg cctgcaagta gcagttgtta ccatacacac atgtctgttc tgcatcatca    1920
ctctggtcca ttccgaagtg ctcaagccta taacatccct ttccataatt aaccatacgt    1980
gtctagtagc atagttatca aattcttgca aaaacacaca catatctgac tatctgtaca    2040
attcatcaaa attcttagaa attgaaatcc atgtcgatcg atcagtgctg tgtacgtgtc    2100
tcatcactat ctatctatct atctatctat ctatctatca atcatcacag gtactacctg    2160
aaggacgcgg tgcttgacgg cggcatcccg ttcaacaagg cgtacgggat gacggcgttc    2220
gagtaccacg gcacggaccc gcgcttcaac cgcgtgttca acgagggcat gaagaaccac    2280
agcgtgatca tcaccaagaa gctcctcgag ttctacacgg gcttcgacga gtccgtctcg    2340
acgctcgtcg acgtgggcgg cggcatcggc gccaccttac acgccatcac ctcccaccac    2400
tcccacatca ggggcgtcaa cttcgacctc ccccacgtga tctccgaggc gccgccgttc    2460
cccggcgtgc agcacgtcgg cggggacatg ttcaagtcgg tgccggccgg cgacgccatc    2520
ctcatgaagt ggatcctcca cgactggagc gacgcgcact gcgccacgct gctcaagaac    2580
tgctacgacg cgctgccgga aagggcggc aaggtgatcg tcgtcgagtg cgtgctgccg     2640
gtgaccaccg acgccgtccc caaggcgcag ggcgtgttcc atgtcgacat gatcatgctc    2700
gcgcataacc ccggcggcag ggagcggtac gagcgggagt ccgtgacct cgccaaggcc    2760 gctggcttct ctgggttcaa ggccacctac atctacgcca acgcctgggc catcgagttc    2820
atcaagtaa                                                             2829
```

<210> SEQ ID NO 17
<211> LENGTH: 1089
<212> TYPE: DNA
<213> ORGANISM: Sorghum bicolor
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Ceres ID No. BTx623-85889356
<220> FEATURE:
<221> NAME/KEY: misc_feature
<223> OTHER INFORMATION: Full length Caffeic Acid O-Methyltransferase
<220> FEATURE:

<221> NAME/KEY: misc_feature
<223> OTHER INFORMATION: Encodes the peptide sequence at SEQ ID NO. 18

<400> SEQUENCE: 17

```
atggggtcga cggcggagga cgtggcggcg gtggcggacg aggaggcgtg catgtacgcg      60
atgcagctgg cgtcgtcgtc gatcctcccc atgacgctga agaacgcgct ggagctgggc     120
ctgctggagg tgcttcagaa ggacgccggc aaggcgctgg cggcggagga ggtggtggcg     180
cggctgcccg tggcgccgac gaaccccgcc gcggcggaca tggtggaccg catgctccgc     240
ctcctcgcct cctacgacgt cgtgaagtgc cagatggagg acaaggacgg caagtacgag     300
cgtcggtact ccgccgcccc cgtcggcaag tggctcaccc ctaacgagga cggcgtctcc     360
atggccgccc tcgcgctcat gaaccaggac aaggtcctca tggagagctg gtactacctg     420
aaggacgcgg tgcttgacgg cggcatcccg ttcaacaagg cgtacgggat gacggcgttc     480
gagtaccacg gcacggaccc cgcgcttcaa cgcgtgttca acgagggcat gaagaaccac     540
agcgtgatca tcaccaagaa gctcctcgag ttctacacgg gcttcgacga gtccgtctcg     600
acgctcgtcg acgtgggcgg cggcatcggc gccaccttac acgccatcac ctcccaccac     660
tcccacatca gggcgtcaa cttcgacctc cccacgtga tctccgaggc gccgccgttc       720
cccggcgtgc agcacgtcgg cggggacatg ttcaagtcgg tgccggccgg cgacgccatc     780
ctcatgaagt ggatcctcca cgactggagc gacgcgcact cgccacgct gctcaagaac      840
tgctacgacg cgctgccgga agggcggc aaggtgatcg tcgtcgagtg cgtgctgccg        900
gtgaccaccg acgccgtccc caaggcgcag ggcgtgttcc atgtcgacat gatcatgctc     960
gcgcataacc ccggcggcag ggagcggtac gagcgggagt ccgtgacct cgccaaggcc     1020
gctggcttct ctgggttcaa ggccacctac atctacgcca acgcctgggc catcgagttc    1080
atcaagtaa                                                           1089
```

<210> SEQ ID NO 18
<211> LENGTH: 362
<212> TYPE: PRT
<213> ORGANISM: Sorghum bicolor
<220> FEATURE:
<221> NAME/KEY: misc_feature
<223> OTHER INFORMATION: Ceres ID No. BTx623-85889356
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<222> LOCATION: (31)..(83)
<223> OTHER INFORMATION: Pfam Name: Dimerisation domain
<220> FEATURE:
<221> NAME/KEY: misc_feature
<222> LOCATION: (92)..(339)
<223> OTHER INFORMATION: Pfam Name: O-methyltransferase

<400> SEQUENCE: 18

```
Met Gly Ser Thr Ala Glu Asp Val Ala Ala Val Ala Asp Glu Glu Ala
1               5                   10                  15

Cys Met Tyr Ala Met Gln Leu Ala Ser Ser Ser Ile Leu Pro Met Thr
            20                  25                  30

Leu Lys Asn Ala Leu Glu Leu Gly Leu Leu Glu Val Leu Gln Lys Asp
        35                  40                  45

Ala Gly Lys Ala Leu Ala Ala Glu Glu Val Val Ala Arg Leu Pro Val
    50                  55                  60

Ala Pro Thr Asn Pro Ala Ala Ala Asp Met Val Asp Arg Met Leu Arg
65                  70                  75                  80
```

```
Leu Leu Ala Ser Tyr Asp Val Val Lys Cys Gln Met Glu Asp Lys Asp
                85                  90                  95

Gly Lys Tyr Glu Arg Arg Tyr Ser Ala Ala Pro Val Gly Lys Trp Leu
            100                 105                 110

Thr Pro Asn Glu Asp Gly Val Ser Met Ala Ala Leu Ala Leu Met Asn
        115                 120                 125

Gln Asp Lys Val Leu Met Glu Ser Trp Tyr Tyr Leu Lys Asp Ala Val
    130                 135                 140

Leu Asp Gly Gly Ile Pro Phe Asn Lys Ala Tyr Gly Met Thr Ala Phe
145                 150                 155                 160

Glu Tyr His Gly Thr Asp Pro Arg Phe Asn Arg Val Phe Asn Glu Gly
                165                 170                 175

Met Lys Asn His Ser Val Ile Ile Thr Lys Lys Leu Leu Glu Phe Tyr
            180                 185                 190

Thr Gly Phe Asp Glu Ser Val Ser Thr Leu Val Asp Val Gly Gly Gly
        195                 200                 205

Ile Gly Ala Thr Leu His Ala Ile Thr Ser His His Ser His Ile Arg
    210                 215                 220

Gly Val Asn Phe Asp Leu Pro His Val Ile Ser Glu Ala Pro Pro Phe
225                 230                 235                 240

Pro Gly Val Gln His Val Gly Gly Asp Met Phe Lys Ser Val Pro Ala
                245                 250                 255

Gly Asp Ala Ile Leu Met Lys Trp Ile Leu His Asp Trp Ser Asp Ala
            260                 265                 270

His Cys Ala Thr Leu Leu Lys Asn Cys Tyr Asp Ala Leu Pro Glu Lys
        275                 280                 285

Gly Gly Lys Val Ile Val Glu Cys Val Leu Pro Val Thr Thr Asp
    290                 295                 300

Ala Val Pro Lys Ala Gln Gly Val Phe His Val Asp Met Ile Met Leu
305                 310                 315                 320

Ala His Asn Pro Gly Gly Arg Glu Arg Tyr Glu Arg Glu Phe Arg Asp
                325                 330                 335

Leu Ala Lys Ala Ala Gly Phe Ser Gly Phe Lys Ala Thr Tyr Ile Tyr
            340                 345                 350

Ala Asn Ala Trp Ala Ile Glu Phe Ile Lys
        355                 360

<210> SEQ ID NO 19
<211> LENGTH: 2822
<212> TYPE: DNA
<213> ORGANISM: Sorghum bicolor
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. PI599692-85802570
<220> FEATURE:
<221> NAME/KEY: misc_feature
<223> OTHER INFORMATION: Truncated Caffeic Acid O-Methyltransferase 1
<220> FEATURE:
<221> NAME/KEY: misc_feature
<223> OTHER INFORMATION: Encodes the peptide sequence at SEQ ID NO. 21

<400> SEQUENCE: 19 atgggtcga  cggcggagga  cgtggcggcg  gtggcggacg  aggaggcgtg  catgtacgcg    60
atgcagctgg  cgtcgtcgtc  gatcctcccc  atgacgctga  agaacgcgct  ggagctgggc   120
ctgctggagg  tgcttcagaa  ggacgccggc  aaggcgctgg  cggcgaggga  ggtggtggcg   180
```

```
cggctgcccg tggcgccgac gaaccccgcc gcggcggaca tggtggaccg catgctccgc    240
ctcctcgcct cctacgacgt cgtgaggtgc cagatggagg acaaggacgg caagtacgag    300
cgtcggtact ccgccgcccc cgtcggcaag tagctcaccc ctaacgagga cggcgtctcc    360
atggccgccc tcgcgctcat gaaccaggac aaggtcctca tggagagctg gtgagtagtc    420
gtcgtcagag cacatctcgc cccacctcac catttcatct gtagatcagt tgttgctttg    480
ctgttgatat gatgctggcg tgctagctgc atgatgatga gctcgctcat cattagtact    540
agctagtgat ttatttttgtc atttaatttt ttccaagtaa aattgattga ggtgcactac    600
tagtactagc tgctagtaca aagctggcag tagttaagtt atccatgata taatatttga    660
ctaaaacaaa aaaatatttt ttttacaaa aaagggaag taagctcaag ttcttcctaa    720
aaaaatgtag agtaggatgg aaaagtaagc aaaggacgga ccacttgtca tctccactat    780
ccagtgggcg agacttcggc gaaccttgga gaaggagagc attattggcc aactctctct    840 ctaattttt tttcctggat tcgcaaaact ggagccgtcg atcgccggac ttattactga    900
cggctcacat ggatcatgga attctgcgaa attcctgatc tagacttttg cgaaactccg    960
ttcagtcatt caccaactga tggtgaatct tcagactctc aaattgtttg gtgtttggtg   1020
tgtgtgaagt gggtgtagaa agaggcagt tggaccacag gcgactgact gacccattac   1080
catgtcactg atgctgatag attcttgccc tgttccttt agaaactttt gcacagatcg   1140
atatctgtag cagttttcct ttcatgcaat ttttgactag tttaaaatgt tcagaccgga   1200
cagtgacttc agagttcaga cacatgggcc ttgtttagtt aggccctgtt tagttcccca   1260
caaaaaaaaa tttcatccat cccatcgaat ctttgaacac atgcatggaa cattaaatgt   1320
aaataaaaaa taaactaatt acacagtttg gttgaaaatc gcgagacgaa tcttttaagc   1380
ctagttagtc catgattagc cttaagtgct acagtaacct acatgtgcta atgacagatt   1440
aattatagtt aatagatttg tcttgcagtt cctgatgag ctatgtaatt tgtttttta   1500 ttagttttta aaacccctc ccgacatcat tctgacatat ccgatgtgac atccaaaaat   1560 tttcattca caatctaaac agatccttac caaaaaatt ttgcaaaatc tttcagattc   1620
tccgtcacat caaatcttta gacgcatgca taaaatatta aacatagtca aaaataaaaa   1680
ctaattacaa agtttagtcg gaattgacga gacgaatctt ttgagtctag ttagtctatg   1740
attggataat atttgtcaaa tacaaacaaa atggtacta ttttttatttt gcaaattttt   1800 ttgaactaaa caaggccatg gcagcagtaa cagtccatta ttctacatgg gcatggcgtt   1860
gtgctgtagt gcctgcaagt agcagttgtt accatacaca catgtctgtt ctgcatcatc   1920
actctggtcc attccgaagt gctcaagcct ataacatccc tttccataat taaccatacg   1980
tgtctagtag catagttatc aaattcttgc aaaaacacac acatatctga ctatctgtac   2040
aattcatcaa aattcttaga aattgaaatc catgtcgatc gatcagtgct gtgtacgtgt   2100
ctcatcacta tctatctatc tatctatcta tcaatcatca caggtactac ctcaaggacg   2160
cggtgcttga cggcggcatc ccgttcaaca aggcgtacgg gatgacggcg ttcgagtacc   2220
acggcacgga cccgcgcttc aaccgcgtgt tcaacgaggg catgaagaac cacagcgtga   2280
tcatcaccaa gaagctcctc gagttctaca cgggcttcga cgagtccgtc tcgacgctcg   2340
tcgacgtggg cggcggcatc ggcgccacct tacacgccat cacctcccac cactcccaca   2400 tcaggggat caacttcgac ctcccgcacg tgatctccga ggcgccgccg ttccccggcg   2460
tgcagcacgt cggcggggac atgttcaagt cggtgccggc cggcgacgcc atcctcatga   2520
agtggatcct ccacgactgg agcgacgcgc actcgcgcca gctgctcaag aactgctacg   2580
```

```
acgcgctgcc ggagaagggc ggcaaggtga tcgtcgtcga gtgcgtgctg ccggtgacca    2640
ccgacgccgt ccccaaggcg cagggcgtgt ccatgtcga catgatcatg ctcgcgcata    2700
accccggcgg cagggagcgg tacgagcggg agttccgtga cctcgccaag gccgctggct    2760
tctctgggtt caaggccacc tacatctacg ccaacgcctg ggccatcgag ttcatcaagt    2820
aa                                                                  2822
```

<210> SEQ ID NO 20
<211> LENGTH: 1089
<212> TYPE: DNA
<213> ORGANISM: Sorghum bicolor
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Ceres ID No. PI599692-85802570
<220> FEATURE:
<221> NAME/KEY: misc_feature
<223> OTHER INFORMATION: Truncated Caffeic Acid O-Methyltransferase 1
<220> FEATURE:
<221> NAME/KEY: misc_feature
<223> OTHER INFORMATION: Encodes the peptide sequence at SEQ ID NO. 21.

<400> SEQUENCE: 20

```
atggggtcga cggcggagga cgtggcggcg gtggcggacg aggaggcgtg catgtacgcg      60
atgcagctgg cgtcgtcgtc gatcctcccc atgacgctga agaacgcgct ggagctgggc     120
ctgctggagg tgcttcagaa ggacgccggc aaggcgctgg cggcggagga ggtggtggcg     180
cggctgcccg tggcgccgac gaaccccgcc gcggcggaca tggtggaccg catgctccgc     240
ctcctcgcct cctacgacgt cgtgaggtgc cagatggagg acaaggacgg caagtacgag     300
cgtcggtact ccgccgcccc cgtcgcaag tagctcaccc ctaacgagga cggcgtctcc      360
atggccgccc tcgcgctcat gaaccaggac aaggtcctca tggagagctg gtactacctc     420
aaggacgcgg tgcttgacgg cggcatcccg ttcaacaagg cgtacgggat gacggcgttc     480
gagtaccacg gcacggaccc cgcgcttcaac cgcgtgttca acgagggcat gaagaaccac     540
agcgtgatca tcaccaagaa gctcctcgag ttctacacgg gcttcgacga gtccgtctcg     600
acgctcgtcg acgtgggcgg cggcatcggc gccaccttac acgccatcac ctcccaccac     660
tcccacatca gggggatcaa cttcgacctc ccgcacgtga tctccgaggc gccgccgttc     720
cccggcgtgc agcacgtcgg cggggacatg ttcaagtcgg tgccggccgg cgacgccatc     780
ctcatgaagt ggatcctcca cgactggagc gacgcgcact cgccacgct gctcaagaac      840 tgctacgacg cgctgccgga agggcggc aaggtgatcg tcgtcgagtg cgtgctgccg       900
gtgaccaccg acgccgtccc caaggcgcag ggcgtgttcc atgtcgacat gatcatgctc     960
gcgcataacc ccggcggcag ggagcggtac gagcgggagt tccgtgacct cgccaaggcc    1020
gctggcttct ctgggttcaa ggccacctac atctacgcca acgcctgggc catcgagttc    1080
atcaagtaa                                                             1089
```

<210> SEQ ID NO 21
<211> LENGTH: 110
<212> TYPE: PRT
<213> ORGANISM: Sorghum bicolor
<220> FEATURE:
<221> NAME/KEY: misc_feature
<223> OTHER INFORMATION: Ceres ID No. PI599692-85802570
<220> FEATURE:
<221> NAME/KEY: misc_feature
<223> OTHER INFORMATION: Truncated Caffeic Acid O-Methyltransferase 1
<220> FEATURE:

-continued

<221> NAME/KEY: misc_feature
<222> LOCATION: (31)..(83)
<223> OTHER INFORMATION: Pfam Name: Dimerisation domain
<220> FEATURE:
<221> NAME/KEY: misc_feature
<222> LOCATION: (92)..(110)
<223> OTHER INFORMATION: Pfam Name: O-methyltransferase

<400> SEQUENCE: 21

Met Gly Ser Thr Ala Glu Asp Val Ala Val Ala Asp Glu Ala
1               5                   10                  15

Cys Met Tyr Ala Met Gln Leu Ala Ser Ser Ile Leu Pro Met Thr
                20                  25                  30

Leu Lys Asn Ala Leu Glu Leu Gly Leu Leu Glu Val Leu Gln Lys Asp
            35                  40                  45

Ala Gly Lys Ala Leu Ala Ala Glu Glu Val Val Ala Arg Leu Pro Val
        50                  55                  60

Ala Pro Thr Asn Pro Ala Ala Ala Asp Met Val Asp Arg Met Leu Arg
65                  70                  75                  80

Leu Leu Ala Ser Tyr Asp Val Val Arg Cys Gln Met Glu Asp Lys Asp
                85                  90                  95

Gly Lys Tyr Glu Arg Arg Tyr Ser Ala Ala Pro Val Gly Lys
            100                 105                 110

<210> SEQ ID NO 22
<211> LENGTH: 2822
<212> TYPE: DNA
<213> ORGANISM: Sorghum bicolor
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. PI602906-85802580
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<223> OTHER INFORMATION: Encodes the peptide sequence at SEQ ID NO. 24.

<400> SEQUENCE: 22
atggggtcga cggcggagga cgtggcggcg gtggcggacg aggaggcgtg catgtacgcg    60
atgcagctgg cgtcgtcgtc gatcctcccc atgacgctga agaacgcgct ggagctgggc   120
ctgctggagg tgcttcagaa ggacgccggc aaggcgctgg cggcggagga ggtggtggcg   180
cggctgcccg tggcgccgac gaaccccgcc gcggcggaca tggtggaccg catgctccgc   240
ctcctcgcct cctacgacgt cgtgaggtgc cagatggagg acaaggacgg caagtacgag   300
cgtcggtact ccgccgcccc cgtcggcaag tggctcaccc ctaacgagga cggcgtctcc   360
atggccgccc tcgcgctcat gaaccaggac aaggtcctca tggagagctg gtgagtagtc   420
gtcgtcagag cacatctcgc cccacctcac catttcatct gtagatcagt tgttgctttg   480
ctgttgatat gatgctggcg tgctagctgc atgatgatga gctcgctcat cattagtact   540
agctagtgat ttattttgtc atttaatttt ttccaagtaa aattgattga ggtgcactac   600
tagtactagc tgctagtaca aagctggcag tagttaagtt atccatgata taatatttga   660
ctaaaacaaa aaaatatttt ttttacaaa aaaagggaag taagctcaag ttcttcctaa   720
aaaaatgtag agtaggatgg aaaagtaagc aaaggacgga ccacttgtca tctccactat   780
ccagtgggcg agacttcggc gaaccttgga gaaggagagc attattggcc aactctctct   840
ctaatttttt tttcctggat tcgcaaaact ggagccgtcg atcgccggac ttattactga   900

```
cggctcacat ggatcatgga attctgcgaa attcctgatc tagacttttg cgaaactccg     960
ttcagtcatt caccaactga tggtgaatct tcagactctc aaattgtttg gtgtttggtg    1020
tgtgtgaagt gggtgtagaa aagaggcagt tggaccacag gcgactgact gacccattac    1080
catgtcactg atgctgatag attcttgccc tgttccttt agaaactttt gcacagatcg     1140
atatctgtag cagttttcct ttcatgcaat ttttgactag tttaaaatgt tcagaccgga    1200
cagtgacttc agagttcaga cacatgggcc ttgtttagtt aggccctgtt tagttcccca    1260
caaaaaaaaa tttcatccat cccatcgaat ctttgaacac atgcatggaa cattaaatgt    1320
aaataaaaaa taaactaatt acacagtttg gttgaaaatc gcgagacgaa tcttttaagc    1380
ctagttagtc catgattagc cttaagtgct acagtaacct acatgtgcta atgacagatt    1440
aattatagtt aatagatttg tcttgcagtt tcctgatgag ctatgtaatt tgtttttta     1500 ttagttttta aaaccccctc ccgacatcat tctgacatat ccgatgtgac atccaaaaat    1560
ttttcattca caatctaaac agatccttac caaaaaaatt ttgcaaaatc tttcagattc    1620
tccgtcacat caaatcttta gacgcatgca taaaatatta aacatagtca aaaataaaaa    1680
ctaattacaa agtttagtcg gaattgacga gacgaatctt ttgagtctag ttagtctatg    1740
attggataat atttgtcaaa tacaaacaaa aatggtacta ttttatttt gcaaattttt     1800 ttgaactaaa caaggccatg gcagcagtaa cagtccatta ttctacatgg gcatggcgtt    1860
gtgctgtagt gcctgcaagt agcagttgtt accatacaca catgtctgtt ctgcatcatc    1920
actctggtcc attccgaagt gctcaagcct ataacatccc tttccataat taaccatacg    1980
tgtctagtag catagttatc aaattcttgc aaaaacacac acatatctga ctatctgtac    2040
aattcatcaa aattcttaga aattgaaatc catgtcgatc gatcagtgct gtgtacgtgt    2100
ctcatcacta tctatctatc tatctatcta tcaatcatca caggtactac ctcaaggacg    2160
cggtgcttga cggcggcatc ccgttcaaca aggcgtacgg gatgacgcg ttcgagtacc     2220 acggcacgga cccgcgcttc aaccgcgtgt tcaacgaggg catgaagaac cacagcgtga    2280
tcatcaccaa gaagctcctc gagttctaca cgggcttcga cgagtccgtc tcgacgctcg    2340
tcgacgtggg cggcggcatc ggcgccacct tacacgccat cacctcccac cactcccaca    2400
tcagggggat caacttcgac ctcccgcacg tgatctccga ggcgccgccg ttccccggcg    2460
tgcagcacgt cggcggggac atgttcaagt cggtgccggc cggcgacgcc atcctcatga    2520
agtggatcct ccacgactgg agcgacgcgc actgcgccac gctgctcaag aactgctacg    2580
acgcgctgcc ggagaagggc ggcaaggtga tcgtcgtcga gtgcgtgctg ccggtgacca    2640
ccgacgccgt ccccaaggcg cagggcgtgt tccatgtcga catgatcatg ctcgcgcata    2700
accccggcgg cagggagcgg tacgagcggg agttccgtga cctcgccaag gccgctggct    2760
tctctgggtt caaggccacc tacatctacg ccaacgcctg ggccatcgag ttcatcaagt    2820
aa                                                                  2822
```

<210> SEQ ID NO 23
<211> LENGTH: 1089
<212> TYPE: DNA
<213> ORGANISM: Sorghum bicolor
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Ceres ID No. PI602906-85802580
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<223> OTHER INFORMATION: Encodes the peptide sequence at SEQ ID NO. 24.

<400> SEQUENCE: 23

| | | |
|---|---|---|
| atggggtcga cggcggagga cgtggcggcg gtggcggacg aggaggcgtg catgtacgcg | 60 |
| atgcagctgg cgtcgtcgtc gatcctcccc atgacgctga agaacgcgct ggagctgggc | 120 |
| ctgctggagg tgcttcagaa ggacgccggc aaggcgctgg cggcggagga ggtggtggcg | 180 |
| cggctgcccg tggcgccgac gaaccccgcc gcggcggaca tggtggaccg catgctccgc | 240 |
| ctcctcgcct cctacgacgt cgtgaggtgc cagatggagg acaaggacgg caagtacgag | 300 |
| cgtcggtact ccgccgcccc cgtcggcaag tggctcaccc ctaacgagga cggcgtctcc | 360 |
| atggccgccc tcgcgctcat gaaccaggac aaggtcctca tggagagctg gtactacctc | 420 |
| aaggacgcgg tgcttgacgg cggcatcccg ttcaacaagg cgtacgggat gacggcgttc | 480 |
| gagtaccacg gcacggaccc cgcgcttcaac cgcgtgttca acgagggcat gaagaaccac | 540 |
| agcgtgatca tcaccaagaa gctcctcgag ttctacacgg cttcgacga gtccgtctcg | 600 |
| acgctcgtcg acgtgggcgg cggcatcggc gccaccttac acgccatcac ctcccaccac | 660 |
| tcccacatca gggggatcaa cttcgacctc ccgcacgtga tctccgaggc gccgccgttc | 720 |
| cccggcgtgc agcacgtcgg cggggacatg ttcaagtcgg tgccggccgg cgacgccatc | 780 |
| ctcatgaagt ggatcctcca cgactggagc gacgcgcact gcgccacgct gctcaagaac | 840 |
| tgctacgacg cgctgccgga aggggcggc aaggtgatcg tcgtcgagtg cgtgctgccg | 900 |
| gtgaccaccg acgccgtccc caaggcgcag ggcgtgttcc atgtcgacat gatcatgctc | 960 |
| gcgcataacc ccgcggcag ggagcggtac gagcgggagt tccgtgacct cgccaaggcc | 1020 |
| gctggcttct ctgggttcaa ggccacctac atctacgcca acgcctgggc catcgagttc | 1080 |
| atcaagtaa | 1089 |

<210> SEQ ID NO 24
<211> LENGTH: 362
<212> TYPE: PRT
<213> ORGANISM: Sorghum bicolor
<220> FEATURE:
<221> NAME/KEY: misc_feature
<223> OTHER INFORMATION: Ceres ID No. PI602906-85802580
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<222> LOCATION: (31)..(83)
<223> OTHER INFORMATION: Pfam Name: Dimerisation domain
<220> FEATURE:
<221> NAME/KEY: misc_feature
<222> LOCATION: (92)..(339)
<223> OTHER INFORMATION: Pfam Name: O-methyltransferase

<400> SEQUENCE: 24

```
Met Gly Ser Thr Ala Glu Asp Val Ala Ala Val Ala Asp Glu Glu Ala
1               5                  10                  15

Cys Met Tyr Ala Met Gln Leu Ala Ser Ser Ser Ile Leu Pro Met Thr
            20                  25                  30

Leu Lys Asn Ala Leu Glu Leu Gly Leu Leu Glu Val Leu Gln Lys Asp
        35                  40                  45

Ala Gly Lys Ala Leu Ala Ala Glu Glu Val Val Ala Arg Leu Pro Val
    50                  55                  60

Ala Pro Thr Asn Pro Ala Ala Ala Asp Met Val Asp Arg Met Leu Arg
```

| | | | | | | 65 | | | | 70 | | | | 75 | | | | 80 | |
|---|---|---|---|---|---|---|---|---|---|---|---|---|---|---|---|---|---|---|---|

Leu Leu Ala Ser Tyr Asp Val Val Arg Cys Gln Met Glu Asp Lys Asp
                  85                        90                        95

Gly Lys Tyr Glu Arg Arg Tyr Ser Ala Ala Pro Val Gly Lys Trp Leu
                  100                        105                        110

Thr Pro Asn Glu Asp Gly Val Ser Met Ala Ala Leu Ala Leu Met Asn
                  115                        120                        125

Gln Asp Lys Val Leu Met Glu Ser Trp Tyr Tyr Leu Lys Asp Ala Val
                  130                        135                        140

Leu Asp Gly Gly Ile Pro Phe Asn Lys Ala Tyr Gly Met Thr Ala Phe
145                      150                        155                        160

Glu Tyr His Gly Thr Asp Pro Arg Phe Asn Arg Val Phe Asn Glu Gly
                  165                        170                        175

Met Lys Asn His Ser Val Ile Ile Thr Lys Lys Leu Leu Glu Phe Tyr
                  180                        185                        190

Thr Gly Phe Asp Glu Ser Val Ser Thr Leu Val Asp Val Gly Gly Gly
                  195                        200                        205

Ile Gly Ala Thr Leu His Ala Ile Thr Ser His His Ser His Ile Arg
210                      215                        220

Gly Ile Asn Phe Asp Leu Pro His Val Ile Ser Glu Ala Pro Pro Phe
225                      230                        235                        240

Pro Gly Val Gln His Val Gly Gly Asp Met Phe Lys Ser Val Pro Ala
                  245                        250                        255

Gly Asp Ala Ile Leu Met Lys Trp Ile Leu His Asp Trp Ser Asp Ala
                  260                        265                        270

His Cys Ala Thr Leu Leu Lys Asn Cys Tyr Asp Ala Leu Pro Glu Lys
                  275                        280                        285

Gly Gly Lys Val Ile Val Glu Cys Val Leu Pro Val Thr Thr Asp
                  290                        295                        300

Ala Val Pro Lys Ala Gln Gly Val Phe His Val Asp Met Ile Met Leu
305                      310                        315                        320

Ala His Asn Pro Gly Gly Arg Glu Arg Tyr Glu Arg Glu Phe Arg Asp
                  325                        330                        335

Leu Ala Lys Ala Ala Gly Phe Ser Gly Phe Lys Ala Thr Tyr Ile Tyr
                  340                        345                        350

Ala Asn Ala Trp Ala Ile Glu Phe Ile Lys
                  355                        360

```
<210> SEQ ID NO 25
<211> LENGTH: 2822
<212> TYPE: DNA
<213> ORGANISM: Sorghum bicolor
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. PI599705-85802571
<220> FEATURE:
<221> NAME/KEY: misc_feature
<223> OTHER INFORMATION: Truncated Caffeic Acid O-Methyltransferase 2
<220> FEATURE:
<221> NAME/KEY: misc_feature
<223> OTHER INFORMATION: Encodes the peptide sequence at SEQ ID NO. 27.

<400> SEQUENCE: 25
atggggtcga cggcggagga cgtggcggcg gtggcggacg aggaggcgtg catgtacgcg     60
atgcagctgg cgtcgtcgtc gatcctcccc atgacgctga agaacgcgct ggagctgggc    120
```

```
ctgctggagg tgcttcagaa ggacgccggc aaggcgctgg cggcggagga ggtggtggcg    180
cggctgcccg tggcgccgac gaaccccgcc gcggcggaca tggtggaccg catgctccgc    240
ctcctcgcct cctacgacgt cgtgaggtgc cagatggagg acaaggacgg caagtacgag    300
cgtcggtact ccgccgcccc cgtcggcaag tggctcaccc ctaacgagga cggcgtctcc    360
atggccgccc tcgcgctcat gaactaggac aaggtcctca tggagagctg gtgagtagtc    420
gtcgtcagag cacatctcgc cccacctcac catttcatct gtagatcagt tgttgctttg    480
ctgttgatat gatgctggcg tgctagctgc atgatgatga gctcgctcat cattagtact    540
agctagtgat ttatttttgtc atttaatttt ttccaagtaa aattgattga ggtgcactac    600
tagtactagc tgctagtaca aagctggcag tagttaagtt atccatgata taatatttga    660
ctaaaacaaa aaaatatttt ttttacaaa aaaggaag taagctcaag ttcttcctaa        720
aaaaatgtag agtaggatgg aaaagtaagc aaaggacgga ccacttgtca tctccactat    780
ccagtgggcg agacttcggc gaaccttgga gaaggagagc attattggcc aactctctct    840 ctaattttt tttcctggat tcgcaaaact ggagccgtcg atcgccggac ttattactga    900
cggctcacat ggatcatgga attctgcgaa attcctgatc tagacttttg cgaaactccg    960
ttcagtcatt caccaactga tggtgaatct tcagactctc aaattgtttg gtgtttggtg    1020
tgtgtgaagt gggtgtagaa aagaggcagt tggaccacag gcgactgact gacccattac    1080
catgtcactg atgctgatag attcttgccc tgttcctttt agaaactttt gcacagatcg    1140
atatctgtag cagttttcct ttcatgcaat ttttgactag tttaaaatgt tcagaccgga    1200
cagtgacttc agagttcaga cacatgggcc ttgtttagtt aggccctgtt tagttcccca    1260
caaaaaaaaa tttcatccat cccatcgaat ctttgaacac atgcatgaa cattaaatgt    1320 aaataaaaaa taaactaatt acacagtttg gttgaaaatc gcgagacgaa tcttttaagc    1380
ctagttagtc catgattagc cttaagtgct acagtaacct acatgtgcta atgacagatt    1440
aattatagtt aatagatttg tcttgcagtt tcctgatgag ctatgtaatt tgttttttta    1500
ttagttttta aaaccccctc ccgacatcat tctgacatat ccgatgtgac atccaaaaat    1560
ttttcattca caatctaaac agatccttac caaaaaaatt ttgcaaaatc tttcagattc    1620
tccgtcacat caaatcttta gacgcatgca taaaatatta aacatagtca aaaataaaaa    1680
ctaattacaa agtttagtcg gaattgacga gacgaatctt ttgagtctag ttagtctatg    1740
attggataat atttgtcaaa tacaaacaaa aatggtacta tttttatttt gcaaattttt    1800
ttgaactaaa caaggccatg gcagcagtaa cagtccatta ttctacatgg gcatggcgtt    1860
gtgctgtagt gcctgcaagt agcagttgtt accatacaca catgtctgtt ctgcatcatc    1920
actctggtcc attccgaagt gctcaagcct ataacatccc tttccataat taaccatacg    1980
tgtctagtag catagttatc aaattcttgc aaaaacacac acatatctga ctatctgtac    2040
aattcatcaa aattcttaga aattgaaatc catgtcgatc gatcagtgct gtgtacgtgt    2100
ctcatcacta tctatctatc tatctatcta tcaatcatca caggtactac ctcaaggacg    2160
cggtgcttga cggcggcatc ccgttcaaca aggcgtacgg gatgacggcg ttcgagtacc    2220
acggcacgga cccgcgcttc aaccgcgtgt caacgagggg catgaagaac cacagcgtga    2280
tcatcaccaa gaagctcctc gagttctaca cgggcttcga cgagtccgtc tcgacgctcg    2340
tcgacgtggg cggcggcatc ggcgccacct tacacgccat cacctcccac cactcccaca    2400
tcagggggat caacttcgac ctcccgcacg tgatctccga ggcgccgccg ttccccggcg    2460
tgcagcacgt cggcggggac atgttcaagt cggtgccggc cggcgacgcc atcctcatga    2520
```

| | |
|---|---|
| agtggatcct ccacgactgg agcgacgcgc actgcgccac gctgctcaag aactgctacg | 2580 |
| acgcgctgcc ggagaagggc ggcaaggtga tcgtcgtcga gtgcgtgctg ccggtgacca | 2640 |
| ccgacgccgt ccccaaggcg cagggcgtgt ccatgtcga catgatcatg ctcgcgcata | 2700 |
| accccgcgg cagggagcgg tacgagcggg agttccgtga cctcgccaag ccgctggct | 2760 |
| tctctgggtt caaggccacc tacatctacg ccaacgcctg ggccatcgag ttcatcaagt | 2820 |
| aa | 2822 |

<210> SEQ ID NO 26
<211> LENGTH: 1089
<212> TYPE: DNA
<213> ORGANISM: Sorghum bicolor
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Ceres ID No. PI599705-85802571
<220> FEATURE:
<221> NAME/KEY: misc_feature
<223> OTHER INFORMATION: Truncated Caffeic Acid O-Methyltransferase 2
<220> FEATURE:
<221> NAME/KEY: misc_feature
<223> OTHER INFORMATION: Encodes the peptide sequence at SEQ ID NO. 27.

<400> SEQUENCE: 26

| | |
|---|---|
| atggggtcga cggcggagga cgtggcggcg gtggcggacg aggaggcgtg catgtacgcg | 60 |
| atgcagctgg cgtcgtcgtc gatcctcccc atgacgctga agaacgcgct ggagctgggc | 120 |
| ctgctggagg tgcttcagaa ggacgccggc aaggcgctgg cggcggagga ggtggtggcg | 180 |
| cggctgcccg tggcgccgac gaaccccgcc gcggcggaca tggtggaccg catgctccgc | 240 |
| ctcctcgcct cctacgacgt cgtgaggtgc cagatggagg acaaggacgg caagtacgag | 300 |
| cgtcggtact ccgccgcccc cgtcggcaag tggctcaccc ctaacgagga cggcgtctcc | 360 |
| atggccgccc tcgcgctcat gaactaggac aaggtcctca tggagagctg gtactacctc | 420 |
| aaggacgcgg tgcttgacgg cggcatcccg ttcaacaagg cgtacgggat gacggcgttc | 480 |
| gagtaccacg gcacggaccc gcgcttcaac cgcgtgttca cgagggcat gaagaaccac | 540 |
| agcgtgatca tcaccaagaa gctcctcgag ttctacacgg gcttcgacga gtccgtctcg | 600 |
| acgctcgtcg acgtgggcgg cggcatcggc gccaccttac acgccatcac ctcccaccac | 660 |
| tcccacatca gggggatcaa cttcgacctc ccgcacgtga tctccgaggc ccgccgttc | 720 |
| cccgcgtgc agcacgtcgg cggggacatg ttcaagtcgg tgccggccgg cgacgccatc | 780 |
| ctcatgaagt ggatcctcca cgactggagc gacgcgcact cgccacgct gctcaagaac | 840 |
| tgctacgacg cgctgccgga aggggcggc aaggtgatcg tcgtcgagtg cgtgctgccg | 900 |
| gtgaccaccg acgccgtccc caaggcgcag ggcgtgttcc atgtcgacat gatcatgctc | 960 |
| gcgcataacc ccgcggcag ggagcggtac gagcgggagt ccgtgacct cgccaaggcc | 1020 |
| gctggcttct ctgggttcaa ggccacctac atctacgcca acgcctgggc catcgagttc | 1080 |
| atcaagtaa | 1089 |

<210> SEQ ID NO 27
<211> LENGTH: 128
<212> TYPE: PRT
<213> ORGANISM: Sorghum bicolor
<220> FEATURE:
<221> NAME/KEY: misc_feature
<223> OTHER INFORMATION: Ceres ID No. PI599705-85802571
<220> FEATURE:
<221> NAME/KEY: misc_feature

```
<223> OTHER INFORMATION: Truncated Caffeic Acid O-Methyltransferase 2
<220> FEATURE:
<221> NAME/KEY: misc_feature
<222> LOCATION: (31)..(83)
<223> OTHER INFORMATION: Pfam Name: Dimerisation domain
<220> FEATURE:
<221> NAME/KEY: misc_feature
<222> LOCATION: (92)..(128)
<223> OTHER INFORMATION: Pfam Name: O-methyltransferase

<400> SEQUENCE: 27

Met Gly Ser Thr Ala Glu Asp Val Ala Ala Val Ala Asp Glu Glu Ala
1               5                   10                  15

Cys Met Tyr Ala Met Gln Leu Ala Ser Ser Ile Leu Pro Met Thr
            20                  25                  30

Leu Lys Asn Ala Leu Glu Leu Gly Leu Leu Glu Val Leu Gln Lys Asp
        35                  40                  45

Ala Gly Lys Ala Leu Ala Ala Glu Glu Val Val Ala Arg Leu Pro Val
    50                  55                  60

Ala Pro Thr Asn Pro Ala Ala Asp Met Val Asp Arg Met Leu Arg
65                  70                  75                  80

Leu Leu Ala Ser Tyr Asp Val Val Arg Cys Gln Met Glu Asp Lys Asp
                85                  90                  95

Gly Lys Tyr Glu Arg Arg Tyr Ser Ala Ala Pro Val Gly Lys Trp Leu
            100                 105                 110

Thr Pro Asn Glu Asp Gly Val Ser Met Ala Ala Leu Ala Leu Met Asn
        115                 120                 125

<210> SEQ ID NO 28
<211> LENGTH: 2822
<212> TYPE: DNA
<213> ORGANISM: Sorghum bicolor
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. PI602914-85802582
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<223> OTHER INFORMATION: Encodes the peptide sequence at SEQ ID NO. 30.

<400> SEQUENCE: 28
atggggtcga cggcgagga cgtggcggcg gtggcggacg aggaggcgtg catgtacgcg     60
atgcagctgg cgtcgtcgtc gatcctcccc atgacgctga agaacgcgct ggagctgggc    120
ctgctggagg tgcttcagaa ggacgccggc aaggcgctgg cggcggagga ggtggtggcg    180
cggctgcccg tggcgccgac gaaccccgcc gcggcggaca tggtggaccg catgctccgc    240
ctcctcgcct cctacgacgt cgtgaagtgc cagatggagg acaaggacgg caagtacgag    300
cgtcggtact ccgccgcccc cgtcggcaag tggctcaccc ctaacgagga cggcgtctcc    360
atggccgccc tcgcgctcat gaaccaggac aaggtcctca tggagagctg gtgagtagtc    420
gtcgtcagag cacatctcgc cccacctcac catttcatct gtagatcagt tgttgctttg    480
ctgttgatat gatgctggcg tgctagctgc atgatgatga gctcgctcat cattagtact    540
agctagtgat ttattttgtc atttaatttt ttccaagtaa aattgattga ggtgcactac    600
tagtactagc tgctagtaca aagctggcag tagttaagtt atccatgata taatatttga    660
ctaaaacaaa aaaatatttt tttttacaaa aaaagggaag taagctcaag ttcttcctaa    720
```

| | |
|---|---|
| aaaaatgtag agtaggatgg aaaagtaagc aaaggacgga ccacttgtca tctccactat | 780 |
| ccagtgggcg agacttcggc gaaccttgga gaaggagagc attattggcc aactctctct | 840 |
| ctaattttt tttcctggat tcgcaaaact ggagccgtcg atcgccggac ttattactga | 900 |
| cggctcacat ggatcatgga attctgcgaa attcctgatc tagacttttg cgaaactccg | 960 |
| ttcagtcatt caccaactga tggtgaatct tcagactctc aaattgtttg gtgtttggtg | 1020 |
| tgtgtgaagt gggtgtagaa aagaggcagt tggaccacag cgactgact gacccattac | 1080 |
| catgtcactg atgctgatag attcttgccc tgttcctttt agaaactttt gcacagatcg | 1140 |
| atatctgtag cagttttcct ttcatgcaat ttttgactag tttaaaatgt tcagaccgga | 1200 |
| cagtgacttc agagttcaga cacatgggcc ttgtttagtt aggccctgtt tagttcccca | 1260 |
| caaaaaaaaa tttcatccat cccatcgaat ctttgaacac atgcatggaa cattaaatgt | 1320 |
| aaataaaaaa taaactaatt acacagtttg gttgaaaatc gcgagacgaa tcttttaagc | 1380 |
| ctagttagtc catgattagc cttaagtgct acagtaacct acatgtgcta atgacagatt | 1440 |
| aattatagtt aatagatttg tcttgcagtt tcctgatgag ctatgtaatt tgttttttta | 1500 |
| ttagttttta aaaccccctc ccgacatcat tctgacatat ccgatgtgac atccaaaaat | 1560 |
| ttttcattca caatctaaac agatccttac caaaaaaatt ttgcaaaatc tttcagattc | 1620 |
| tccgtcacat caaatctta gacgcatgca taaaatatta aacatagtca aaaataaaaa | 1680 |
| ctaattacaa agtttagtcg gaattgacga gacgaatctt ttgagtctag ttagtctatg | 1740 |
| attggataat atttgtcaaa tacaaacaaa aatggtacta ttttatttt gcaaatttt | 1800 |
| ttgaactaaa caaggccatg gcagcagtaa cagtccatta ttctacatgg gcatggcgtt | 1860 |
| gtgctgtagt gcctgcaagt agcagttgtt accatacaca catgtctgtt ctgcatcatc | 1920 |
| actctggtcc attccgaagt gctcaagcct ataacatccc tttccataat taaccatacg | 1980 |
| tgtctagtag catagttatc aaattcttgc aaaaacacac acatatctga ctatctgtac | 2040 |
| aattcatcaa aattcttaga aattgaaatc catgtcgatc gatcagtgct gtgtacgtgt | 2100 |
| ctcatcacta tctatctatc tatctatcta tcaatcatca caggtactac ctcaaggacg | 2160 |
| cggtgcttga cggcggcatc ccgttcaaca aggcgtacgg gatgacggcg ttcgagtacc | 2220 |
| acggcacgga cccgcgcttc aaccgcgtgt tcaacgaggg catgaagaac cacagcgtga | 2280 |
| tcatcaccaa gaagctcctc gagttctaca cgggcttcga cgagtccgtc tcgacgctcg | 2340 |
| tcgacgtggg cggcggcatc ggcgccacct tacacgccat cacctcccac cactcccaca | 2400 |
| tcaggggat caacttcgac ctcccgcacg tgatctccga ggcgccgccg ttccccggcg | 2460 |
| tgcagcacgt cggcggggac atgttcaagt cggtgccggc cggcgacgcc atcctcatga | 2520 |
| agtggatcct ccacgactgg agcgacgcgc actgcgccac gctgctcaag aactgctacg | 2580 |
| acgcgctgcc ggagaagggc ggcaaggtga tcgtcgtcga gtgcgtgctg ccggtgacca | 2640 |
| ccgacgccgt ccccaaggcg cagggcgtgt tccatgtcga catgatcatg ctcgcgcata | 2700 |
| accccggcgg cagggagcgg tacgagcggg agttccgtga cctcgccaag gccgctggct | 2760 |
| tctctgggtt caaggccacc tacatctacg ccaacgcctg ggccatcgag ttcatcaagt | 2820 |
| aa | 2822 |

<210> SEQ ID NO 29
<211> LENGTH: 1089
<212> TYPE: DNA
<213> ORGANISM: Sorghum bicolor
<220> FEATURE:
<221> NAME/KEY: misc_feature
<223> OTHER INFORMATION: cDNA sequence -continued

```
<220> FEATURE:
<221> NAME/KEY: misc_feature
<223> OTHER INFORMATION: Ceres ID No. PI602914-85802582
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<223> OTHER INFORMATION: Encodes the peptide sequence at SEQ ID NO. 30.

<400> SEQUENCE: 29
atggggtcga cggcggagga cgtggcggcg gtggcggacg aggaggcgtg catgtacgcg    60
atgcagctgg cgtcgtcgtc gatcctcccc atgacgctga gaacgcgct ggagctgggc    120
ctgctggagg tgcttcagaa ggacgccggc aaggcgctgg cggcggagga ggtggtggcg    180
cggctgcccg tggcgccgac gaaccccgcc gcggcggaca tggtggaccg catgctccgc    240
ctcctcgcct cctacgacgt cgtgaagtgc cagatggagg acaaggacgg caagtacgag    300
cgtcggtact ccgccgcccc cgtcggcaag tggctcaccc ctaacgagga cggcgtctcc    360
atggccgccc tcgcgctcat gaaccaggac aaggtcctca tggagagctg gtactacctc    420
aaggacgcgg tgcttgacgg cggcatcccg ttcaacaagg cgtacgggat gacggcgttc    480
gagtaccacg gcacggaccc gcgcttcaac cgcgtgttca acgagggcat gaagaaccac    540
agcgtgatca tcaccaagaa gctcctcgag ttctacacgg gcttcgacga gtccgtctcg    600
acgctcgtcg acgtgggcgg cggcatcggc gccaccttac acgccatcac ctcccaccac    660
tcccacatca gggggatcaa cttcgacctc ccgcacgtga ctccgaggc gccgccgttc    720
cccggcgtgc agcacgtcgg cggggacatg ttcaagtcgg tgccggccgg cgacgccatc    780
ctcatgaagt ggatcctcca cgactggagc gacgcgcact gcgccacgct gctcaagaac    840
tgctacgacg cgctgccgga agggcggc aaggtgatcg tcgtcgagtg cgtgctgccg    900
gtgaccaccg acgccgtccc caaggcgcag ggcgtgttcc atgtcgacat gatcatgctc    960
gcgcataacc ccggcggcag ggagcggtac gagcgggagt ccgtgacct cgccaaggcc    1020
gctggcttct ctgggttcaa ggccacctac atctacgcca acgcctgggc catcgagttc    1080
atcaagtaa                                                             1089
```

```
<210> SEQ ID NO 30
<211> LENGTH: 362
<212> TYPE: PRT
<213> ORGANISM: Sorghum bicolor
<220> FEATURE:
<221> NAME/KEY: misc_feature
<223> OTHER INFORMATION: Ceres ID No. PI602914-85802582
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<222> LOCATION: (31)..(83)
<223> OTHER INFORMATION: Pfam Name: Dimerisation domain
<220> FEATURE:
<221> NAME/KEY: misc_feature
<222> LOCATION: (92)..(339)
<223> OTHER INFORMATION: Pfam Name: O-methyltransferase

<400> SEQUENCE: 30

Met Gly Ser Thr Ala Glu Asp Val Ala Ala Val Ala Asp Glu Glu Ala
1               5                   10                  15

Cys Met Tyr Ala Met Gln Leu Ala Ser Ser Ser Ile Leu Pro Met Thr
            20                  25                  30

Leu Lys Asn Ala Leu Glu Leu Gly Leu Leu Glu Val Leu Gln Lys Asp
        35                  40                  45
```

```
Ala Gly Lys Ala Leu Ala Ala Glu Glu Val Val Ala Arg Leu Pro Val
 50                  55                  60

Ala Pro Thr Asn Pro Ala Ala Asp Met Val Asp Arg Met Leu Arg
 65                  70                  75                  80

Leu Leu Ala Ser Tyr Asp Val Val Lys Cys Gln Met Glu Asp Lys Asp
                 85                  90                  95

Gly Lys Tyr Glu Arg Arg Tyr Ser Ala Ala Pro Val Gly Lys Trp Leu
            100                 105                 110

Thr Pro Asn Glu Asp Gly Val Ser Met Ala Ala Leu Ala Leu Met Asn
        115                 120                 125

Gln Asp Lys Val Leu Met Glu Ser Trp Tyr Tyr Leu Lys Asp Ala Val
130                 135                 140

Leu Asp Gly Gly Ile Pro Phe Asn Lys Ala Tyr Gly Met Thr Ala Phe
145                 150                 155                 160

Glu Tyr His Gly Thr Asp Pro Arg Phe Asn Arg Val Phe Asn Glu Gly
                165                 170                 175

Met Lys Asn His Ser Val Ile Ile Thr Lys Lys Leu Leu Glu Phe Tyr
            180                 185                 190

Thr Gly Phe Asp Glu Ser Val Ser Thr Leu Val Asp Val Gly Gly Gly
        195                 200                 205

Ile Gly Ala Thr Leu His Ala Ile Thr Ser His His Ser His Ile Arg
210                 215                 220

Gly Ile Asn Phe Asp Leu Pro His Val Ile Ser Glu Ala Pro Pro Phe
225                 230                 235                 240

Pro Gly Val Gln His Val Gly Gly Asp Met Phe Lys Ser Val Pro Ala
                245                 250                 255

Gly Asp Ala Ile Leu Met Lys Trp Ile Leu His Asp Trp Ser Asp Ala
            260                 265                 270

His Cys Ala Thr Leu Leu Lys Asn Cys Tyr Asp Ala Leu Pro Glu Lys
        275                 280                 285

Gly Gly Lys Val Ile Val Val Glu Cys Val Leu Pro Val Thr Thr Asp
290                 295                 300

Ala Val Pro Lys Ala Gln Gly Val Phe His Val Asp Met Ile Met Leu
305                 310                 315                 320

Ala His Asn Pro Gly Gly Arg Glu Arg Tyr Glu Arg Glu Phe Arg Asp
                325                 330                 335

Leu Ala Lys Ala Ala Gly Phe Ser Gly Phe Lys Ala Thr Tyr Ile Tyr
            340                 345                 350

Ala Asn Ala Trp Ala Ile Glu Phe Ile Lys
        355                 360

<210> SEQ ID NO 31
<211> LENGTH: 2824
<212> TYPE: DNA
<213> ORGANISM: Artificial Sequence
<220> FEATURE:
<221> NAME/KEY: misc_feature
<223> OTHER INFORMATION: Sorghum x Sudangrass
<220> FEATURE:
<221> NAME/KEY: misc_feature
<223> OTHER INFORMATION: Genomic sequence
<220> FEATURE:
<221> NAME/KEY: misc_feature
<223> OTHER INFORMATION: Ceres ID No. SS1-85802563
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
```

<223> OTHER INFORMATION: Encodes the peptide sequence at SEQ ID NO. 33.

<400> SEQUENCE: 31

| | | | | | |
|---|---|---|---|---|---|
| atggggtcga | cggcggagga | cgtggcggcg | gtggcggacg | aggaggcgtg | catgtacgcg | 60 |
| atgcagctgg | cgtcgtcgtc | aatcctcccc | atgacgctga | agaacgcgct | ggagctgggc | 120 |
| ctgctggagg | tgcttcagaa | ggacgccggc | aaggcgctgg | cggcggagga | ggtggtggcg | 180 |
| cggctgcccg | tggcgccgac | gaaccccgcc | gcggcggaca | tggtggaccg | catgctccgc | 240 |
| ctcctcgcct | cctacgacgt | cgtgaggtgc | cagatggagg | acaaggacgg | caagtacgag | 300 |
| cgccggtact | ccgccgcccc | cgtcggcaag | tggctcaccc | ctaacgagga | cggcgtctcc | 360 |
| atggccgccc | tcgcgctcat | gaaccaggac | aaggtcctca | tggagagctg | gtgagtagtc | 420 |
| gtcgtcagag | cacatctcgc | cccacctcac | catttcatct | gtagatcagt | tgttgctttg | 480 |
| ctgttgatga | tggcgtgcta | gctgcatgat | gatgagctcg | ctcatcatta | gtactagcta | 540 |
| gtaatttatt | ttgtcattta | atttttcca | agtaaaattg | attgaggtgc | actactagta | 600 |
| ctagctgcta | gtacaaagct | ggcagtagtt | aagttatcca | tgatataata | tttgactaaa | 660 |
| acaaaaaaaa | tattttttta | caaaaaaagg | gaagtaagct | caagttcttc | ctaaaaaaat | 720 |
| gtagagtagg | atggaaaagt | aagcaaagga | cggaccactt | gtcatctcca | ctatccagtg | 780 |
| ggcgagactt | cggcgaacct | tggagaagga | gagcattatt | ggccaactct | ctctctaatt | 840 |
| ttttttttcct | ggattcgcaa | aactggagcc | gtcgatcgcc | ggacttatta | ctgacggctc | 900 |
| acatggatca | tggaattctg | cgaaattcct | gatctagact | tttgcgaaac | tccgttcagt | 960 |
| cattcaccaa | ctgatggtga | atcttcagac | tctcaaattg | tttggtgttt | ggtgtgtgtg | 1020 |
| aagtgggtgt | agaaaagagg | cagttggacc | acaggcgact | gactgaccca | ttaccatgtc | 1080 |
| actgatgctg | atagattctt | gccctgttcc | ttttagaaac | ttttgcacag | atcgatatct | 1140 |
| gtagcagttt | tcctttcatg | caattttttga | ctagtttaaa | atgttcagac | cggacagtga | 1200 |
| cttcagagtt | cagacacatg | ggccttgttt | agttaggccc | tgtttagttc | cccacaaaaa | 1260 |
| aaaatttcat | ccatcccatc | gaatctttga | acacatgcat | ggaacattaa | atgtaaataa | 1320 |
| aaaataaact | aattacacag | tttggttgaa | atcgcgaga | cgaatctttt | aagcctagtt | 1380 |
| agtccatgat | tagccttaag | tgctacagta | acctacatgt | gctaatgaca | gattaattat | 1440 |
| agttaataga | tttgtcttgc | agtttcctga | tgagctatgt | aatttgtttt | tttattagtt | 1500 |
| tttaaaaacc | cctcccgaca | tcattctgac | atatccgatg | tgacatccaa | aaatttttca | 1560 |
| ttcacaatct | aaacagatcc | ttaccaaaaa | aattttgcaa | aatctttcag | attctccgtc | 1620 |
| acatcaaatc | tttagacgca | tgcataaaat | attaaacata | gtcaaaaata | aaaactaatt | 1680 |
| acaaagttta | gtcggaattg | acgagacgaa | tcttttgagt | ctagttagtc | tatgattgga | 1740 |
| taatatttgt | caaatacaaa | caaaaatggt | actatttta | ttttgcaaat | tttttgaac | 1800 |
| taaacaaggc | catggcagca | gtaacagtcc | attattctac | atgggcatgg | cgttgtgctg | 1860 |
| tagtgcctgc | aagtagcagt | tgttaccata | cacacatgtc | tgttctgcat | catcactctg | 1920 |
| gtccattccg | aagtgctcaa | gcctataaca | tccctttcca | taattaacca | tacgtgtcta | 1980 |
| gtagcatagt | tatcaaattc | ttgcaaaaac | acacacatat | ctgactatct | gtacaattca | 2040 |
| tcaaaattct | tagaaattga | aatccatgtc | gatcgatcag | tgctgtgtac | gtgtctcatc | 2100 |
| actatctatc | tatctatcta | tctatctatc | tatcaatcat | cacaggtact | acctgaagga | 2160 |
| cgcggtgctt | gacggcggca | tcccgttcaa | caaggcgtac | gggatgacgg | cgttcgagta | 2220 |
| ccacggcacg | gacccgcgct | tcaaccgcgt | gttcaacgag | ggcatgaaga | accacagcgt | 2280 |

-continued

| | |
|---|---|
| gatcatcacc aagaagctcc tcgagttcta cacgggcttc gacgagtccg tctcgacgct | 2340 |
| cgtcgacgtg ggcggcggca tcggcgccac cttacacgcc atcacctccc accactccca | 2400 |
| catcaggggc gtcaacttcg acctccccca cgtgatctcc gaggcgccgc cgttccccgg | 2460 |
| cgtgcagcac gtcggcgggg acatgttcaa gtcggtgccg gccggcgacg ccatcctcat | 2520 |
| gaagtggatc ctccacgact ggagcgacgc gcactgcgcc acgctgctca agaactgcta | 2580 |
| cgacgcgctg ccggagaagg gcggcaaggt gatcgtcgtc gagtgcgtgc tgccggtgac | 2640 |
| caccgacgcc gtccccaagg cgcagggcgt gttccatgtc gacatgatca tgctcgcgca | 2700 |
| taacccccggc ggcagggagc ggtacgagcg ggagttccgt gacctcgcca aggccgctgg | 2760 |
| cttctctggg ttcaaggcca cctacatcta cgccaacgcc tgggccatcg agttcatcaa | 2820 |
| gtaa | 2824 |

<210> SEQ ID NO 32
<211> LENGTH: 1089
<212> TYPE: DNA
<213> ORGANISM: Artificial Sequence
<220> FEATURE:
<221> NAME/KEY: misc_feature
<223> OTHER INFORMATION: Sorghum x Sudangrass
<220> FEATURE:
<221> NAME/KEY: misc_feature
<223> OTHER INFORMATION: cDNA sequence
<220> FEATURE:
<221> NAME/KEY: misc_feature
<223> OTHER INFORMATION: Ceres ID No. SS1-85802563
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<223> OTHER INFORMATION: Encodes the peptide sequence at SEQ ID NO. 33.

<400> SEQUENCE: 32

| | |
|---|---|
| atggggtcga cggcggagga cgtggcggcg gtggcggacg aggaggcgtg catgtacgcg | 60 |
| atgcagctgg cgtcgtcgtc aatcctcccc atgacgctga agaacgcgct ggagctgggc | 120 |
| ctgctggagg tgcttcagaa ggacgccggc aaggcgctgg cggcgaggag ggtggtggcg | 180 |
| cggctgcccg tggcgccgac gaaccccgcc gcggcggaca tggtggaccg catgctccgc | 240 |
| ctcctcgcct cctacgacgt cgtgaggtgc cagatggagg acaaggacgg caagtacgag | 300 |
| cgccggtact ccgccgcccc cgtcggcaag tggctcaccc ctaacgagga cggcgtctcc | 360 |
| atggccgccc tcgcgctcat gaaccaggac aaggtcctca tggagagctg gtactacctg | 420 |
| aaggacgcgg tgcttgacgg cggcatcccg ttcaacaagg cgtacgggat gacggcgttc | 480 |
| gagtaccacg gcacggaccc gcgcttcaac cgcgtgttca cgagggcat gaagaaccac | 540 |
| agcgtgatca tcaccaagaa gctcctcgag ttctacacgg gcttcgacga gtccgtctcg | 600 |
| acgctcgtcg acgtgggcgg cggcatcggc gccaccttac acgccatcac ctcccaccac | 660 |
| tcccacatca ggggcgtcaa cttcgacctc ccccacgtga tctccgaggc gccgccgttc | 720 |
| cccggcgtgc agcacgtcgg cggggacatg ttcaagtcgg tgccggccgg cgacgccatc | 780 |
| ctcatgaagt ggatcctcca cgactggagc gacgcgcact gcgccacgct gctcaagaac | 840 |
| tgctacgacg cgctgccgga gaagggcggc aaggtgatcg tcgtcgagtg cgtgctgccg | 900 |
| gtgaccaccg acgccgtccc caaggcgcag ggcgtgttcc atgtcgacat gatcatgctc | 960 |
| gcgcataacc ccggcggcag ggagcggtac gagcgggagt tccgtgacct cgccaaggcc | 1020 |
| gctggcttct ctgggttcaa ggccacctac atctacgcca acgcctgggc catcgagttc | 1080 |
| atcaagtaa | 1089 |

```
<210> SEQ ID NO 33
<211> LENGTH: 362
<212> TYPE: PRT
<213> ORGANISM: Artificial Sequence
<220> FEATURE:
<221> NAME/KEY: misc_feature
<223> OTHER INFORMATION: Sorghum x Sudangrass
<220> FEATURE:
<221> NAME/KEY: misc_feature
<223> OTHER INFORMATION: Ceres ID No. SS1-85802563
<220> FEATURE:
<221> NAME/KEY: misc_feature
<223> OTHER INFORMATION: Full length Caffeic Acid O-Methyltransferase
<220> FEATURE:
<221> NAME/KEY: misc_feature
<222> LOCATION: (31)..(83)
<223> OTHER INFORMATION: Pfam Name: Dimerisation domain
<220> FEATURE:
<221> NAME/KEY: misc_feature
<222> LOCATION: (92)..(339)
<223> OTHER INFORMATION: Pfam Name: O-methyltransferase

<400> SEQUENCE: 33

Met Gly Ser Thr Ala Glu Asp Val Ala Ala Val Ala Asp Glu Glu Ala
1               5                   10                  15

Cys Met Tyr Ala Met Gln Leu Ala Ser Ser Ile Leu Pro Met Thr
            20                  25                  30

Leu Lys Asn Ala Leu Glu Leu Gly Leu Leu Glu Val Leu Gln Lys Asp
        35                  40                  45

Ala Gly Lys Ala Leu Ala Ala Glu Glu Val Val Ala Arg Leu Pro Val
    50                  55                  60

Ala Pro Thr Asn Pro Ala Ala Asp Met Val Asp Arg Met Leu Arg
65                  70                  75                  80

Leu Leu Ala Ser Tyr Asp Val Val Arg Cys Gln Met Glu Asp Lys Asp
                85                  90                  95

Gly Lys Tyr Glu Arg Arg Tyr Ser Ala Ala Pro Val Gly Lys Trp Leu
            100                 105                 110

Thr Pro Asn Glu Asp Gly Val Ser Met Ala Ala Leu Ala Leu Met Asn
        115                 120                 125

Gln Asp Lys Val Leu Met Glu Ser Trp Tyr Tyr Leu Lys Asp Ala Val
    130                 135                 140

Leu Asp Gly Gly Ile Pro Phe Asn Lys Ala Tyr Gly Met Thr Ala Phe
145                 150                 155                 160

Glu Tyr His Gly Thr Asp Pro Arg Phe Asn Arg Val Phe Asn Glu Gly
                165                 170                 175

Met Lys Asn His Ser Val Ile Ile Thr Lys Lys Leu Leu Glu Phe Tyr
            180                 185                 190

Thr Gly Phe Asp Glu Ser Val Ser Thr Leu Val Asp Val Gly Gly Gly
        195                 200                 205

Ile Gly Ala Thr Leu His Ala Ile Thr Ser His His Ser His Ile Arg
    210                 215                 220

Gly Val Asn Phe Asp Leu Pro His Val Ile Ser Glu Ala Pro Pro Phe
225                 230                 235                 240

Pro Gly Val Gln His Val Gly Gly Asp Met Phe Lys Ser Val Pro Ala
                245                 250                 255

Gly Asp Ala Ile Leu Met Lys Trp Ile Leu His Asp Trp Ser Asp Ala
            260                 265                 270

His Cys Ala Thr Leu Leu Lys Asn Cys Tyr Asp Ala Leu Pro Glu Lys
        275                 280                 285

Gly Gly Lys Val Ile Val Val Glu Cys Val Leu Pro Val Thr Thr Asp
    290                 295                 300
```

-continued

```
Ala Val Pro Lys Ala Gln Gly Val Phe His Val Asp Met Ile Met Leu
305                 310                 315                 320

Ala His Asn Pro Gly Gly Arg Glu Arg Tyr Glu Arg Glu Phe Arg Asp
            325                 330                 335

Leu Ala Lys Ala Ala Gly Phe Ser Gly Phe Lys Ala Thr Tyr Ile Tyr
        340                 345                 350

Ala Asn Ala Trp Ala Ile Glu Phe Ile Lys
        355                 360

<210> SEQ ID NO 34
<211> LENGTH: 13
<212> TYPE: DNA
<213> ORGANISM: Sorghum bicolor
<220> FEATURE:
<221> NAME/KEY: misc_feature
<223> OTHER INFORMATION: SNP sequence CAD1 truncation

<400> SEQUENCE: 34
cccacgtagg gcg                                                          13

<210> SEQ ID NO 35
<211> LENGTH: 13
<212> TYPE: DNA
<213> ORGANISM: Sorghum bicolor
<220> FEATURE:
<221> NAME/KEY: misc_feature
<223> OTHER INFORMATION: SNP sequence CAD1 wild type

<400> SEQUENCE: 35
cccacgcagg gcg                                                          13

<210> SEQ ID NO 36
<211> LENGTH: 15
<212> TYPE: DNA
<213> ORGANISM: Sorghum bicolor
<220> FEATURE:
<221> NAME/KEY: misc_feature
<223> OTHER INFORMATION: SNP sequence CAD2 truncation

<400> SEQUENCE: 36
acctcctaga tcgag                                                        15

<210> SEQ ID NO 37
<211> LENGTH: 15
<212> TYPE: DNA
<213> ORGANISM: Sorghum bicolor
<220> FEATURE:
<221> NAME/KEY: misc_feature
<223> OTHER INFORMATION: SNP sequence CAD2 wild type

<400> SEQUENCE: 37
acctcccaga tcgag                                                        15

<210> SEQ ID NO 38
<211> LENGTH: 22
<212> TYPE: DNA
<213> ORGANISM: Sorghum bicolor
<220> FEATURE:
<221> NAME/KEY: misc_feature
<223> OTHER INFORMATION: CAD1-F oligonucleotide primer

<400> SEQUENCE: 38
agtcccagtc caagaggaga at                                                22
```

```
<210> SEQ ID NO 39
<211> LENGTH: 26
<212> TYPE: DNA
<213> ORGANISM: Sorghum bicolor
<220> FEATURE:
<221> NAME/KEY: misc_feature
<223> OTHER INFORMATION: CAD1-R oligonucleotide primer

<400> SEQUENCE: 39
acgtatcagt tatagtatat ggatca                                          26

<210> SEQ ID NO 40
<211> LENGTH: 24
<212> TYPE: DNA
<213> ORGANISM: Sorghum bicolor
<220> FEATURE:
<221> NAME/KEY: misc_feature
<223> OTHER INFORMATION: CAD2-F oligonucleotide primer

<400> SEQUENCE: 40
tatacgtatg catattctga tcca                                            24

<210> SEQ ID NO 41
<211> LENGTH: 22
<212> TYPE: DNA
<213> ORGANISM: Sorghum bicolor
<220> FEATURE:
<221> NAME/KEY: misc_feature
<223> OTHER INFORMATION: CAD2-R oligonucleotide primer

<400> SEQUENCE: 41
taggtttgct ggtattgtac ct                                              22

<210> SEQ ID NO 42
<211> LENGTH: 22
<212> TYPE: DNA
<213> ORGANISM: Sorghum bicolor
<220> FEATURE:
<221> NAME/KEY: misc_feature
<223> OTHER INFORMATION: CAD3-F oligonucleotide primer

<400> SEQUENCE: 42
caacgtgttg tgtggagtag ct                                              22

<210> SEQ ID NO 43
<211> LENGTH: 25
<212> TYPE: DNA
<213> ORGANISM: Sorghum bicolor
<220> FEATURE:
<221> NAME/KEY: misc_feature
<223> OTHER INFORMATION: CAD3-R oligonucleotide primer

<400> SEQUENCE: 43
ctttaatggg ataataattg tcaaa                                           25

<210> SEQ ID NO 44
<211> LENGTH: 22
<212> TYPE: DNA
<213> ORGANISM: Sorghum bicolor
<220> FEATURE:
<221> NAME/KEY: misc_feature
<223> OTHER INFORMATION: CAD4-F oligonucleotide primer

<400> SEQUENCE: 44
tttgggtttg gctattatag ca                                              22
```

-continued

```
<210> SEQ ID NO 45
<211> LENGTH: 22
<212> TYPE: DNA
<213> ORGANISM: Sorghum bicolor
<220> FEATURE:
<221> NAME/KEY: misc_feature
<223> OTHER INFORMATION: CAD4-R oligonucleotide primer

<400> SEQUENCE: 45
aaagtatatg caggcgatgg at                                              22

<210> SEQ ID NO 46
<211> LENGTH: 22
<212> TYPE: DNA
<213> ORGANISM: Sorghum bicolor
<220> FEATURE:
<221> NAME/KEY: misc_feature
<223> OTHER INFORMATION: CAD5-F oligonucleotide primer

<400> SEQUENCE: 46
gttatgtggt gcagtaattt ga                                              22

<210> SEQ ID NO 47
<211> LENGTH: 23
<212> TYPE: DNA
<213> ORGANISM: Sorghum bicolor
<220> FEATURE:
<221> NAME/KEY: misc_feature
<223> OTHER INFORMATION: CAD5-R oligonucleotide primer

<400> SEQUENCE: 47
atacagagta ttactcgatc cca                                             23

<210> SEQ ID NO 48
<211> LENGTH: 22
<212> TYPE: DNA
<213> ORGANISM: Sorghum bicolor
<220> FEATURE:
<221> NAME/KEY: misc_feature
<223> OTHER INFORMATION: CAD6-F oligonucleotide primer

<400> SEQUENCE: 48
gggcttcaaa gtaccctatg gt                                              22

<210> SEQ ID NO 49
<211> LENGTH: 23
<212> TYPE: DNA
<213> ORGANISM: Sorghum bicolor
<220> FEATURE:
<221> NAME/KEY: misc_feature
<223> OTHER INFORMATION: CAD6-R oligonucleotide primer

<400> SEQUENCE: 49
tactactcat ttctgcagct ctt                                             23

<210> SEQ ID NO 50
<211> LENGTH: 22
<212> TYPE: DNA
<213> ORGANISM: Sorghum bicolor
<220> FEATURE:
<221> NAME/KEY: misc_feature
<223> OTHER INFORMATION: CAD7-F oligonucleotide primer

<400> SEQUENCE: 50
agagtttgtt gcgtctaaga tg                                              22
```

<210> SEQ ID NO 51
<211> LENGTH: 22
<212> TYPE: DNA
<213> ORGANISM: Sorghum bicolor
<220> FEATURE:
<221> NAME/KEY: misc_feature
<223> OTHER INFORMATION: CAD7-R oligonucleotide primer

<400> SEQUENCE: 51
gaaactcact tctggtcgac ga                                      22

<210> SEQ ID NO 52
<211> LENGTH: 22
<212> TYPE: DNA
<213> ORGANISM: Sorghum bicolor
<220> FEATURE:
<221> NAME/KEY: misc_feature
<223> OTHER INFORMATION: CAD8-F oligonucleotide primer

<400> SEQUENCE: 52
acaagaagat ctggtcctac aa                                      22

<210> SEQ ID NO 53
<211> LENGTH: 22
<212> TYPE: DNA
<213> ORGANISM: Sorghum bicolor
<220> FEATURE:
<221> NAME/KEY: misc_feature
<223> OTHER INFORMATION: CAD8-R oligonucleotide primer

<400> SEQUENCE: 53
tagtaggtga ggattcggct tc                                      22

<210> SEQ ID NO 54
<211> LENGTH: 18
<212> TYPE: DNA
<213> ORGANISM: Sorghum bicolor
<220> FEATURE:
<221> NAME/KEY: misc_feature
<223> OTHER INFORMATION: CAD9-F oligonucleotide primer

<400> SEQUENCE: 54
aaccacagaa gccgaatc                                           18

<210> SEQ ID NO 55
<211> LENGTH: 18
<212> TYPE: DNA
<213> ORGANISM: Sorghum bicolor
<220> FEATURE:
<221> NAME/KEY: misc_feature
<223> OTHER INFORMATION: CAD9-R oligonucleotide primer

<400> SEQUENCE: 55
tcagcccaaa ggcccttta                                          18

<210> SEQ ID NO 56
<211> LENGTH: 19
<212> TYPE: DNA
<213> ORGANISM: Sorghum bicolor
<220> FEATURE:
<221> NAME/KEY: misc_feature
<223> OTHER INFORMATION: CAD10-F oligonucleotide primer

<400> SEQUENCE: 56
caggtttgtg gtgaagatc                                          19

```
<210> SEQ ID NO 57
<211> LENGTH: 20
<212> TYPE: DNA
<213> ORGANISM: Sorghum bicolor
<220> FEATURE:
<221> NAME/KEY: misc_feature
<223> OTHER INFORMATION: CAD10-R oligonucleotide primer

<400> SEQUENCE: 57
gatgatgtag tccagcgagt                                              20

<210> SEQ ID NO 58
<211> LENGTH: 20
<212> TYPE: DNA
<213> ORGANISM: Sorghum bicolor
<220> FEATURE:
<221> NAME/KEY: misc_feature
<223> OTHER INFORMATION: CAD11-F oligonucleotide primer

<400> SEQUENCE: 58
atcagctcgt cgtccaagaa                                              20

<210> SEQ ID NO 59
<211> LENGTH: 18
<212> TYPE: DNA
<213> ORGANISM: Sorghum bicolor
<220> FEATURE:
<221> NAME/KEY: misc_feature
<223> OTHER INFORMATION: CAD11-R oligonucleotide primer

<400> SEQUENCE: 59
catcttgacc acctcgat                                                18

<210> SEQ ID NO 60
<211> LENGTH: 20
<212> TYPE: DNA
<213> ORGANISM: Sorghum bicolor
<220> FEATURE:
<221> NAME/KEY: misc_feature
<223> OTHER INFORMATION: CAD12-F oligonucleotide primer

<400> SEQUENCE: 60
gactcgctgg actacatcat                                              20

<210> SEQ ID NO 61
<211> LENGTH: 20
<212> TYPE: DNA
<213> ORGANISM: Sorghum bicolor
<220> FEATURE:
<221> NAME/KEY: misc_feature
<223> OTHER INFORMATION: CAD12-R oligonucleotide primer

<400> SEQUENCE: 61
aagcccacaa ttactaaagg                                              20
```